US010918661B2

(12) United States Patent
Yu et al.

(10) Patent No.: US 10,918,661 B2
(45) Date of Patent: *Feb. 16, 2021

(54) SKIN COMPOSITIONS AND METHODS OF USE THEREOF

(71) Applicant: Shiseido Americas Corporation, New York, NY (US)

(72) Inventors: Betty Yu, Cambridge, MA (US); Joseph Lomakin, Cambridge, MA (US); Soo-Young Kang, Cambridge, MA (US); Benjamin W. Adams, Seattle, MA (US)

(73) Assignee: Shiseido Company, Limited, Tokyo (JP)

( * ) Notice: Subject to any disclaimer, the term of this patent is extended or adjusted under 35 U.S.C. 154(b) by 138 days.

This patent is subject to a terminal disclaimer.

(21) Appl. No.: 15/947,132

(22) Filed: Apr. 6, 2018

(65) Prior Publication Data

US 2018/0256636 A1  Sep. 13, 2018

Related U.S. Application Data

(60) Division of application No. 15/095,471, filed on Apr. 11, 2016, now Pat. No. 9,937,200, which is a continuation of application No. 13/933,300, filed on Jul. 2, 2013, now Pat. No. 9,308,221, which is a continuation of application No. 13/430,586, filed on Mar. 26, 2012, now abandoned, which is a continuation of application No. PCT/US2011/050016, filed on Aug. 31, 2011.

(60) Provisional application No. 61/500,455, filed on Jun. 23, 2011, provisional application No. 61/499,002, filed on Jun. 20, 2011, provisional application No. 61/496,420, filed on Jun. 13, 2011, provisional application No. 61/493,020, filed on Jun. 3, 2011, provisional application No. 61/489,119, filed on May 23, 2011, provisional application No. 61/486,643, filed on May 16, 2011, provisional application No. 61/472,995, filed on Apr. 7, 2011, provisional (Continued)

(51) Int. Cl.
A61K 31/765 (2006.01)
A61K 8/02 (2006.01)
A61K 8/25 (2006.01)
A61L 26/00 (2006.01)
A61Q 19/00 (2006.01)
A61Q 19/06 (2006.01)
A61K 8/34 (2006.01)
A61K 8/891 (2006.01)
A61Q 1/02 (2006.01)
A61Q 1/14 (2006.01)
A61K 8/895 (2006.01)
A61P 17/02 (2006.01)
A61Q 19/08 (2006.01)
A61K 8/19 (2006.01)
A61K 8/29 (2006.01)
A61K 8/58 (2006.01)
A61K 8/894 (2006.01)

(52) U.S. Cl.
CPC .......... *A61K 31/765* (2013.01); *A61K 8/0204* (2013.01); *A61K 8/19* (2013.01); *A61K 8/25* (2013.01); *A61K 8/29* (2013.01); *A61K 8/345* (2013.01); *A61K 8/585* (2013.01); *A61K 8/891* (2013.01); *A61K 8/894* (2013.01); *A61K 8/895* (2013.01); *A61L 26/0019* (2013.01); *A61L 26/0095* (2013.01); *A61Q 1/02* (2013.01); *A61Q 1/14* (2013.01); *A61Q 19/00* (2013.01); *A61Q 19/06* (2013.01); *A61Q 19/08* (2013.01); *A61K 2800/412* (2013.01); *A61K 2800/43* (2013.01); *A61K 2800/58* (2013.01); *A61K 2800/5922* (2013.01); *A61K 2800/884* (2013.01); *A61K 2800/95* (2013.01)

(58) Field of Classification Search
None
See application file for complete search history.

(56) References Cited

U.S. PATENT DOCUMENTS 3,261,802 A   7/1966  Bobear et al.
3,882,083 A   5/1975  Berger et al.
(Continued)

FOREIGN PATENT DOCUMENTS

EP   0445982 A2   9/1991
EP   0851000 A2   7/1998
(Continued)

OTHER PUBLICATIONS

Gelest, Safety Data Sheet HMS-301, pp. 1-5. (Year: 2014).*
Brook et al. (2007). "Pretreatment of Liquid Silicone Rubbers to Remove Volatile Siloxanes," *Ind. Eng. Chem. Res.* 46:8796-8805.
Correct Combo, [retrieved on Dec. 10, 2014 from on-line website http://www.drugs.com/otc/122754/correct-combo.html].
(Continued)

*Primary Examiner* — Abigail Vanhorn
(74) *Attorney, Agent, or Firm* — Jones Day

(57) ABSTRACT

The present invention provides durable, natural looking, non-invasive compositions that exhibit desired aesthetic qualities for therapeutic treatments. Specifically, the compositions can be used for the treatment of wounds and headaches. In addition, the compositions of the invention can be used to deliver agents to the subject in need thereof. In one embodiment, the invention pertains, at least in part, to methods for treating wounds, comprising applying to a subject's skin a formulation comprising a) a first reactive reinforcing component; and b) a second cross-linking component; in which the cross-linking component catalyzes an in situ cross-linking of the reactive reinforcing component, such that a film is formed on the wound, thereby treating the wound.

54 Claims, 2 Drawing Sheets

Related U.S. Application Data application No. 61/446,377, filed on Feb. 24, 2011, provisional application No. 61/432,458, filed on Jan. 13, 2011, provisional application No. 61/412,531, filed on Nov. 11, 2010, provisional application No. 61/378,504, filed on Aug. 31, 2010.

(56) References Cited

U.S. PATENT DOCUMENTS

| | | | |
|---|---|---|---|
| 3,884,866 A | 5/1975 | Jeram et al. | |
| 4,025,485 A | 5/1977 | Kodama et al. | |
| 4,683,278 A | 7/1987 | Toshio | |
| 4,908,140 A | 3/1990 | Bausch et al. | |
| 5,173,291 A | 12/1992 | Brink | |
| 5,190,827 A | 3/1993 | Lin et al. | |
| 5,219,560 A | 6/1993 | Suzuki et al. | |
| 5,525,344 A | 6/1996 | Wivell | |
| 5,534,609 A | 7/1996 | Lewis et al. | |
| 5,616,632 A | 4/1997 | Fujiki et al. | |
| 5,800,816 A | 9/1998 | Brieva et al. | |
| 5,919,437 A | 7/1999 | Lee et al. | |
| 5,919,468 A | 7/1999 | Bara | |
| 5,922,470 A | 7/1999 | Bracken et al. | |
| 6,066,326 A | 5/2000 | Afriat et al. | |
| 6,313,190 B1 | 11/2001 | Bublewitz et al. | |
| 6,342,237 B1 | 1/2002 | Bara | |
| 6,355,724 B1 | 3/2002 | LeGrow et al. | |
| 6,391,944 B2 | 5/2002 | Canpont et al. | |
| 6,423,322 B1 | 7/2002 | Fry | |
| 6,471,985 B2 | 10/2002 | Guyuron et al. | |
| 6,512,072 B1 | 1/2003 | Gantner et al. | |
| 6,544,532 B1 | 4/2003 | Jager-Lezer et al. | |
| 6,545,076 B2 | 4/2003 | Kaiya et al. | |
| 6,573,299 B1 | 6/2003 | Petrus | |
| 6,613,185 B1 | 9/2003 | Valade et al. | |
| 6,682,749 B1 | 1/2004 | Potechin et al. | |
| 6,762,242 B1 | 7/2004 | Torto et al. | |
| 6,998,427 B2 | 2/2006 | Del Torto et al. | |
| 7,078,026 B2 | 7/2006 | Ferrari et al. | |
| 7,083,800 B1 | 8/2006 | Terren et al. | |
| 7,148,306 B2 | 12/2006 | Frank et al. | |
| 7,270,828 B2 | 9/2007 | Masuda et al. | |
| 7,273,658 B2 | 9/2007 | Benayoun et al. | |
| 7,335,708 B2 | 2/2008 | Bublewitz et al. | |
| 7,452,957 B2 | 11/2008 | Curtis | |
| 7,482,419 B2 | 1/2009 | Caprasse et al. | |
| 7,572,514 B2 | 8/2009 | Howe et al. | |
| 7,750,106 B2 | 7/2010 | Zheng et al. | |
| 8,133,478 B2 | 3/2012 | Maitra et al. | |
| 8,263,055 B2 | 9/2012 | Do | |
| 8,569,792 B2 | 10/2013 | Mitani et al. | |
| 8,611,746 B2 | 12/2013 | Pincemin et al. | |
| 8,658,755 B2 | 2/2014 | Saito | |
| 8,691,202 B2 | 4/2014 | Yu et al. | |
| 8,920,783 B2 | 12/2014 | Lin | |
| 9,044,288 B2 | 6/2015 | Angeletakis | |
| 9,096,721 B2 | 8/2015 | Garaud et al. | |
| 9,114,096 B2 | 8/2015 | Yu et al. | |
| 9,186,315 B2 | 11/2015 | Singer | |
| 9,308,221 B2 | 4/2016 | Yu et al. | |
| 9,333,223 B2 | 5/2016 | Yu et al. | |
| 9,511,034 B1 | 12/2016 | Garrett | |
| 9,724,363 B2 * | 8/2017 | Yu | A61K 8/19 |
| 2002/0022040 A1 | 2/2002 | Robinson et al. | |
| 2002/0122771 A1 | 9/2002 | Holland et al. | |
| 2003/0180281 A1 | 9/2003 | Bott et al. | |
| 2004/0258628 A1 | 12/2004 | Riedel et al. | |
| 2005/0148727 A1 | 7/2005 | Ajbani et al. | |
| 2005/0158260 A1 | 7/2005 | Ferrari et al. | |
| 2005/0175562 A1 | 8/2005 | Hadasch et al. | |
| 2006/0029623 A1 | 2/2006 | Astruc et al. | |
| 2007/0142575 A1 | 6/2007 | Zheng et al. | |
| 2007/0142599 A1 | 6/2007 | Zheng et al. | |
| 2007/0212314 A1 | 9/2007 | Murphy et al. | |
| 2007/0244230 A1 | 10/2007 | Sixt et al. | |
| 2008/0102050 A1 | 5/2008 | Li et al. | |
| 2008/0159970 A1 | 7/2008 | Willemin | |
| 2008/0279797 A1 | 11/2008 | Maitra et al. | |
| 2009/0035246 A1 | 2/2009 | Do | |
| 2009/0214455 A1 | 8/2009 | Blin et al. | |
| 2009/0317343 A1 | 12/2009 | Lin et al. | |
| 2010/0112019 A1 | 5/2010 | Thevenet | |
| 2010/0152135 A1 | 6/2010 | Blin | |
| 2010/0178266 A1 | 7/2010 | Huggins et al. | |
| 2010/0179105 A1 | 7/2010 | Blin et al. | |
| 2011/0040242 A1 | 2/2011 | Fallon et al. | |
| 2011/0166275 A1 | 7/2011 | Zhang | |
| 2012/0237461 A1 | 9/2012 | Yu et al. | |
| 2012/0251600 A1 | 10/2012 | Yu et al. | |
| 2013/0052356 A1 | 2/2013 | Li | |
| 2013/0078209 A1 | 3/2013 | Yu et al. | |
| 2013/0178571 A1 | 7/2013 | Ogawa et al. | |
| 2014/0004065 A1 | 1/2014 | Souda et al. | |
| 2014/0004073 A1 | 1/2014 | Yu et al. | |
| 2014/0010769 A1 | 1/2014 | Lomakin et al. | |
| 2014/0044670 A1 | 2/2014 | Yu et al. | |
| 2014/0322519 A1 | 10/2014 | Ahn et al. | |
| 2015/0190516 A1 | 7/2015 | Cauvin et al. | |
| 2015/0274971 A1 | 10/2015 | Endo et al. | |
| 2015/0284590 A1 | 10/2015 | Endo et al. | |
| 2016/0143840 A1 | 5/2016 | Yu et al. | |
| 2016/0250250 A1 | 9/2016 | Yu et al. | |
| 2016/0317574 A1 | 11/2016 | Yu et al. | |
| 2017/0189317 A1 | 7/2017 | Bernard et al. | |
| 2017/0360824 A1 * | 12/2017 | Yu | A61K 8/894 |
| 2018/0296591 A1 * | 10/2018 | Yu | A61K 31/80 |

FOREIGN PATENT DOCUMENTS

| | | |
|---|---|---|
| EP | 0865787 A1 | 9/1998 |
| EP | 2090294 A1 | 8/2009 |
| FR | 2894817 A1 | 6/2007 |
| FR | 2910291 A1 | 6/2008 |
| FR | 2954143 A1 | 6/2011 |
| FR | 2956319 B1 | 8/2011 |
| JP | 2009/520002 A | 5/2009 |
| JP | 2009/530480 A | 8/2009 |
| WO | WO-2000/074738 A1 | 12/2000 |
| WO | WO-2007/071886 A2 | 6/2007 |
| WO | WO-2007/102859 A2 | 9/2007 |
| WO | WO-2007/117284 A2 | 10/2007 |
| WO | WO-2008/075282 A2 | 6/2008 |
| WO | WO-2009/042732 A1 | 4/2009 |
| WO | WO-2009/090074 A1 | 7/2009 |
| WO | WO-2009/090242 A1 | 7/2009 |
| WO | WO-2011/001217 A1 | 1/2011 |
| WO | WO-2012/030984 A1 | 3/2012 |
| WO | WO-2012/030993 A2 | 3/2012 |
| WO | WO-2013/044098 A1 | 3/2013 |
| WO | WO-2013/070302 A1 | 5/2013 |
| WO | WO-2013/076450 A1 | 5/2013 |
| WO | WO-2013/158844 A2 | 10/2013 |
| WO | WO-2015/068859 A1 | 5/2015 |
| WO | WO-2017/117438 A1 | 7/2017 |

OTHER PUBLICATIONS

European Search Report, Application No. EP11822576, dated Mar. 16, 2015.
Fumed Silica: retrieved form internet: http://www.powerchemcorp.com/library/public/fumed_silica/SiSiB_Fumed_Silica.pdf. Retrieved on Sep. 4, 2016.
Hwang, S.M. et al. (2001). "Basis of Occlusive Therapy in Psoriasis: Correcting Defects in Permeability Barrier and Calcium Gradient," *International Journal of Dermatology* 40:223-231.
International Preliminary Report on Patentability dated Mar. 5, 2013 for PCT Application No. PCT/US2011/050016 filed on Aug. 31, 2011, 5 pages.
Written Opinion of the International Search Authority dated Apr. 30, 2012, for PCT Application No. PCT/US2011/050016 filed on Aug. 31, 2011, 4 pages.
International Search Report for related PCT Application No. PCT/US2011/050016, dated Apr. 30, 2012; 4 pages.

(56) References Cited

OTHER PUBLICATIONS

Japanese Office Action, Application No. JP 2013-527273, dated Jun. 23, 2015.

Klykken, P. et al. (2004). "Silicone Film-Forming Technologies for Health Care Applications," *Dow Corning*; 8pp.

Leow, Y-H et al. (1997, e-pub. Jul. 12, 2009). "Effect of Occlusion on Skin," Journal of Dermatological Treatment 8(2):139-142.

Liquid Silicone Rubber: Global Product Selection Guide: retrieved from internet: https://www.dowcorning.com/content/publishedlit/95/1226-lsr-selection-guide.pdf. Retrieved on Sep. 4, 2016.

Ostergaard, Dow corning SA, Next Generation Rheology Control rings New Formulation Options for Personal Care, pp. 1-6:2008.

Quartz Powder: retrieved from internet: http://www.cosmeticanalysis.com/cosmetic-ingredients/quartz-powder.html. Retrieved on Apr. 25, 2017.

Silc Pig: retrieved from internet: https://www.smooth-on.com/product-line/silc-pig/. Retrieved on Sep. 4, 2016.

Silicones Plus product list, [retrieved on Dec. 10, 2014 from on-line website http://siliconesplus.com/storage/Silicones% 20Pius% 20Brochure_ 1.pdf].

TraumaSkin FX™ Platinum Silicone Sculpting/Casting Medium: retrieved from internet: http ://web. arch ive.org/web/201 00407000529/http://www. pai ntandpowderstore.com/p roducts.php ?cat=4 7. Retrieved on Apr. 25, 2017.

Yu, B. et al. (May 9, 2016). "An Elastic Second Skin," *Nature Materials* pp. 1-10.

Zhai, H. et al. (2001). "Effects of Skin Occlusion on Percutaneous Absorption: An Overview," *Skin Pharmacol Appl Skin Physiol* 14(1):1-10.

Zhai, H. et al. (2002). "Occlusion vs. Skin Barrier Function," *Skin Research and Technology* 8:1-6.

* cited by examiner

SKIN COMPOSITIONS AND METHODS OF USE THEREOF

RELATED APPLICATIONS

This application is a divisional of U.S. application Ser. No. 15/095,471, filed Apr. 11, 2016, currently allowed, which is a continuation of U.S. patent application Ser. No. 13/933,300, filed Jul. 2, 2013, now U.S. Pat. No. 9,308,221, issued Apr. 12, 2016, which is a continuation of U.S. application Ser. No. 13/430,586, filed Mar. 26, 2012, currently abandoned, which is a continuation of International Patent Application No. PCT/US2011/050016, filed Aug. 31, 2011, which claims the benefit of previously filed U.S. Provisional Patent Application No. 61/500,455, filed Jun. 23, 2011; U.S. Provisional Patent Application No. 61/499,002, filed Jun. 20, 2011; U.S. Provisional Patent Application 61/496,420, filed Jun. 13, 2011; U.S. Provisional Patent Application No. 61/493,020, filed Jun. 3, 2011; U.S. Provisional Patent Application No. 61/489,119, filed May 23, 2011; U.S. Provisional Patent Application No. 61/486,643, filed May 16, 2011; U.S. Provisional Patent Application No. 61/472,995, filed Apr. 7, 2011; U.S. Provisional Patent Application No. 61/446,337, filed Feb. 24, 2011; U.S. Provisional Patent Application No. 61/432,458, filed Jan. 13, 2011; U.S. Provisional Patent Application No. 61/412,531, filed on Nov. 11, 2010 and U.S. Provisional Patent Application No. 61/378,504, filed on Aug. 31, 2010. The entire contents of the foregoing applications are hereby incorporated by reference.

BACKGROUND OF THE INVENTION

The skin acts an a protective barrier from the external environment. When damaged, a cascade of events is triggered to repair to the damaged tissue. Wound healing is a complex process, progressing through four stages (inflammation, proliferation, remodeling, and epithelialization) to repair the damaged area. Although wound healing is a natural process, disruption of the events involved may lead to incomplete healing and further damage to the tissue. Current methods of treating wounds include applying a dressing to the wound to stem bleeding, prevent infection and encourage healing. Wound dressings are often made from breathable material (for example, gauze). Occlusive dressings have been used on wounds, but the effects of occlusion on wounded skin are not completely understood (see e.g., Leow and Mailbach; *J Dermatol Treat*, (1997) 8, 139-142).

However, current methods of using occlusion on wounded skin is unsatisfactory because current occlusive dressings are not durable, convenient, or long lasting. Moreover, some current occlusive coverings require subjects to wrap plastic around the area to be treated, lowering subject compliance because the treatment is cumbersome and uncomfortable. Lastly, current occlusive coverings do not permit the exposure of the wound to the environment to be modulated based upon the nature of the wound. For example, current occlusive dressings are designed to exclude both air and water, and generally it is not possible to permit exposure to one and not the other.

Headaches cause pain in the head and neck and arise from a myriad of causes. While most are not life-threatening, headaches can be very painful and debilitating. Headache remedies include from over the counter analgesics, prescription medications, acupuncture and massage.

The commercially available polymer materials used in therapeutic products today do not necessarily provide the elasticity, environmental resistance and skin adhesion for long lasting product performance nor do they provide the aesthetic feel and appearance required by the consumer of therapeutic products.

SUMMARY OF THE INVENTION

The present invention provides durable, natural looking, non-invasive compositions that exhibit desired aesthetic qualities for therapeutic treatments. Specifically, the compositions can be used for the treatment of wounds and headaches. In addition, the compositions of the invention can be used to deliver agents to the subject in need thereof.

In one embodiment, the invention pertains, at least in part, to methods for treating wounds, comprising applying to a subject's skin a formulation comprising a) a first reactive reinforcing component; and b) a second cross-linking component; in which the cross-linking component catalyzes an in situ cross-linking of the reactive reinforcing component, such that a film is formed on the wound, thereby treating the wound.

In one embodiment, the invention pertains, at least in part, to methods for preventing a wound from occurring, comprising applying to a wound on a subject a formulation comprising a) a first reactive reinforcing component; and b) a second cross-linking component; in which the cross-linking component catalyzes an in situ cross-linking of the reactive reinforcing component, such that a film is formed on the wound, thereby preventing the occurrence of the wound.

The current invention has many advantages. The invention provides a durable, convenient, long-lasting occlusive coating. The formulation, composition or film of the invention provides a transparent or a tinted coating for the treatment site. The formulation, composition or film of the invention is more comfortable because it forms a layer over the skin and therefore increases subject compliance as compared to current occlusive coatings. Moreover, the chemical and physical properties of the formulation, composition or film of the invention are tunable to form an occlusive coating that is best suited for the location on the subject and the type of wound to be treated.

In one embodiment, the invention pertains, at least in part, to methods for delivering an agent to a subject, comprising applying to the subject's skin a formulation comprising a) a first reactive reinforcing component optionally comprising one or more agents; and b) a second cross-linking component optionally comprising one or more agents; in which the cross-linking component catalyzes an in situ cross-linking of the reactive reinforcing component such that a film is formed on the skin, thereby delivering the agent to the subject.

In one embodiment, the invention pertains, at least in part, to methods of treating a headache in a subject comprising applying to an appropriate area of the subject's skin a formulation in an amount effective to lift the subject's brow, the formulation comprising a) a first reactive reinforcing component and b) a second cross-linking component; in which the cross-linking component catalyzes an in situ cross-linking of the reactive reinforcing component such that a film is formed on the skin, thereby treating the headache. In one embodiment, the invention pertains, at least in part, to therapeutic formulations for application to a subject's body, comprising at least one preselected function modulating component, in which the composition forms a therapeutic film upon application to the subject's body.

In one embodiment, the invention pertains, at least in part, to therapeutic formulations for application to a subject's skin that target a treatment area on a subject's body, comprising at least one preselected treatment specific component, wherein the composition forms a therapeutic film upon application to the target treatment area on the subject's body.

In one embodiment, the invention pertains, at least in part, to a film removing cleanser for use in removing a therapeutic film, wherein the film is prepared by a process comprising the steps of applying a reactive reinforcing component to skin; and applying a cross-linking component to said reactive reinforcing component, and wherein said cross-linking component catalyzes an in situ cross-linking of the reactive reinforcing component.

In another embodiment, the invention pertains, at least in part, to a film removing cleanser comprising a film wetting component, a penetration component, a film swelling component and a film release component.

In some embodiments, the invention pertains to a formulation for repairing a therapeutic film applied to skin, wherein said formulation comprises a) a first reactive reinforcing component and b) a second cross-linking component, wherein the cross-linking component catalyzes an in situ cross-linking of the reactive reinforcing component such that a film is formed on the skin.

In some embodiments, the invention pertains, at least in part, to a method for repairing a therapeutic film applied to skin comprising the steps of a) identifying an area of the film in need of repair; b) optionally smoothing the edges of the film; and c) applying a formulation for repairing the film, wherein the formulation comprises a first reactive reinforcing component and a second cross-linking component, wherein the cross-linking component catalyzes an in situ cross-linking of the reactive reinforcing component such that a film is formed on the skin, thereby repairing the therapeutic film.

In some embodiments, the invention pertains, at least in part, to a kit for repairing a therapeutic film, the kit comprising a formulation comprising a) a first reactive reinforcing component and b) a second cross-linking component, wherein the cross-linking component catalyzes an in situ cross-linking of the reactive reinforcing component such that a film is formed on the skin.

DETAILED DESCRIPTION OF THE INVENTION

Figure 1:
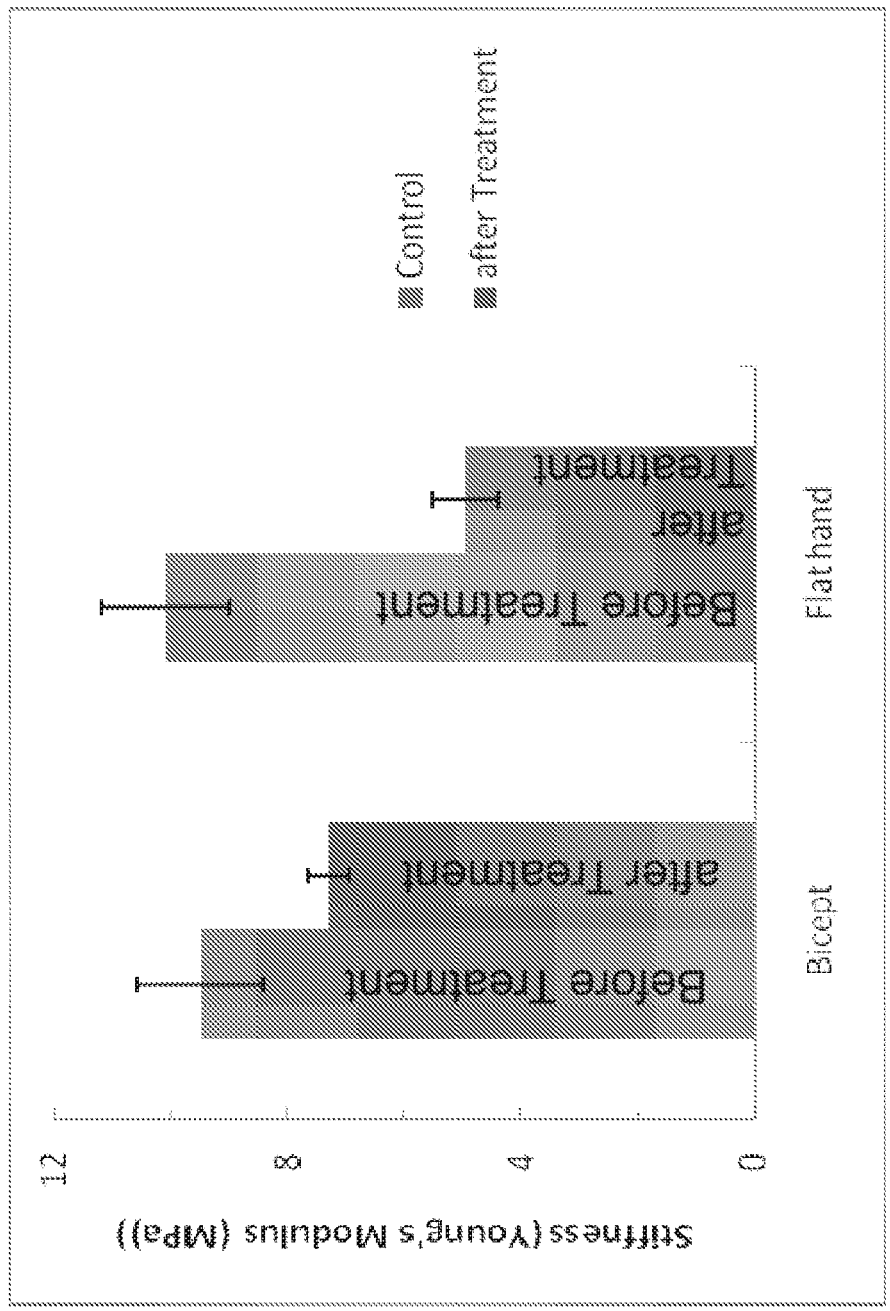
FIG. 1 is a chart illustrating the change in the Young's Modulus of the skin after the application of a formulation of the invention. The change in Young's Modulus indicates that there is a reduction in the stiffness of skin upon application of the formulation.

In some embodiments, the invention pertains, at least in part, to therapeutic formulations for application to the skin that comprise a) a reactive reinforcing component; and b) a cross-linking component; in which the cross-linking component catalyzes an in situ cross-linking of the reactive reinforcing component, such that a therapeutic film is formed on the skin.

The language "therapeutic formulation" or "formulation" includes therapeutic compositions that, when applied to the body of a subject in need of treatment, form a film on the body resulting in a therapeutic benefit to the subject. Therapeutic benefits include, but are not limited to, wound healing and amelioration of headache pain.

The language "wounds" includes injuries to the skin wherein the skin is torn, cut or punctured. A wound is a break in the skin. In one embodiment, the wound is caused by skin contact with a foreign object. The break in the skin may cause external bleeding. Wounds include open wounds, for example, abrasions, lacerations, incisions, punctures, avulsions, or amputations. Wounds also include burn wounds. A burn is a type of injury to flesh caused by heat, electricity, chemicals, light, radiation or friction.

In one embodiment of the invention, the compositions, formulations or films of the invention treat the wound of the subject, in addition to masking, concealing, or covering the wound.

In at least one embodiment, a wound does not include skin or body imperfection or a dermatological disorders.

The language "skin or body imperfections" include those items on a subject's skin that the subject perceives as a blemish or a flaw. Examples of skin imperfections include port wine stain or nevus flammeus (e.g., nevus flammeus nuchae or midline nevus flammeus) melasma, wrinkles, blemishes, acne, moles, scars, tattoos, bruises, skin disfigurements, birth marks, sun damage, age damage, uneven skin tone, sagging skin, skin roughness, hyperpigmentation, enlarged pores, telangiectasia, redness, shine, cellulite, stretch marks or loss of skin elasticity.

The language "dermatological disorder" includes disorders that cause at least one symptom on the skin of a subject requiring medical treatment. In one embodiment, dermatological disorders are caused by autoimmune disorders. In another embodiment, a dermatological disorder is caused by environmental factors, such a allergens or chemicals. Examples of symptoms of dermatological disorders requiring treatment is dermatitis, itchy skin, dry skin, crusting, blistering, or cracking skin, skin edema, or skin lesion formation. Dermatological disorders include, but are not limited to, lichen simplex chronicus, cutaneous lupus (e.g., acute cutaneous lupus, subacute cutaneous lupus, chronic cutaneous lupus, chilblain lupus erythematosus, discoid lupus erythematosus, lupus erythematosus-lichen planus overlap syndrome, lupus erythematosus panniculitis, tumid lupus erythematosus and verrucous lupus erythematosus), psoriasis (e.g., psoriasis vulgaris, psoriatic erythroderma, pustular psoriasis, drug-induced psoriasis, inverse psoriasis, seborrheic-like psoriasis and guttate psoriasis), eczema (e.g., atopic eczema, atopic dermatitis, contact dermatitis, xerotic eczema, seborrhoeic dermatitis, dyshidrosis, discoid eczema, venous eczema, dermatitis herpetiformis, neurodermatitis and autoeczematization), or chronic dry skin.

In one embodiment, the therapeutic formulations include a reactive reinforcing component and a cross-linking component. The language "reactive reinforcing component" includes a component that, when applied to the skin as a first component, is the basis of the therapeutic film that is formed upon application of the cross-linking component to the reactive reinforcing component. In one embodiment, the reactive reinforcing component includes at least one reactive constituent and at least one reinforcing constituent.

The language "reactive constituent" includes one or more constituents of the reactive reinforcing component that provide the reactive film-forming elements of the formulation. In some embodiments, the reactive constituent includes at least one polysiloxane, polyethylene oxide, polypropylene oxide, polyurea, polyurethane, polyester (including polylactic-co-glycolic acid, polycaprolactone, polylactic acid, polyglycolic acid, and polyhydroxybutyrate, polyamide, or polysulfone. In another embodiment, the reactive constituent is a compound of formula I:

$$W-[X]_s-V-[Y]_t-Z \quad (I)$$

wherein
W is $R^1R^2R^3SiO-$, $-NR^5R^6$, $-CR^7R^8R^9$ or $C_{5-10}$ aryl;
X is $-R^{11}R^{12}Si-O-$, $-OCONR^{13}-$, $-NR^{14}CONR^{15}-$, $-CO-$, $-NR^{16}CO-$, $-SO_2-$, $-O-$, $-S-$ or $-NR^{17}-$;
V is absent, $C_{1-20}$ alkyl, $C_{2-20}$ alkenyl, $C_{5-10}$ aryl, $-O-$, $-NR^{10}-$ or $-S-$;
Y is $-R^{18}R^{19}Si-O-$, $-OCONR^{20}-$, $-NR^{21}CONR^{22}-$, $-CO-$, $-NR^{23}CO-$, $-SO_2-$, $-O-$, $-S-$ or $-NR^{24}-$;
Z is $-SiR^{25}R^{26}R^{27}$, $-OR^{28}$, $-NR^{29}R^{30}$, $-CR^{31}R^{32}$ or $C_{5-10}$ aryl; $R^1, R^2, R^3, R^7, R^8, R^9, R^{11}, R^{12}, R^{18}R^{19}, R^{25}, R^{26}, R^{27}, R^{31}, R^{32}$ and $R^{33}$ are each independently hydrogen, $C_{1-20}$ alkyl, $C_{2-20}$ alkenyl, $C_{5-10}$ aryl, hydroxyl or $C_{1-20}$ alkoxyl;
$R^4, R^5, R^6, R^{13}, R^{14}, R^{15}, R^{16}, R^{17}, R^{20}, R^{21}, R^{22}, R^{23}, R^{24}, R^{28}, R^{29}$ and $R^{30}$ are each independently hydrogen, $C_{1-20}$ alkyl, $C_{2-20}$ alkenyl, $C_{5-10}$ aryl; and
s and t are each independently an integer from about 0 to about 6000.

X and Y of formula I represent an independent "monomer unit." The number of X and Y monomer units present in formula I is provided by the value of s and t, respectively. Representative monomer units include:

[chemical structures of monomer units]

where R is as for defined for $R^1$, $R^2$, $R^3$, etc, above.
It is understood that when more than one X (or Y) monomer unit is present (e.g. s (or t) is more than one), the values for $R^{11}, R^{12}, R^{13}, R^{14}, R^{15}, R^{16}, R^{17}, R^{18}R^{19}, R^{20}, R^{21}, R^{22}, R^{23}$, and $R^{24}$ are selected independently for each individual monomer unit described by $-[X]_s-$ (or $-[Y]_t-$). For example, if the value of the monomer unit X is $-R^{11}R^{12}Si-O-$ and the value of s is 3, then $-[X]_s-$ is $:-[R^{11}R^{12}Si-O-R^{11}R^{12}Si-O-R^{11}R^{12}Si-O]-.$ In this example, it is understood that the three $R^{11}$ groups present in may be the same or different from each other, for example, one $R^{11}$ may be hydrogen, and the two other $R^{11}$ groups may be methyl.

W and Z of formula I represent independent terminal caps, one on each end of the. For example, terminal caps include:

[chemical structures of terminal caps]

wherein $\xi$ denotes attachment to a monomer unit and wherein R is as for defined for $R^1$, $R^2$, $R^3$, etc., above. In one embodiment,
W is $R^1R^2R^3SiO-$, $-OR^4$, $-NR^5R^6$, $-CR^7R^8R^9$ or $C_{5-10}$ aryl;
X is $-R^{11}R^{12}Si-O-$, or $-NR^{14}CONR^{15}-$;
V is absent, $C_{1-20}$ alkyl, $C_{2-20}$ alkenyl, $C_{5-10}$ aryl, $-O-$, $-NR^{10}-$ or $-S-$;
Y is $-R^{18}R^{19}Si-O-$, or $-NR^{21}CONR^{22}-$;
Z is $-SiR^{25}R^{26}R^{27}$, $-OR^{28}$, $-NR^{29}R^{30}$, $-CR^{31}R^{32}R^{33}$ or $C_{5-10}$ aryl;
$R^1, R^2, R^3, R^7, R^8, R^9, R^{11}, R^{12}, R^{18}R^{19}, R^{25}, R^{26}, R^{27}, R^{31}, R^{32}$ and $R^{33}$ are each independently hydrogen, $C_{1-20}$ alkyl, $C_{2-20}$ alkenyl, $C_{5-10}$ aryl, hydroxyl or $C_{1-20}$ alkoxyl;
$R^4, R^5, R^6, R^{14}, R^{15}, R^{21}, R^{22}, R^{28}, R^{29}$ and $R^{30}$ are each independently hydrogen, $C_{1-20}$ alkyl, $C_{2-20}$ alkenyl, $C_{5-10}$ aryl; and
s and t are each independently an integer from about 0 to about 6000, wherein the sum of s and t is not 0.
In one embodiment,
W is $R^1R^2R^3SiO-$, $-CR^7R^8R^9$ or $C_{5-10}$ aryl;
X is $-R^{11}R^{12}Si-O-$, or $-NR^{14}CONR^{15}-$;
V is absent, $C_{1-20}$ alkyl, $C_{2-20}$ alkenyl, or $C_{5-10}$ aryl;
Y is $-R^{18}R^{19}Si-O-$, or $-NR^{21}CONR^{22}-$;
Z is $-SiR^{25}R^{26}R^{27}$, $-CR^{31}R^{32}R^{33}$ or $C_{5-10}$ aryl;
$R^1, R^2, R^3, R^7, R^8, R^9, R^{11}, R^{12}, R^{18}R^{19}, R^{25}, R^{26}, R^{27}, R^{31}, R^{32}$ and $R^{33}$ are each independently hydrogen, $C_{1-20}$ alkyl, $C_{2-20}$ alkenyl, $C_{5-10}$ aryl, hydroxyl or $C_{1-20}$ alkoxyl;
$R^{14}, R^{15}, R^{21}$, and $R^{22}$ are each independently hydrogen, $C_{1-20}$ alkyl, $C_{2-20}$ alkenyl, $C_{5-10}$ aryl; and
s and t are each independently an integer from about 0 to about 6000, wherein the sum of s and t is not 0.
In one embodiment, V is absent, W is $R^1R^2R^3SiO-$; X is $-R^{11}R^{12}Si-O-$; Y is $R^{18}R^{19}Si-O-$; Z is $-SiR^{25}R^{26}R^{27}$; and $R^1, R^2, R^3, R^{12}, R^{18}, R^{19}, R^{25}, R^{26}$ and $R^{27}$ are each independently selected from $C_{1-20}$ alkyl (e.g., $C_1$ alkyl, such as methyl) or $C_{2-20}$ alkenyl (e.g., $C_2$ alkenyl, such as vinyl). In one embodiment, at least one of $R^1, R^2, R^3, R^{11}, R^{12}, R^{18}, R^{19}, R^{25}, R^{26}$ and $R^{27}$ is $C_{2-20}$ alkenyl, for example, $C_2$ alkenyl (e.g., vinyl). In another embodiment, at least two of $R^1, R^2, R^3, R^{11}, R^{12}, R^{18}, R^{19}, R^{25}, R^{26}$ and $R^{27}$ are $C_{2-20}$ alkenyl, for example, $C_2$ alkenyl (e.g., vinyl). In some embodiments, at least one of $R^1, R^2, R^3, R^{25}, R^{26}$ and $R^{27}$ are each $C_{2-20}$ alkenyl, for example, $C_2$ alkenyl (e.g., vinyl).
In one embodiment, V is absent, W is $R^1R^2R^3SiO-$; X is $-R^{11}R^{12}Si-O-$; Y is $-R^{18}R^{19}Si-O-$; Z is —SiR$^{25}$R$^{26}$R$^{27}$; and R$^1$, R$^2$, R$^3$, R$^{25}$, R$^{26}$ and R$^{27}$ are each independently selected from C$_{1-20}$ alkyl (e.g., C$_1$ alkyl, such as methyl) or C$_{2-20}$ alkenyl (e.g., C$_2$ alkenyl, such as vinyl); and R$^{11}$, R$^{12}$, R$^{18}$, and R$^{19}$ are each independently selected from C$_{1-20}$ alkyl (e.g., C$_1$ alkyl, such as methyl). In one embodiment, at least one of R$^1$, R$^2$, R$^3$, and at least one of R$^{25}$, R$^{26}$ and R$^{27}$ is C$_{2-20}$ alkenyl, for example, C$_2$ alkenyl (e.g., vinyl). In one embodiment, one of R$^1$, R$^2$, R$^3$ is C$_2$ alkenyl (e.g., vinyl) and the others are C$_{1-20}$ alkyl (e.g., C$_1$ alkyl, such as methyl), and at least one of R$^{25}$, R$^{26}$ and R$^{27}$ is C$_{2-20}$ alkenyl, for example, C$_2$ alkenyl (e.g., vinyl) and the others are C$_{1-20}$ alkyl (e.g., C$_1$ alkyl, such as methyl). In one embodiment, at least one of R$^{11}$ or R$^{12}$ and at least one of R$^{18}$ or R$^{19}$ is C$_{2-20}$ alkenyl, for example, C$_2$ alkenyl (e.g., vinyl) for at least one monomer unit. In one embodiment, one of R$^{11}$ or R$^{12}$ is C$_2$ alkenyl (e.g., vinyl) and the others are C$_{1-20}$ alkyl (e.g., C$_1$ alkyl, such as methyl), and at least one of R$^{18}$ or R$^{19}$ is C$_{2-20}$ alkenyl, for example, C$_2$ alkenyl (e.g., vinyl) and the others are C$_{1-20}$ alkyl (e.g., C$_1$ alkyl, such as methyl) for at least one monomer unit.

In some embodiments, the organopolysiloxane includes vinyl moieties only at the terminal caps of the polymer. In some embodiments, the organopolysiloxane include vinyl moieties only in the monomer units, but not at the terminal cap of the polymer. In other embodiments, the organopolysiloxane includes vinyl moieties at both the terminal cap or in the monomer unit of the polymer. In one embodiment, the polymer includes two vinyl moieties located either at the terminal cap, or within the monomer unit, or a combination thereof.

In one embodiment, on average at least two vinyl moieties are present in the polymer. In a specific embodiment, at least two vinyl moieties are present in the polymer and at least two vinyl moieties are present on the two terminal caps of the polymer. In a specific embodiment, only two vinyl moieties are present in the polymer. In a specific embodiment, only two vinyl moieties are present in the polymer and are located on each of the terminal caps. In a specific embodiment, on average at least two vinyl moieties are present in the polymer and at least two vinyl moieties are present in one or more monomer units of the polymer. In a specific embodiment, at least two vinyl moieties are present anywhere in the polymer, but separated from another vinyl moiety by about 2000 monomer units, for example, 1500, 1600, 1700, 1800, 1900, 2000, 2100, 2200, 2300, 2400, or 2500 monomer units. In a specific embodiment, on average at least two vinyl moieties are present anywhere in the polymer, but separated from another vinyl moiety by about 850 monomer units, for example, 350, 450, 550, 650, 750, 850, 950, 1050, 1150, 1250, or 1350 monomer units. In a specific embodiment, on average greater two vinyl moieties are present anywhere in the polymer, but separated from another vinyl moiety by about 40 monomer units, for example, 5, 10, 15, 20, 25, 30, 35, 40, 45, 50, 55, 60, 65, 70, 75, or 80 monomer units. In a specific embodiment, one or more Si—H units are present in addition to the vinyl moiety. Alternatively, in one embodiment, if a vinyl moiety is present then a Si—H is not present.

In one embodiment, V is absent, W is R$^1$R$^2$R$^3$SiO—; X is —R$^{11}$R$^{12}$Si—O—; Y is —R$^{18}$R$^{19}$Si—O—; Z is —SiR$^{25}$R$^{26}$R$^{27}$, R$^1$, R$^2$, R$^3$, R$^{11}$, R$^{12}$, R$^{18}$, R$^{19}$, R$^{25}$, R$^{26}$ and R$^{27}$ are each independently are each independently selected from hydrogen or C$_{1-20}$ alkyl (e.g., C$_1$ alkyl, such as methyl). In one embodiment, R$^1$, R$^2$, R$^3$, R$^{25}$, R$^{26}$ and R$^{27}$ are each independently selected from C$_{1-20}$ alkyl (e.g., C$_1$ alkyl, such as methyl); and R$^{11}$, R$^{12}$, R$^{18}$, and R$^{19}$ are each independently selected from hydrogen or C$_{1-20}$ alkyl (e.g., C$_1$ alkyl, such as methyl), wherein at least one of and R$^{11}$, R$^{12}$, R$^{18}$, and R$^{19}$ are hydrogen for at least one monomer unit. In one embodiment, on average greater than two Si—H units (e.g. one or more of R$^{12}$, R$^{18}$, and R$^{19}$ is hydrogen) are present in the polymer, for example 3-15 Si—H units may be present. In a specific embodiment, 8 Si—H units are present. In one embodiment, one or more Si—H units (e.g. one or more of R$^{11}$, R$^{12}$, R$^{18}$, and R$^{19}$ is hydrogen) are present in the polymer. In one embodiment, at least two monomer units include a —Si—H unit (e.g. one or more of R$^{11}$, R$^{12}$, R$^{18}$, and R$^{19}$ is hydrogen). In one embodiment, at least three monomer units include a —Si—H unit (e.g. one or more of R$^{11}$, R$^{12}$, R$^{18}$, and R$^{19}$ is hydrogen). In one embodiment, at least four monomer units include a —Si—H unit (e.g. one or more of R$^{11}$, R$^{12}$, R$^{18}$, and R$^{19}$ is hydrogen). In one embodiment, at least five monomer units include a —Si—H unit (e.g. one or more of R$^{11}$, R$^{12}$, R$^{18}$, and R$^{19}$ is hydrogen). In one embodiment, at least six monomer units include a —Si—H unit (e.g. one or more of R$^{11}$, R$^{12}$, R$^{18}$, and R$^{19}$ is hydrogen). In one embodiment, at least seven monomer units include a —Si—H unit (e.g. one or more of R$^{11}$, R$^{12}$, R$^{18}$, and R$^{19}$ is hydrogen). In one embodiment, at least eight monomer units include a —Si—H unit (e.g. one or more of R$^{11}$, R$^{12}$, R$^{18}$, and R$^{19}$ is hydrogen). In one embodiment, a Si—H unit may be present in one or both the terminal caps in addition to being present in a monomer unit as described above. In a specific embodiment, Si-(alkyl) or Si-(vinyl) units may also be present in the polymer. In a specific embodiment, only Si—CH$_3$ and Si—H units are present. In a specific embodiment, monomer units or terminal caps include C$_1$-C$_{20}$alkyl, specifically methyl groups, for the non-Si—H positions of the polymer.

In a specific embodiment, on average at least two Si—H units are present in the polymer. In a specific embodiment, on average at least two Si—H moieties are present anywhere in the polymer, but separated from another Si—H moiety by about 2000 monomer units, for example, 1500, 1600, 1700, 1800, 1900, 2000, 2100, 2200, 2300, 2400, or 2500 monomer units. In a specific embodiment, on average at least two Si—H units are present anywhere in the polymer, but separated from another Si—H moiety by about 850 monomer units, for example, 350, 450, 550, 650, 750, 800, 850, 950, 1050, 1150, 1250, or 1350 monomer units. In a specific embodiment, on average greater than two Si—H units are present anywhere in the polymer, but separated from another Si—H moiety by about 40 monomer units, for example, 5, 10, 15, 20, 25, 30, 35, 40, 45, 50, 55, 60, 65, 70, 75, or 80 monomer units.

In one aspect of any one of the above embodiments, the sum of s and t is an integer from about 1000 to about 8000; from about 1300 to about 2700; from about 1500 to about 2700; from about 1600 to about 2600; from about 1600 to about 2500; from about 1700 to about 2500; from about 1800 to about 2400; from about 1800 to about 2300; from about 1900 to about 2300; from about 2000 to about 2200; from about 2050 to about 2150; from about 2100.

In one aspect of any one of the above embodiments, the sum of s and t is an integer from about 200 to about 1100; from about 600 to about 1100; from about 700 to about 1000; from about 800 to about 900; from about 825 to about 875; from about 850; from about 200 to about 800; from about 225 to about 700; from about 250 to about 600; from about 275 to about 500; from about 300 to about 400; from about 350 to about 400; from about 375. In a specific embodiment, the sum of s and t is an integer from about 850.

In one aspect of any one of the above embodiments, the sum of s and t is an integer from about 5 to about 1300; from about 10 to about 1100; from about 10 to about 600; from about 15 to about 500; from about 15 to about 400; from about 20 to about 300; from about 20 to about 200; from about 25 to about 100; from about 25 to about 75; from about 30 to about 50; from about 40.

In some embodiments, the reactive constituent comprises at least one organopolysiloxane. The term "organopolysiloxane" includes compounds of formula II:

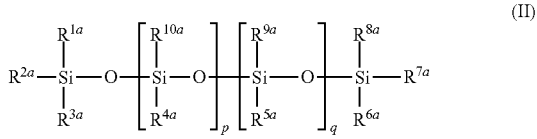

wherein $R^{1a}$, $R^{2a}$, $R^{3a}$, $R^{4a}$, $R^{5a}$, $R^{6a}$, $R^{7a}$, $R^{8a}$, $R^{9a}$ and $R^{10a}$ are each independently selected from hydrogen, $C_{1-20}$ alkyl, $C_{2-20}$ alkenyl, $C_{5-10}$ aryl, hydroxyl or $C_{1-20}$ alkoxyl and p and q are each independently an integer from between 10 and about 6000.

In some embodiments, the organopolysiloxane is a compound of formula IIa:

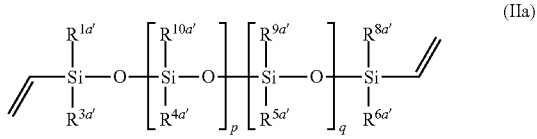

wherein $R^{1a'}$, $R^{3a'}$, $R^{4a'}$, $R^{5a'}$, $R^{6a'}$, $R^{8a'}$, $R^{9a'}$ and $R^{10a'}$ are each independently selected from hydrogen, $C_{1-20}$ alkyl, $C_{2-20}$ alkenyl, $C_{5-10}$ aryl, hydroxyl or $C_{1-20}$ alkoxyl and p and q are each independently an integer from between 10 and about 6000. In one embodiment, $R^{1a'}$, $R^{3a'}$, $R^{4a'}$, $R^{5a'}$, $R^{6a'}$, $R^{8a'}$, $R^{9a'}$ and $R^{10a'}$ are alkyl (e.g., $C_1$ alkyl, such as methyl).

The term "alkyl" includes both branched and straight-chain saturated aliphatic hydrocarbon groups having the specified number of carbon atoms. The term "$C_{1-20}$ alkyl" includes branched and straight chain aliphatic groups having between 1 and 20 carbons. Examples of alkyl moieties include methyl, ethyl, n-propyl, i-propyl, n-butyl, s-butyl, t-butyl, n-pentyl, n-hexyl, isopropyl, isobutyl, sec-butyl, tert-butyl, isopentyl, and s-pentyl. Moreover, the term alkyl includes both "unsubstituted alkyls" and "substituted alkyls," the latter of which refers to alkyl moieties having substituents (e.g., F, Cl, Br, I, $NO_2$, CN, alkyl, aryl, hydroxyl, alkoxy, $COCH_3$ and the like) replacing a hydrogen on one or more carbons of the hydrocarbon backbone.

The term "alkenyl" includes the specified number of hydrocarbon atoms in either straight or branched configuration with one or more unsaturated carbon-carbon bonds that may occur in any stable point along the chain, such as ethenyl and propenyl. The language "$C_{2-20}$ alkenyl" includes branched and straight chain hydrocarbon groups with between 1 and 20 carbons and with one or more unsaturated carbon-carbon bonds. Moreover, the term "alkenyl" includes both "unsubstituted alkenyls" and "substituted alkenyls," the latter of which refers to alkenyl moieties having substituents (e.g., F, Cl, Br, I, $NO_2$, CN, alkyl, aryl, hydroxyl, alkoxy, $COCH_3$ and the like) replacing a hydrogen on one or more carbons of the hydrocarbon backbone.

The term "aryl" includes 5-10 membered monocyclic, bicyclic, or tricyclic rings, wherein at least one ring, if more than one is present, is aromatic. The term "aryl" also includes "heteraryl" moieties in which one heteroatom (e.g., N, O or S) replaces one or more carbons in the monocyclic, bicyclic, or tricyclic ring. The term "aryl" also includes both "unsubstituted aryls" and "substituted aryls," the latter of which refers to aryl moieties having substituents (e.g., F, Cl, Br, I, $NO_2$, CN, alkyl, hydroxyl, alkoxy, $COCH_3$ and the like) replacing a hydrogen on one or more carbons aromatic ring.

The term "hydroxyl" includes —OH.

The term "alkoxy" includes moieties in which an O is covalently bonded to a $C_{1-20}$ alkyl group, as defined above.

In some embodiments, the organopolysiloxane is vinyl terminated. The language "vinyl terminated organopolysiloxane" includes organopolysiloxanes of formula II in which one or both of $R^{2a}$ and $R^{7a}$ are substituted with a $C_2$ alkyl moiety, for example, a vinyl moiety (e.g., —CH=$CH_2$). In a specific embodiment, a "vinyl terminated organopolysiloxane" includes organopolysiloxanes of formula II in which one or both of $R^{2a}$ and $R^{7a}$ are substituted with a $C_2$ alkyl moiety, for example, a vinyl moiety (e.g., —CH=$CH_2$), and $R^{1a}$, $R^{3a}$, $R^{4a}$, $R^{5a}$, $R^{6a}$, $R^{8a}$, $R^{9a}$ and $R^{10a}$ are independently selected from $C_{1-20}$ alkyl, for example, methyl.

In other embodiments, the organopolysiloxane is selected from: vinyl terminated polydimethylsiloxane; vinyl terminated diphenylsiloxane-dimethylsiloxane copolymers; vinyl terminated polyphenylmethylsiloxane, vinylphenylmethyl terminated vinylphenylsiloxane-phenylmethylsiloxane copolymer; vinyl terminated trifluoropropylmethylsiloxane-dimethylsiloxane copolymer; vinyl terminated diethylsiloxane-dimethylsiloxane copolymer; vinylmethylsiloxane-dimethylsiloxane copolymer, trimethylsiloxy terminated; vinylmethylsiloxane-dimethylsiloxane copolymers, silanol terminated; vinylmethylsiloxane-dimethylsiloxane copolymers, vinyl terminated; vinyl gums; vinylmethylsiloxane homopolymers; vinyl T-structure polymers; monovinyl terminated polydimethylsiloxanes; vinylmethylsiloxane terpolymers; vinylmethoxysilane homopolymers and combinations thereof.

In some embodiments, the organopolysiloxane is a high viscosity organopolysiloxane, a low viscosity organopolysiloxane or a combination thereof.

When the organopolysiloxane is a combination of high and low viscosity organopolysiloxanes, the combination of a high viscosity and a low viscosity vinyl organosiloxane provides a bimodal distribution of organosiloxane molecular weights. In at least one embodiment, the organopolysiloxane is a combination of high and low viscosity vinyl-terminal organopolysiloxanes providing a bimodal distribution of the vinyl-terminated organopolysiloxane. In one embodiment, the organopolysiloxane is a combination of formulas I, II, IIa, IIb, and IIc, specifically, of formula IIa, IIb and/or IIc, or more specifically, of formula IIb and IIc, providing a bimodal distribution of the vinyl-terminated organopolysiloxane. In one embodiment, the bimodal distribution of polymer molecular weight is represented by a ratio of the molecular weights (for example, the sum of s and t) of the high viscosity organopolysiloxanes to the low viscosity organopolysiloxane. In one embodiment, this ratio is from 2 to 3. In a specific embodiment, this ratio is 2.5.

The term "viscosity" refers to the measure of the resistance of a fluid which is being deformed by either shear stress or tensile stress. One of skill in the art without undue experimentation would be able to determine how to measure the viscosity of a fluid, for example, using a viscometer or a rheometer. Representative methods include use of a capillary viscometer, rotational viscometer or rheometer to measure viscosity at an instrument specific strain. Specific methods for determining the viscosity of a fluid are shown in Example 6.

The language "high viscosity organopolysiloxane" includes organopolysiloxanes with a viscosity of between about 100,000 and about 500,000 cSt or cP at 25° C., for example, between about 110,000 and about 450,000 cSt or cP at 25° C., between about 120,000 and about 400,000 cSt or cP at 25° C., between about 125,000 and about 350,000 cSt or cP at 25° C., between about 130,000 and about 300,000 cSt or cP at 25° C., between about 135,000 and about 250,000 cSt or cP at 25° C., between about 140,000 and about 200,000 cSt or cP at 25° C., between about 145,000 and about 190,000 cSt or cP at 25° C., between about 150,000 and about 185,000 cSt or cP at 25° C., between about 155,000 and about 175,000 cSt or cP at 25° C., or between about 160,000 and about 170,000 cSt or cP at 25° C. In some embodiments, the viscosity of the high viscosity organopolysiloxane is between about 140,000 and about 200,000 cSt or cP at 25° C. In one embodiment, the high viscosity organopolysiloxane has a viscosity of about 165,000 cSt or cP at 25° C.

In one embodiment, the average molecular weight of the high viscosity organopolysiloxane is between about 100,000 and about 200,000 Da, for example, between about 115,000 and about 195,000 Da, between about 120,000 and about 190,000 Da, between about 125,000 and about 185,000 Da, between about 130,000 and about 180,000 Da, between about 135,000 and about 175,000 Da, between about 140,000 and about 170,000 Da, between about 145,000 and about 165,000 Da or between about 150,000 and about 160,000 Da. In one embodiment, the average molecular weight of the high viscosity organopolysiloxane is about 155,000 Da.

In some embodiments, the high viscosity organopolysiloxane is of formula II, in which $R^{2a}$ and $R^{7a}$ are $C_{2-20}$ alkenyl, for example, $C_2$ alkenyl (e.g., vinyl) and $R^{1a}$, $R^{3a}$, $R^{4a}$, $R^{5a}$, $R^{6a}$, $R^{8a}$, $R^{9a}$ and $R^{10a}$ are each $C_{1-20}$ alkyl, for example, $C_1$ alkyl (e.g., methyl).

In some embodiments, the high viscosity organopolysiloxane is vinyl terminated. In other embodiments, the high viscosity organopolysiloxane is vinyl terminated polydimethylsiloxane.

In some embodiments, the vinyl terminated high viscosity organopolysiloxane has a weight percent of vinyl of between about 0.010 and about 0.100, for example, between about 0.015 and about 0.080, between about 0.020 and about 0.075, between about 0.025 and about 0.060, or between about 0.030 and about 0.050. In one embodiment, the high viscosity organopolysiloxane has a weight percent of vinyl of between about 0.030 and about 0.040.

In other embodiments, the high viscosity organopolysiloxane has a vinyl equivalent per kilogram of between about 0.0100 and about 0.0200, for example, between about 0.0110 and about 0.0190, between about 0.0115 and about 0.0180, between about 0.0120 and about 0.0170, between about 0.0125 and about 0.0165 or between about 0.013 and about 0.016.

In one embodiment, the high viscosity organopolysiloxane has on average at least two vinyl units per high viscosity organopolysiloxane. In one embodiment, the monomer unit including a vinyl moiety are spaced throughout the polymer. In one embodiment, the vinyl-containing monomer unit is spaced about 2000 monomer units away from another vinyl-containing monomer unit or a vinyl-containing terminal cap. For example, the vinyl units in the high viscosity organopolysiloxanes are separated by 1500, 1600, 1700, 1800, 1900, 2000, 2100, 2200, 2300, 2400, or 2500 monomer units.

In some embodiments, the high viscosity organopolysiloxane is selected from: vinyl terminated polydimethylsiloxane; vinyl terminated diphenylsiloxane-dimethylsiloxane copolymers; vinyl terminated polyphenylmethylsiloxane, vinylphenylmethyl terminated vinylphenylsiloxane-phenylmethylsiloxane copolymer; vinyl terminated trifluoropropylmethylsiloxane-dimethylsiloxane copolymer; vinyl terminated diethylsiloxane-dimethylsiloxane copolymer; vinylmethylsiloxane-dimethylsiloxane copolymer, trimethylsiloxy terminated; vinylmethylsiloxane-dimethylsiloxane copolymers, silanol terminated; vinylmethylsiloxane-dimethylsiloxane copolymers, vinyl terminated; vinyl gums; vinylmethylsiloxane homopolymers; vinyl T-structure polymers; monovinyl terminated polydimethylsiloxanes; vinylmethylsiloxane terpolymers; vinylmethoxysilane homopolymers and combinations thereof.

The language "low viscosity organopolysiloxane" includes organopolysiloxanes with a viscosity of between about 500 and about 50,000 cSt or cP at 25° C., for example, between about 1,000 and about 45,000 cSt or cP at 25° C., between about 1,500 and about 40,000 cSt or cP at 25° C., between about 2,000 and about 35,000 cSt or cP at 25° C., between about 2,500 and about 30,000 cSt or cP at 25° C., between about 3,000 and about 25,000 cSt or cP at 25° C., between about 3,500 and about 20,000 cSt or cP at 25° C., between about 4,000 and about 15,000 cSt or cP at 25° C., or between about 4,000 and about 12,000 cSt or cP at 25° C. In some embodiments, the low viscosity organopolysiloxane includes organopolysiloxanes with a viscosity of between about 100 and about 5,000 cSt or cP at 25° C., for example, between about 200 and about 4000 cSt or cP at 25° C., between about 300 and about 3000 cSt or cP at 25° C., between about 400 and about 2000 cSt or cP at 25° C. or between about 750 and about 1500 cSt or cP at 25° C. In one embodiment, the low viscosity organopolysiloxane has a viscosity of about 10,000 cSt or cP at 25° C. In some embodiments, the low viscosity organopolysiloxane has a viscosity of about 1000 cSt or cP at 25° C.

In some embodiments, the low viscosity organopolysiloxane has an average molecular weight of between about 20,000 and about 80,000 Da, for example, between about 50,000 and about 75,000 Da, between about 55,000 and about 70,000 Da, between about 60,000 and about 65,000 Da or between 62,000 and about 63,000 Da. In one embodiment, the low viscosity organopolysiloxane has an average molecular weight of about 62,700 Da. In one embodiment, the low viscosity organopolysiloxane has an average molecular weight of about 28,000 Da.

In some embodiments, the low viscosity organopolysiloxane is of formula II, in which $R^{2a}$ and $R^{7a}$ are $C_{2-20}$ alkenyl, for example, $C_2$ alkenyl (e.g., vinyl) and $R^{1a}$, $R^{3a}$, $R^{4a}$, $R^{5a}$, $R^{6a}$, $R^{8a}$, $R^{9a}$ and $R^{10a}$ are each $C_{1-20}$ alkyl, for example, $C_1$ alkyl (e.g., methyl).

In some embodiments, the low viscosity organopolysiloxane is vinyl terminated. In other embodiments, the low viscosity organopolysiloxane is vinyl terminated polydimethylsiloxane.

In some embodiments, the low viscosity organopolysiloxane has a weight percent of vinyl of between about 0.010 and about 0.30, for example, between about 0.020 and about 0.29, between about 0.030 and about 0.28, between about 0.040 and about 0.27, between about 0.050 and about 0.26, between about 0.060 between about 0.25, between about 0.070 and about 0.24, between about 0.080 and about 0.23, or between about 0.090 and about 0.22. In some embodiments, the low viscosity organopolysiloxane has a weight percent of vinyl of between about 0.18 and about 0.26.

In other embodiments, the low viscosity organopolysiloxane has a vinyl equivalent per kilogram of between about 0.010 and about 0.100, for example, between about 0.015 and about 0.090, between about 0.020 and about 0.080, between about 0.025 and about 0.070, between about 0.030 and about 0.060 or between about 0.040 and about 0.050. In some embodiments, the low viscosity organopolysiloxane has a vinyl equivalent per kilogram of between about 0.030 and about 0.040.

In other embodiments, the low viscosity organopolysiloxane has on average at least two vinyl units per low viscosity organpolysiloxane. In one embodiment, the monomer unit including a vinyl moiety are spaced throughout the polymer. In one embodiment, the vinyl-containing monomer unit is spaced about 850 monomer units away from another vinyl-containing monomer unit or a vinyl-containing terminal cap. For example, the vinyl units in the low viscosity organopolysiloxanes are separated by 450, 550, 650, 750, 800, 850, 950, 1050, 1150, 1250, or 1350 monomer units.

In some embodiments, the low viscosity organopolysiloxane is selected from: vinyl terminated polydimethylsiloxane; vinyl terminated diphenylsiloxane-dimethylsiloxane copolymers; vinyl terminated polyphenylmethylsiloxane, vinylphenylmethyl terminated vinylphenylsiloxane-phenylmethylsiloxane copolymer; vinyl terminated trifluoropropylmethylsiloxane-dimethylsiloxane copolymer; vinyl terminated diethylsiloxne-dimethylsiloxane copolymer; vinylmethylsiloxane-dimethylsiloxane copolymer, trimethylsiloxy terminated; vinylmethylsiloxane-dimethylsiloxane copolymers, silanol terminated; vinylmethylsiloxane-dimethylsiloxane copolymers, vinyl terminated; vinyl gums; vinylmethylsiloxane homopolymers; vinyl T-structure polymers; monovinyl terminated polydimethylsiloxanes; vinylmethylsiloxane terpolymers; vinylmethoxysilane homopolymers and combinations thereof.

In some embodiments, the organopolysiloxane is a compound of formula IIb:

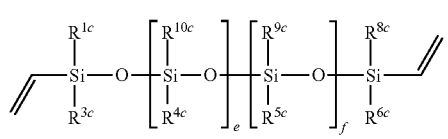

wherein $R^{1c}$, $R^{3c}$, $R^{4c}$, $R^{5c}$, $R^{6c}$, $R^{8c}$, $R^{9c}$ and $R^{10c}$ are each independently selected from hydrogen, $C_{1-20}$ alkyl, $C_{2-20}$ alkenyl, $C_{5-10}$ aryl, hydroxyl or $C_{1-20}$ alkoxyl and e and f are each independently an integer from between 10 and about 6000. In one embodiment, $R^{1c}$, $R^{3c}$, $R^{4c}$, $R^{5c}$, $R^{6c}$, $R^{8c}$, $R^{9c}$ and $R^{10c}$ are alkyl (e.g., $C_1$ alkyl, such as methyl). In some embodiments, the sum of e and f is an integer from about 1000 to about 8000; from about 1300 to about 2700; from about 1500 to about 2700; from about 1600 to about 2600; from about 1600 to about 2500; from about 1700 to about 2500; from about 1800 to about 2400; from about 1800 to about 2300; from about 1900 to about 2300; from about 2000 to about 2200; from about 2050 to about 2150; from about 2100.

In some embodiments, the organopolysiloxane is a compound of formula IIc:

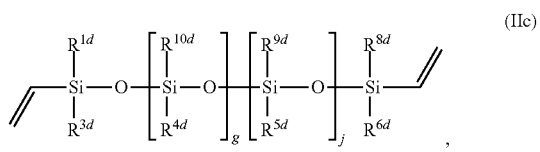

wherein $R^{1d}$, $R^{3d}$, $R^{4d}$, $R^{5d}$, $R^{6d}$, $R^{8d}$, $R^{9d}$ and $R^{10d}$ are each independently selected from hydrogen, $C_{1-20}$ alkyl, $C_{2-20}$ alkenyl, $C_{5-10}$ aryl, hydroxyl or $C_{1-20}$ alkoxyl and g and j are each independently an integer from between 10 and about 6000. In one embodiment, $R^{1d}$, $R^{3d}$, $R^{4d}$, $R^{5d}$, $R^{6d}$, $R^{8d}$, $R^{9d}$ and $R^{10d}$ are alkyl (e.g., $C_1$ alkyl, such as methyl). In some embodiments, the sum of g and j is an integer from about 200 to about 1100; from about 600 to about 1100; from about 700 to about 1000; from about 800 to about 900; from about 825 to about 875; from about 850; from about 200 to about 800; from about 225 to about 700; from about 250 to about 600; from about 275 to about 500; from about 300 to about 400; from about 350 to about 400; from about 375. In some embodiments, the sum of g and j is an integer from about 850.

In some embodiments, the reactive constituent comprises at least one hydride functionalized polysiloxane. The language "hydride functionalized polysiloxane" includes compounds of formula III:

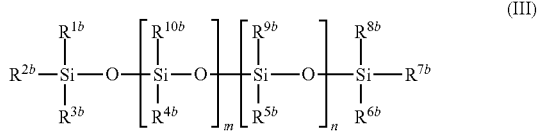

wherein $R^{1b}$, $R^{2b}$, $R^{3b}$, $R^{4b}$, $R^{5b}$, $R^{6b}$, $R^{7b}$, $R^{8b}$, $R^{9b}$ and $R^{10b}$ are each independently selected from hydrogen, $C_{1-20}$ alkyl, $C_{2-20}$ alkenyl, $C_{5-10}$ aryl, hydroxyl or $C_{1-20}$ alkoxy and m and n are each independently an integer from between 10 and about 6000, provided that at least one of $R^{1b}$, $R^{2b}$, $R^{3b}$, $R^{4b}$, $R^{5b}$, $R^{6b}$, $R^{7b}$, $R^{8b}$, $R^{9b}$ and $R^{10b}$ is hydrogen. In some embodiments, at least one of $R^{1b}$, $R^{2b}$, $R^{3b}$, $R^{4b}$, $R^{5b}$, $R^{6b}$, $R^{7b}$, $R^{8b}$, $R^{9b}$ and $R^{10b}$ is hydrogen and the remainder are $C_{1-20}$ alkyl. In some embodiments, at least two of $R^{1b}$, $R^{2b}$, $R^{3b}$, $R^{4b}$, $R^{5b}$, $R^{6b}$, $R^{7b}$, $R^{8b}$, $R^{9b}$ and $R^{10b}$ are hydrogen (e.g., two Si—H units per functionalized hydride polysiloxane molecule). In other embodiments, at least three of $R^{1b}$, $R^{2b}$, $R^{3b}$, $R^{4b}$, $R^{5b}$, $R^{6b}$, $R^{7b}$, $R^{8b}$, $R^{9b}$ and $R^{10b}$ are hydrogen (e.g., three Si—H units per functionalized hydride polysiloxane molecule). In some embodiments, at least two of $R^{1b}$, $R^{2b}$, $R^{3b}$, $R^{4b}$, $R^{5b}$, $R^{6b}$, $R^{7b}$, $R^{8b}$, $R^{9b}$ and $R^{10b}$ are hydrogen (e.g., two Si—H units per functionalized hydride polysiloxane molecule) and the remainder are $C_{1-20}$ alkyl. In other embodiments, at least three of $R^{1b}$, $R^{2b}$, $R^{3b}$, $R^{4b}$, $R^{5b}$, $R^{6b}$, $R^{7b}$, $R^{8b}$, $R^{9b}$ and $R^{10b}$ are hydrogen (e.g., three Si—H units per functionalized hydride polysiloxane molecule) and the remainder are $C_{1-20}$ alkyl. In some embodiments, at least two of $R^{4b}$, $R^{5b}$, $R^{9b}$ and $R^{10b}$ are hydrogen (e.g., two Si—H units per functionalized hydride polysiloxane molecule) and the remainder are $C_{1-20}$ alkyl. In other embodiments, at least three of $R^{4b}$, $R^{5b}$, $R^{9b}$ and $R^{10b}$ are hydrogen (e.g., three Si—H units per functionalized hydride polysiloxane molecule) and the remainder are $C_{1-20}$ alkyl.

In one embodiment, at least greater than two monomer units of formula III include a —Si—H unit (e.g. one or more of $R^{11}$, $R^{12}$, $R^{18}$, and $R^{19}$ is hydrogen). For example, on average 2 to 15 monomer units of formula III include a Si—H unit. In one embodiment, at least two monomer units of formula III include a —Si—H unit (e.g. one or more of $R^{11}$, $R^{12}$, $R^{18}$, and $R^{19}$ is hydrogen). In one embodiment, at least three monomer units of formula III include a —Si—H unit (e.g. one or more of $R^{11}$, $R^{12}$, $R^{18}$ and $R^{19}$ is hydrogen). In one embodiment, at least four monomer units of formula III include a —Si—H unit (e.g. one or more of $R^{11}$, $R^{12}$, $R^{18}$ and $R^{19}$ is hydrogen). In one embodiment, at least five monomer units of formula III include a —Si—H unit (e.g. one or more of $R^{11}$, $R^{12}$, $R^{18}$, and $R^{19}$ is hydrogen). In one embodiment, at least six monomer units of formula III include a —Si—H unit (e.g. one or more of $R^{11}$, $R^{12}$, $R^{18}$, and $R^{19}$ is hydrogen). In one embodiment, at least seven monomer units of formula III include a —Si—H unit (e.g. one or more of $R^{11}$, $R^{12}$, $R^{18}$ and $R^{19}$ is hydrogen). In one embodiment, at least eight monomer units of formula III include a —Si—H unit (e.g. one or more of $R^{11}$, $R^{12}$, $R^{18}$, and $R^{19}$ is hydrogen). In a specific embodiment, the non Si—H positions may include a Si-(alkyl) or Si-(vinyl) unit. In a specific embodiment, the non-Si—H positions are Si—CH₃. In one embodiment, the Si—H units in the hydride-functionalized organopolysiloxanes are separated by 5, 10, 15, 20, 25, 30, 35, 40, 45, 50, 60, 65, 70, 75, 80, 85, 90, 100, 125, 150, or 200 monomer units.

In one aspect of any one of the above embodiments, the sum of m and n is an integer from about 10 to about 1300; from about 10 to about 1100; from about 10 to about 600; from about 15 to about 500; from about 15 to about 400; from about 20 to about 300; from about 20 to about 200; from about 25 to about 100; from about 25 to about 75; from about 30 to about 50; from about 40.

In some embodiments, the hydride functionalized polysiloxane includes Si—H units only at the terminal caps of the polymer. In some embodiments, the polysiloxane include Si—H units only in the monomer units, but not at the terminal cap of the polymer. In other embodiments, the polysiloxane includes Si—H units at both the terminal cap or in the monomer unit of the polymer. In one embodiment, the polysiloxane includes two to twelve Si—H units located either at the terminal cap, or within the monomer unit, or a combination thereof. In one embodiment, the polysiloxane includes four to fifteen Si—H units located either at the terminal cap, or within the monomer unit, or a combination thereof. In one embodiment, the polysiloxane includes eight Si—H units located either at the terminal cap, or within the monomer unit, or a combination thereof.

In some embodiments, the hydride functionalized polysiloxane has a viscosity of between about 5 and about 11,000 cSt or cP at 25° C., for example, between about 10 and about 10,000 cSt or cP at 25° C., between about 15 and about 5,000 cSt or cP at 25° C., between about 20 and about 1,000 cSt or cP at 25° C., between about 25 and about 500 cSt or cP at 25° C., between about 30 and about 100 cSt or cP at 25° C., and between about 40 and about 50 cSt or cP at 25° C. In one embodiment, the hydride functionalized polysiloxane has a viscosity of about 45 cSt or cP at 25° C.

In some embodiments, the hydride functionalized polysiloxane has an average molecular weight of between about 900 and about 60,000 Da, for example, between about 1000 and about 50,000 Da, between about 1200 and about 25,000 Da, between about 1400 and about 20,000 Da, between about 1600 and about 15,000 Da, between about 1800 and about 10,000 Da, between about 2000 and about 5000 Da, between about 2200 and about 4000 Da, and between 2300 and about 2500 Da. In one embodiment, the average molecular weight of the hydride functionalized polysiloxane is about 2400 Da.

In some embodiments, the hydride functionalized polysiloxane has a percent SiH content of between about 3 and about 45%, for example, between about 5 and about 40%, between about 10 and about 35%, between about 20 and about 30%, or between about 26 and about 27%. In some embodiments, the hydride functionalized polysiloxane has a percent SiH content of about 26%.

In some embodiments, the hydride functionalized polysiloxane has an SiH content of between about 0.500 mmol/g and about 10.00 mmol/g, for example, between about 1.00 mmol/g and about 9.00 mmol/g, between about 2.00 and about 8.00 mmol/g, between about 3.00 mmol/g and about 7.00 mmol/g, and about 4.00 mmol/g and about 6.00 mmol/g. In one embodiment, the hydride functionalized polysiloxane has an SiH content of between about 4.00 and about 5.00 mmol/g, for example, 4.35 mmol/g.

In other embodiments, the hydride functionalized polysiloxane is alkyl terminated. The language "alkyl terminated" includes hydride functionalized polysiloxanes of formula III in which one or both of $R^{2b}$ and $R^{7b}$ are $C_{1-20}$ alkyl. In some embodiments, "alkyl terminated" includes hydride functionalized polysiloxanes of formula III in which one, two, three, four, five or six of $R^{1b}$, $R^{2b}$, $R^{3b}$, $R^{6b}$, $R^{7b}$ and $R^{8b}$ are $C_{1-20}$ alkyl. In one embodiment, $R^{1b}$, $R^{2b}$, $R^{3b}$, $R^{4b}$, $R^{5b}$, $R^{6b}$, $R^{7b}$, $R^{8b}$ and $R^{10b}$ are each $C_{1-20}$ alkyl, for example, $C_1$ alkyl (e.g., methyl) and $R^{9b}$ is hydrogen. In one embodiment, $R^{1b}$, $R^{2b}$, $R^{3b}$, $R^{4b}$, $R^{5b}$, $R^{6b}$, $R^{7b}$, $R^{8b}$ and $R^{9b}$ are each $C_{1-20}$ alkyl, for example, $C_1$ alkyl (e.g., methyl) and $R^{10b}$ is hydrogen.

In some embodiments, the hydride functionalized polysiloxane is selected from the group consisting of hydride terminated polydimethylsiloxane; polyphenyl-(dimethylhydrosiloxy)siloxane, hydride terminated; methylhydrosiloxane-phenylmethylsiloxane copolymer, hydride terminated; methylhydrosiloxane-dimethylsiloxane copolymers, trimethylsiloxy terminated; polymethylhydrosiloxanes, trimethylsiloxy terminated; polyethylhydrosiloxane, triethylsiloxane, methylhydrosiloxane-phenyloctylmethylsiloxane copolymer; methylhydrosiloxane-phenyloctylmethylsiloxane terpolymer and combinations thereof.

In some embodiments, the reactive constituent comprises combinations of polymers of formulas I, II, IIa, IIb, IIc, IId, and/or III. In a specific embodiment, the reactive constituent comprises a combination of polymers of formulas IIa, IIb, IIc and/or III. In a specific embodiment, the reactive constituent comprises a combination of polymers of formulas IIb, IIc and III.

In some embodiments, the reactive constituent comprises combinations of high molecular weight vinyl organopolysiloxanes, low molecular weight vinyl organopolysiloxanes, and/or hydride-functionalized organopolysiloxanes. In one embodiment, each of the high and low molecular weight organopolysiloxanes includes on average at least two vinyl moieties per polymer. In a specific embodiment, each vinyl organopolysiloxane includes exactly two vinyl moieties. In one embodiment, the ratio of the high molecular organopolysiloxane to the low molecular weight organopolysiloxane is 2 to 3, for example 2, 2.5 or 3. The ratio may be selected in order to adjust the chemical and physical properties of the film in order to suit a specific method or part of the body. In one embodiment, the hydride-functionalized organopolymer includes on average greater than two Si—H units in the polymer. In a specific embodiment, there are 8 Si—H units per hydride-functionalized organopolysiloxane.

In some embodiments, the reactive constituent comprises combinations of high molecular weight hydride-functionalized organopolysiloxanes, low molecular weight hydride functionalized organopolysiloxanes, and/or vinyl organopolysiloxanes. In one embodiment, each of the high and low molecular weight organopolysiloxanes include on average at least two Si—H units per polymer. In a specific embodiment, each hydride-functionalized organopolysiloxane includes exactly two Si—H moieties. In one embodiment, the ratio of the high molecular organopolysiloxane to the low molecular weight organopolysiloxane is 2 to 3, for example 2, 2.5 or 3. The ratio may be selected in order to adjust the chemical and physical properties of the film in order to suit a specific method or part of the body. In one embodiment, the vinyl organopolymer includes on average greater than at least two vinyl units in the polymer. In a specific embodiment, there are 8 vinyl units per vinyl organopolysiloxane.

The language "reinforcing constituent" includes one or more constituents of the reactive reinforcing component that provide the required physical properties of the film that results from the in situ reaction between the reactive reinforcing component and the cross-linking component. Such physical properties include, for example, mechanical elements (e.g., elasticity, durability, fracture strain, tensile strength, etc. . . . ), biocompatibility (e.g., selective breathability, adhesion, etc. . . . ), optical effects (e.g., reflectance, color, etc. . . . ) and surface modulation (e.g., texture, chemistry, etc. . . . ). Examples of reinforcing constituents include clays, (e.g., $Al_2O_3$, $SiO_2$), chalk, talc, calcite (e.g., $CaCO_3$), mica, barium sulfate, zirconium dioxide, zinc sulfide, zinc oxide, titanium dioxide, aluminum oxide, silica aluminates, calcium silicates, or optionally surface treated silica (e.g., fumed silica, hydrated silica or anhydrous silica). In some embodiments, reinforcing constituent is silica, for example, surface treated silica, such as silica treated with hexamethyldisilazane.

In some embodiments, the reinforcing constituent has a surface area of between about 100 and about 300 $m^2/g$, for example, between about 110 and about 250 $m^2/g$, between about 120 and about 225 $m^2/g$, between about 130 and about 200 $m^2/g$, between about 135 and about 185 $m^2/g$, between about 160 and about 170 $m^2/g$, and between about 164 and about 166 $m^2/g$. In one embodiment, the reinforcing constituent has a surface area of about 160±25 $m^2/g$.

In some embodiments, the reinforcing constituent has an average particle size of between about 1 and about 20 μm.

In some embodiments, the reinforcing constituent is compounded with the low viscosity and/or the high viscosity organopolysiloxane.

In some embodiments, reactive constituent and reinforcing constituent comprise between about 20 and about 90% of the reactive reinforcing component, for example, between about 40% and about 60% of the reactive reinforcing component. In some embodiments, the reactive constituent and reinforcing constituent comprise between about 45.0 and about 61.0% of the reactive reinforcing component, for example, about 45.0%, about 45.5%, about 46.0%, about 46.5%, about 47.0%, about 47.5%, about 48.5%, about 49.0%, about 49.5%, about 50.0%, about 50.5%, about 51.0%, about 51.5%, about 52.0%, about 52.5%, about 53.0%, about 53.5%, about 54.0%, about 54.5%, about 55.0%, about 55.5%, about 56.0%, about 56.5%, about 57.0%, about 58.0%, about 58.5%, about 59.0%, about 59.5%, about 60.0%, or about 60.5%. In some embodiments, the reactive constituent and the reinforcing constituent comprise about 45% of the reactive reinforcing component. In one embodiment, the reactive constituent and reinforcing constituent comprise about 48.0% of the reactive reinforcing component. In some embodiments, the reactive constituent and the reinforcing constituent comprise about 50.0% of the reactive reinforcing component. In another embodiment, the reactive constituent and reinforcing constituent comprise about 51.0% of the reactive reinforcing component. In some embodiments, the reactive constituent and the reinforcing constituent comprise about 51.5% of the reactive reinforcing component. In another embodiment, the reactive constituent and reinforcing constituent comprise about 54.5% of the reactive reinforcing component. In another embodiment, the reactive constituent and reinforcing constituent comprise about 55.0% of the reactive reinforcing component. In some embodiments, the reactive constituent and the reinforcing constituent comprise about 59.5% of the reactive reinforcing component. In another embodiment, the reactive constituent and reinforcing constituent comprise about 60.5% of the reactive reinforcing component. In some embodiments, the reactive constituent and reinforcing constituent comprise between about 30.0 and about 40.0% of the reactive reinforcing component, for example, about 30.0%, about 30.5%, about 31.0%, about 31.5%, about 32.0%, about 32.5%, about 33.0, about 33.5%, about 34.0%, about 34.5%, about 35.0%, about 35.5%, about 36.0%, about 36.5%, about 37.0%, about 37.5%, about 38.0%, about 38.5%, about 39.0%, about 39.5%, about 40.0%. In some embodiments, the reactive constituent and reinforcing constituent comprise between about 33.0 and about 40.0% of the reactive reinforcing component In one embodiment, the reinforcing constituent comprises between about 8.0 and about 13.0% of the reactive reinforcing component, for example, about 8.5%, about 9.0%, about 9.5%, about 10.0%, about 10.5%, about 11.0%, about 11.5%, about 12.0% or about 12.5%. In some embodiments, the reinforcing constituent comprises about 8.5% of the reactive reinforcing component. In one embodiment, the reinforcing constituent comprises about 9.0% of the reactive reinforcing component. In another embodiment, the reinforcing constituent comprises about 9.5% of the reactive reinforcing component. In some embodiments, the reinforcing constituent comprises about 10.0% of the reactive reinforcing component. In some embodiments, the reinforcing constituent comprises about 10.5% of the reactive reinforcing component. In another embodiment, the reinforcing constituent comprises about 11.0% of the reactive reinforcing component. In another embodiment, the reinforcing constituent comprises about 12.0% of the reactive reinforcing component. In another embodiment, the reinforcing constituent comprises about 13.0% of the reactive reinforcing component.

In another embodiment, the reactive constituent comprises between about 30.0 and about 60.0% of the reactive reinforcing component, for example, about 30.5%, about 31.0%, about 32.0%, about 33.0%, about 34%, about 35.0%, about 36.0%, about 37.0%, about 38.0%, about 39.0%, about 40.0%, about 41.0%, about 42.0%, about 43.0%, about 44.0%, about 45.0%, about 46.0%, about 47.0%, about 48.0%, about 49.0%, about 50.0%, about 51.0%, about 52.0%, about 53.0%, about 54.0%, about 55.0%, about 56.0%, about 57.0%, about 58.0% or about 59.0%.

In some embodiments, the reactive reinforcing component has a viscosity of between about 5,000 and 1,000,000 cSt or cP at 25° C. In some embodiments, the reactive reinforcing component has a viscosity of between about 10,000 and 10,000,000 cSt or cP at 25° C., for example, about 10,000,000, about 9,000,000, about 8,000,000, about 7,000,000, about 6,000,000, about 5,000,000, about 4,000,000, about 3,000,000 or about 2,000,000, about 1,000,000, about 900,000, about 800,000, about 700,000, about 600,000, about 500,000, about 400,000, about 300,000, about 200,000, about 100,000, about 90,000, about 80,000, about 70,000, about 60,000, about 50,000, about 40,000, about 30,000, about 20,000, about 10,000 cSt. In one embodiment, the reactive reinforcing component has a viscosity of about 1,000,000 cSt.

In some embodiments, the reactive reinforcing component has a vinyl to functional hydride (e.g., —CH=CH$_2$ of the one or more organopolysiloxanes to Si—H of the hydride functionalized polysiloxane) ratio of between about 1:10 and about 1:100, for example, between about 1:15 and about 1:90, between about 1:20 and about 1:80, between about 1:25 and about 1:70, between about 1:30 and about 1:60, between about 1:35 and about 1:50. In one embodiment, the reactive reinforcing component has a vinyl to functional hydride ratio of about 1:40. In another embodiment, the reactive reinforcing component has a vinyl to functional hydride ratio of about 1:20. In some embodiments, the reactive reinforcing component has a vinyl to functional hydride ratio of about 1:15.

The language "cross-linking component" includes a component that, when applied to the reactive reinforcing component, catalyzes the in situ formation of the body corrective film.

The term "catalyzes the in situ formation of the body corrective film" includes causing a reaction to occur between the reactive constituents of the reactive reinforcing component, such that a body corrective film is formed on the skin. Without being bound by theory, the cross-linking component induces a reaction between the one or more organopolysiloxanes and the hydride functionalized polysiloxane of the reactive reinforcing component causing the condensation of these constituents, such that a film is formed upon the skin.

In some embodiments, the cross-linking component comprises a metal catalyst, for example, a platinum catalyst, a rhodium catalyst or a tin catalyst. Examples of platinum catalysts include, for example, platinum carbonyl cyclovinylmethylsiloxane complexes, platinum divinyltetramethyldisiloxane complexes, platinum cyclovinylmethylsiloxane complexes, platinum octanaldehyde/octanol complexes and combinations thereof. An example of a rhodium catalyst includes Tris (dibutylsulfide) Rhodium trichloride. Examples of tin catalysts include tin II octoate, Tin II neodecanoate, dibutyltin diisooctylmaleate, Di-n-butylbis (2,4 pentanedionate)tin, di-n-butylbutoxychlorotin, dibutyltin dilaurate, dimethyltin dineodecanoate, dimethylhydroxy (oleate)tin and tin II oleate.

In some embodiments, the cross-linking component further comprises a vinyl terminated organopolysiloxane (e.g., a compound of Formula I, II IIa, IIb or IIc). In some embodiments, the amount of vinyl-terminated polysiloxane is a stabilizing amount of vinyl-terminated polysiloxane. The language "stabilizing amount" includes an amount that prevents the degradation of the catalyst and/or the cross-linking component and/or the body corrective film. In some embodiments, the stabilizing amount of vinyl-terminated polysiloxane is less than about 50%, less than about 40%, less than about 30%, less than about 20%, less than about 10%, less than about 5% or less than about 2%. In some embodiments, the stabilizing amount of vinyl-terminated polysiloxane is about 1%.

In some embodiments, the cross-linking component has a viscosity of between about 1,000 and about 50,000 cSt or cP at 25° C.

In some embodiments, the catalyst is added as a solution and the solution comprises between about 1.0 and about 5.0% of the cross-linking component, for example, about 1.5%, about 2.0%, about 2.5%, about 3.0%, about 3.5%, about 4.0% or about 4.5%. In one embodiment, the catalyst is about 2.0% of the cross-linking component.

In some embodiments, the catalyst comprises between about 0.005 and about 0.04% of the cross-linking component, for example, about 0.005%, about 0.010%, about 0.015%, about 0.020%, about 0.025%, about 0.030% or about 0.035% or about 0.040%. In one embodiment, the catalyst is about 0.02% of the cross-linking component.

In some embodiments, the catalyst is present in the cross-linking component in an amount of between about 100 ppm and about 500 ppm.

In some embodiments, the reactive reinforcing component and the cross-linking component are prevented from coming into contact prior to use. The reactive reinforcing component and the cross-linking component can be kept from coming into contact prior to use by usual means known to one of skill in the art. In one embodiment, the skin corrective formulation is a two part formulation in which the reactive reinforcing component and said cross-linking component are packaged in separate containers and mixed prior to use. In another embodiment, the reactive reinforcing component is applied to the skin first, and the cross-linking component is applied on top of the reactive reinforcing component. In yet another embodiment, the cross-linking component is applied to the skin first and the reactive reinforcing component is applied on top of the cross-linking component. In a further embodiment, the reactive reinforcing component and the cross-linking component are packaged together in the same container with a barrier between the two components, and are mixed when the components are extracted from the container.

The term "body" includes any part of the subject's body that can benefit from the formulations disclosed herein. Examples of the subject's body include the skin, the neck, the brow, the jowls, the eyes, the hands, the feet, the face, the cheeks, the breasts, the abdomen, the buttocks, the thighs, the back, the legs, the ankles, cellulite, fat deposits, and the like.

The term "skin" includes the epidermis of the subject's skin, which is the outer layer of the skin and includes the stratified squamous epithelium composed of proliferating basal and differentiated suprabasal keratinocytes.

The term "subject" includes subjects in which the formulations disclosed herein would be appropriate for use. In one example, the subject is a mammal, for example, a human. In another embodiment, the subject is suffering from wounds, or headaches such as stress headaches.

In one embodiment, the therapeutic formulation further comprises one or more of feel modifiers, tack modifiers, spreadability enhancers, diluents, adhesion modifiers, optics modifiers, particles, volatile siloxanes, emulsifiers, emollients, surfactants, thickeners, solvents, film formers, humectants, preservatives, pigments, cosmetic agents or therapeutic agents. In other embodiments, the reactive reinforcing component and/or the cross-linking component further comprise one or more of feel modifiers, tack modifiers, spreadability enhancers, diluents, adhesion modifiers, optics modifiers, particles, volatile siloxanes, emulsifiers, emollients, surfactants, thickeners, solvents, film formers, humectants, preservatives, pigments, cosmetic agents or therapeutic agents. One of skill in the art could readily determine further appropriate additives based on the INCI dictionary, which is incorporated herein by reference in its entirety.

Examples of cosmetic or therapeutic agents include sunscreens (for example, UV protecting agents) anti-aging agents, anti-acne agents, anti-wrinkle agents, spot reducers, moisturizers, anti-oxidants, vitamins.

In some embodiments, the emulsifier is SIMULGEL™.

In some embodiments, the composition or film is administered first, followed by administration of the one or more additional cosmetic or therapeutic agents. In some embodiments, the composition or film is administered after the one or more additional cosmetic or therapeutic agents. In some embodiments, the film and the one or more additional cosmetic or therapeutic agents are administered substantially at the same time. In some embodiments, the composition or film is used to deliver the one or more additional cosmetic or therapeutic agents.

In some embodiments, a finishing formulation may be applied to the therapeutic formulation during or after formation of the film on the body. The term "finishing formulation" includes a composition comprising components that provide a desired tactile sensation or a desired aesthetic look to the film after formation. For example, the finishing formulation may provide a silky, soft and/or smooth tactile sensation or a dewy, fresh, matte, shiny or luminescent aesthetic look after application to the film.

In some embodiments, the finishing formulation comprises one or more of oils, esters or ethers, for example, triglycerides, PPG-3 benzyl ether myristate, Schercemol DISD ester, or particles, for example, nylon, silica and silicone elastomer beads. In some embodiments, the one or more of these components comprise from about 0.5% to about 100% of the finishing formulation.

In some embodiments, the finishing formulation is a cream, spray, foam, ointment, serum, gel or powder.

In some embodiments, the finishing formulation further comprises one or more f feel modifiers, tack modifiers, spreadability enhancers, diluents, adhesion modifiers, optics modifiers, particles, volatile siloxanes, emulsifiers, emollients, surfactants, thickeners, solvents, film formers, humectants, preservatives, pigments, dyes (e.g., fluorescent dyes), cosmetic agents or therapeutic agents.

In some embodiments, the films and formulations described herein comprise one or more pigments. The include natural or non-natural coloring agents or dyes. In one embodiment, the pigments are fluorescent dyes.

In some embodiments, the films and formulation further comprise a pigment dispersion formulation. The language "pigment dispersion formulation" includes a formulations that are capable of providing one or more pigments to the films or formulations as a separate component of the formulation or film. In some embodiments, the pigment dispersion formulation allows for an even distribution of the pigment in the films and formulations. In some embodiments, the pigment dispersion formulation comprises at least one reactive constituent. In some embodiments, the pigment dispersion formulation comprises at least one reinforcing constituent. In some embodiments, the pigment dispersion formulation comprises one or more of feel modifiers, tack modifiers, spreadability enhancers, diluents, adhesion modifiers, optics modifiers, particles, volatile siloxanes, emulsifiers, emollients, surfactants, thickeners, solvents, film formers, humectants, preservatives, pigments, cosmetic agents or therapeutic agents. In other embodiments, the reactive reinforcing component and/or the cross-linking component further comprise one or more of feel modifiers, tack modifiers, spreadability enhancers, diluents, adhesion modifiers, optics modifiers, particles, volatile siloxanes, emulsifiers, emollients, surfactants, thickeners, solvents, film formers, humectants, preservatives, pigments, cosmetic agents or therapeutic agents.

In some embodiments, the pigment dispersion formulation is applied prior to or after the application of the reactive reinforcing component to the skin. In some embodiments, the pigment dispersion formulation is applied prior to or after the application of the cross-linking component to the skin. In some embodiments, the pigment dispersion formulation is applied in between the application of the reactive reinforcing component and the cross-linking component to the skin.

In some embodiments, the pigment dispersion formulation may be applied to skin that has not been subjected to the application of a therapeutic formulation or film. For example, a subject may apply the pigment dispersion formulation to the skin in the area around the therapeutic film or formulation, or the subject may apply the pigment formulation to the skin in lieu of applying the therapeutic film or formulation.

The terms "apply," "applied" and "application" includes methods to administer the formulations disclosed herein to a subject's body, such as application by fingers, brush, cotton ball, pad, spray, sponge, cotton swab, roll-on and the like. One of skill in the art can readily determine appropriate methods to apply the formulations disclosed herein.

In some embodiments, the invention pertains, at least in part, to a kit comprising a therapeutic formulation comprising a reactive reinforcing component and a cross-linking component. In some embodiments, the kit is a multi-compartment kit comprising at least two compartments in which one compartment comprises the reactive reinforcing component and the second compartment comprises the cross linking component. In some embodiments, the kit further comprises instructions for use of the kit, one or more brushes, one or more swabs, a film removing cleanser or a mirror. In some embodiments, the kit further comprises one or more finishing formulations.

In some embodiments, the invention pertains, at least in part, to a therapeutic film prepared by a process comprising the steps of applying a reactive reinforcing component to the body; and applying a cross-linking component to the reactive reinforcing component, in which the cross-linking component catalyzes an in situ cross-linking of the reactive reinforcing component.

In some embodiments, the invention pertains, at least in part, to a therapeutic film prepared by a process comprising the steps of applying a cross-linking component to the body; and applying a reactive reinforcing component to the cross-linking component, in which the cross-linking component catalyzes an in situ cross-linking of the reactive reinforcing component.

In some embodiments, the therapeutic film has an appearance of natural skin upon application to the skin. The language "appearance of natural skin" includes the perception that the therapeutic film, when applied to the skin, has the look, feel and texture of real skin and that the film treated skin has the physical properties (e.g., the elasticity and stiffness) of real (e.g., live) skin. A trained observer and/or a technician would be able to determine whether the film upon application to the body has the appearance of natural skin. For example, a trained observer would be able to determine whether the film, upon application to the body, appears excessively shiny, as described in Example 3, or whether the film appears not to move with the underlying musculature of the skin by, for example, breaking, buckling or deforming, in response to natural skin motion.

A technician would be able to determine whether the film has the appearance of natural skin upon application to the body. For example, the elasticity and stiffness of skin, with or without the therapeutic film applied to it, can be assessed by a wide variety of methods (Agache et al., *Arch. Dermatol. Rev.*, 269 (1980) 221, the teachings of which are incorporated herein by reference). For example, the DermaLab suction cup instrument provides one common method to assess the mechanical properties of skin, and has previously shown younger skin to be less stiff and more elastic than aged skin (Grahame et al. *Clinical Science* 39 (1970) 223-238, the teachings of which are incorporated herein by reference). With this method, the stiffness of the skin is indicated by the Young's Modulus, a measure calculated by the instrument based on the pressure required to suck skin up a predetermined distance.

In some embodiments, the Young's Modulus of the skin treated with a therapeutic formulation is reduced by between about 5% to about 70%, for example, between about 30% and about 60%, or between about 40% and about 50% compared to untreated skin. In some embodiments, the Young's Modulus of skin treated with a therapeutic formulation is reduced by between about 5% and about 25% compared to untreated skin.

The elasticity of the skin is determined by the skin retraction time. The retraction time is obtained by measuring the time it takes for the skin to drop a predetermined distance towards its natural position, after the suction pressure is removed. In some embodiments, the retraction time of skin treated with a therapeutic formulation is decreased by between about 5% and about 75%, for example, between about 30% and about 60%, or about 50% and about 65% when compared to untreated skin. In some embodiments, the retraction time of skin treated with a therapeutic formulation is decreased by between about 5% and about 10% compared to untreated skin. In some embodiments, the retraction time of the skin treated with the film approaches the retraction time of the film alone.

Figure 2:
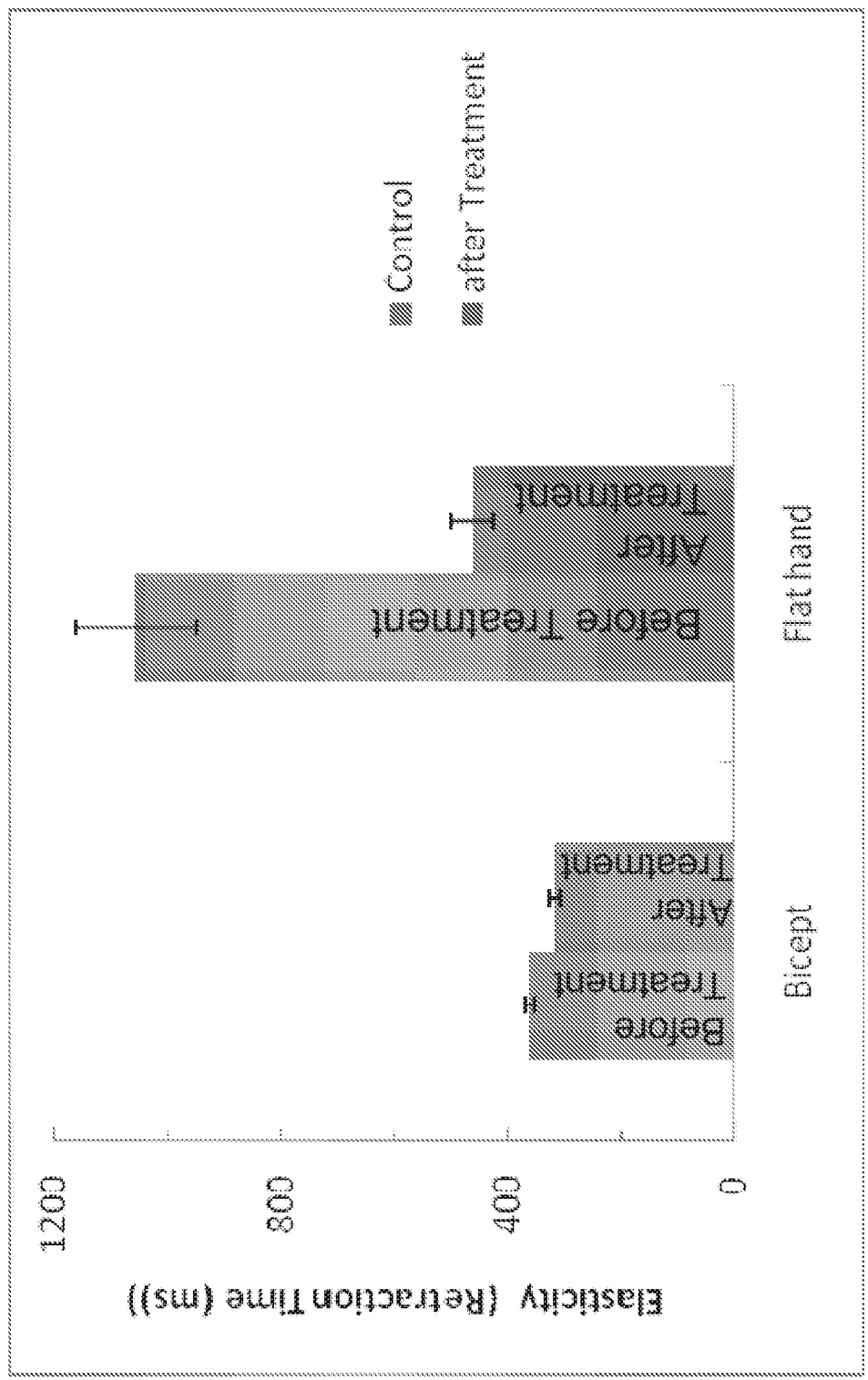
FIG. 2 is a chart illustrating the change in the retraction time after application of a formulation of the invention. The change in the retraction time indicates that the skin is more elastic upon application of the formulation.

The skin of the bicep and hand was evaluated before and after the therapeutic treatment was applied, as shown in FIGS. 1 and 2. The DermaLab results confirmed that the skin was less stiff (FIG. 1) and more elastic (FIG. 2) after product application. The observed reduction in stiffness and the increase in skin elasticity are consistent with skin being more youthful.

The language "the film is formed" and "film formation" includes the results of the polymerization reaction that occurs upon the interaction of the reactive reinforcing component and the cross-linking component. Without being bound by theory, film formation is characterized by a phase transition from the viscous sol state of a mixture to that of a continuous interconnected polymer state of film.

A technician could determine when the film is formed on the body by using routine methods. For example, rheological measurements using small amplitude oscillatory shear can determine the continuous evolution of the viscoelastic properties, such as elastic modulus (G'), the viscous modulus (G") and the loss of tangent (tan δ) of the reacting mixture continuously through the film formation process. In some embodiments, the rheometer can be used to determine the cross over time between G' and G" and the time when tan δ becomes frequency independent, which is a measure of film formation. In some embodiments, the film is formed within at least about five minutes, for example, within about one minute, about two minutes, about three minutes or about four minutes. In some embodiments, the film is formed within at least about 10 seconds and about 3 minutes.

In some embodiments, the skin or therapeutic film has a Young's Modulus (e.g., tensile strength) of between about 0.01 and about 1 MPa, as illustrated in Example 1.

In some embodiments, the fracture strain of the skin or body corrective film has a fracture strain of at least about 150%, as measured by Example 1.

In some embodiments, the therapeutic film has a leather adhesive force of greater than about 20 N/mm, for example, greater than about 25 N/mm, greater than about 30 N/mm, greater than about 35 N/mm, greater than about 40 N/mm, greater than about 45 N/mm, greater than about 50 N/mm, greater than about 55 N/mm, greater than about 60 N/mm, greater than about 65 N/mm, greater than about 70 N/mm, greater than about 75 N/mm, or greater than about 80 N/mm, as determined by the leather adhesion test illustrated in Example 2. In one embodiment, the leather adhesive force is between about 50 and about 80 N/mm, as determined by the leather adhesion test illustrated in Example 2.

In some embodiments, the therapeutic film has a hysteresis of less than about 10% for example, least than about 9%, less than about 8%, less than about 7%, less than about 6%, less than about 5%, less than about 4%, less than about 3%, less than about 2%, less than 1% or about 0%.

In some embodiments, the therapeutic film is between about 10 μm and about 1500 μm thick, for example, between about 50 μm and about 500 μm thick. In some embodiments, the film is less than about 100 μm thick. The film thickness may be measured by methods known to one of skill in the art, for example, by the combination of calipers and a calibrated microscope. The thickness of the film may also be digitally measured from a micrograph of the film cross-section. The microscope calibration allows for the conversion of measured pixelar distance into metric distance units.

In some embodiments, the therapeutic film shrinks by less than between about 1 and 30%, for example, between about 1 to about 15%. The amount of shrinking may be determined by methods known to one of skill in the art, for example, by the Croll method (Croll, S. G. *J. Coatings Tech.* 52 (1980) 35, the teachings of which are incorporated herein by reference). In this method the film is used to coat one side of a thin flexible substrate. The amount of curve developed in the substrate due to the shrinking of the coating is used to calculate the magnitude of shrinking of the coating (Francis et al., *J Mater Sci* 2002; 37:4717-31, the teachings of which are incorporated herein by reference.)

In some embodiments, the therapeutic films are physiologically stable. The language "physiologically stable" includes the durability of the film upon exposure to normal skin conditions, for example, humidity, tears, sweat or sebum. The physiological stability may be determined by methods typically used by one of ordinary skill in the art, such as an uptake test, which measures the change in weight of the film after exposure to a physiological factor. For example, the uptake test may employ a formulation of simulated sweat (e.g., 1× phosphate buffered saline solution) or simulated sebum (e.g., 25% wax monoesters, 41% triglycerides, 16% free fatty acids and 12% squalene). In some embodiments, the weight of the film increases by less than about 10%, for example, less than about 9%, less than about 8%, less than about 7%, less than about 6%, less than about 5%, less than 4%, less than 3%, less than 2%, less than 1% or exhibits no increase upon exposure to humidity, tears, sweat or sebum.

In some embodiments, the invention pertains, at least in part, to methods for treating wounds, comprising applying to a wound on a subject a formulation comprising a) a first reactive reinforcing component; and b) a second cross-linking component; wherein the cross-linking component catalyzes an in situ cross-linking of the reactive reinforcing component, such that a film is formed on the on the wound, thereby treating the wound. The language "treating a wound" includes protecting the wound from damage while healing, for example, by providing a barrier from environmental elements, such as bacteria, viruses, dirt and the like. In some embodiments, the wound is the site of a skin biopsy. In some embodiments, the wound is not a topical disorder, such as lichen simplex chronicus, cutaneous lupus, psoriasis, eczema, acne, hypertrophic scars, warts or chronic dry skin.

In one embodiment, the invention pertains, at least in part, to methods for preventing a wound from occurring, comprising applying to the skin of a subject a formulation comprising a) a first reactive reinforcing component; and b) a second cross-linking component; in which the cross-linking component catalyzes an in situ cross-linking of the reactive reinforcing component, such that a film is formed on the on the wound, thereby preventing the occurrence of the wound. The language "preventing a wound from occurring" includes inhibiting or impeding the formation of a wound, for example, a wound obtained as a result of environmental exposure (e.g., sun, wind or cold, which may cause sunburn, windburn, dryness or hypothermia) or from mechanical injury (e.g., from rubbing between an external surface and the skin, which my cause irritation of the skin and/or blisters).

In some embodiments, the invention pertains, at least in part, to a method for delivering an agent to a subject in need thereof, comprising applying to the subject's skin a formulation comprising a) a first reactive reinforcing component optionally comprising one or more agents; and b) a second cross-linking component optionally comprising one or more agents; in which the cross-linking component catalyzes an in situ cross-linking of the reactive reinforcing component such that a film is formed on the skin, thereby delivering the agent to the subject. The language "delivering an agent" includes releasing an agent (e.g., a cosmetic or therapeutic agent) to the skin of subject upon formation of the film on the subject's skin. In some embodiments, the agent is delivered in one portion, or the agent is formulated to be delivered in a time-release manner. Examples of agents include cosmetic agents and therapeutic agents.

In some embodiments, the invention pertains, at least in part, to methods for treating a headache in a subject comprising said subject's brow a formulation comprising applying to an appropriate area of the subject's skin a formulation in an amount effective to lift the subject's skin the formulation comprising a) a first reactive reinforcing component and b) a second cross-linking component in which the cross-linking component catalyzes an in situ cross-linking of the reactive reinforcing component such that a film is formed on the skin, thereby treating the headache by lifting the skin.

A headache is pain anywhere in the head or neck of a subject. The term "headache" includes both primary (e.g. a headache without a organic or structural etiology, for example, tension headaches, migraines, cluster headaches) and secondary (e.g. a headache caused by an injury or disorder, for example, a stroke or glaucoma). In a specific embodiment, a headache is a stress or tension headache.

The language "treating a headache" includes reducing, alleviating or ameliorating one or more symptoms of a headache, for example, pain around the head and/or neck. In one embodiment, the headache is a stress headache. In some embodiments, the skin is facial skin (e.g., the skin around the eyes, the skin on the brow or the skin surrounding the lips) or neck skin. In some embodiments, upon application of the therapeutic formulation, the body or skin is lifted by about 5%, about 10%, about 15%, about 20%, about 25%, about 30%, about 35%, about 40% or by about 50% compared to the subject's untreated body or skin. In some embodiments, the body or skin is lifted by about 1 mm, about 2 mm, about 3 mm, about 4 mm, about 5 mm, about 6 mm, about 7 mm, about 8 mm, about 9 mm, about 1 cm, about 1.5 cm, about 2.0 cm, about 2.5 cm, about 3.0 cm, about 3.5 cm, about 4.0 cm, about 4.5 cm, about 5.0 cm, about 5.5 cm, about 6.0 cm, about 6.5 cm, about 7.0 cm, about 7.5 cm, about 8.0 cm, about 8.5 cm, about 9.0 cm, about 9.5 cm or about 10 cm upon application of the body corrective film.

In some embodiments, the invention pertains, at least in part, to a therapeutic formulation for application to a subject's body, comprising at least one preselected function modulating component, wherein said composition forms a therapeutic film upon application to the subject's body.

The term "preselected" includes components that are chosen prior to the preparation of the formulation. For example, the components may be chosen during the manufacturing process to create a specific formulation. Alternatively, the components may be chosen by the subject prior to application of the formulation.

The language "function modulating component" includes components that allow the therapeutic formulations to be selectively adjusted for a particular use of the film (e.g., reducing the appearance of wrinkles, minimizing shine, masking pores, etc.). The function modulating component or components may be selected based on the physical properties of the film that are necessary to be effectively applied for a particular use of the film. For example, if the formulation will be used to minimize shine, the modulus should be low relative to the values of the other physical properties of the resulting film.

In some embodiments, the invention pertains, at least in part, to a therapeutic formulation that targets a treatment area on a subject's body, comprising at least one preselected treatment specific component, wherein said composition forms a therapeutic film upon application to the target treatment area on the subject's body.

The language "target treatment area" includes an area of the body where the formulation is meant to be applied.

The language "treatment specific component" includes components that allow the therapeutic formulations to be selectively adjusted for a target treatment area on the body (e.g., under the eye, forehead, lips, buttocks, neck, etc. . . . ). The treatment specific component or components may be selected based on the physical properties of the film that results from the formulations that are necessary to be effectively applied to a target treatment area, as shown in Table 1. For example, if the target treatment area is under the eye, the modulus should be low relative to the values of the other physical properties of the resulting film.

TABLE 1

| Target Treatment Area | Modulus | Elasticity | Elongation | Adhesion | Matte Finish | Texture |
|---|---|---|---|---|---|---|
| Under the eye | Low | High | Medium | High | High | High |
| Forehead | High | High | Medium | High | High | High |
| Lips | Medium | High | High | High | Low | Low |

Examples of function modulating components and treatment specific components include a stiffness component, an elasticity component, an elongation component, an adhesive component, a matte component and a textural component.

The language "stiffness component" includes components that modulate the flexibility of the resulting film, which is determined by measuring the Young's Modulus of the film (see Example 2). Examples of stiffness components include the reactive constituent (e.g., organopolysiloxane and/or hydride functionalized polysiloxane) and the reinforcing constituent.

The language "elasticity component" includes components that modulate the recoil of the resulting film, which is determined by measuring the hysteresis, and includes, for example, the reinforcing constituent.

The language "elongation component" includes components that modulate the stretch of the resulting film, which is determined by measuring the percent elongation to yield. Examples of elongation components include the reactive constituent (e.g., organopolysiloxane and/or hydride functionalized polysiloxane) and the reinforcing constituent.

The language "adhesion component" includes components that modulate the adherence of the resulting film to the skin, as measured by the leather adhesive test (see Example 2). Examples of adhesion components include the reactive constituent (e.g., organopolysiloxane and/or hydride functionalized polysiloxane) and the reinforcing constituent.

The language "matte component" includes components that modulate the gloss of the resulting film, as measured by determining the shine of the resulting film (see Example 3). Examples of matte components include the reinforcing constituent and light scattering particles.

The language "textural component" includes components that modulate the texture of the film so that the resulting film has the look and feel of natural skin, and is measured by determining the friction of the film. One of skill in the art can readily determine methods to measure the friction of the film, for example, by pressing in and dragging a cantilever across the surface and recording the resisting force. Higher friction corresponds to higher recorded force and rougher surfaces tend to have higher friction.

In some embodiments, the invention pertains, at least in part, to a film removing cleanser for use in removing a therapeutic film, wherein said film is prepared by a process comprising the steps of a) applying a reactive reinforcing component to skin; and b) applying a cross-linking component to said reactive reinforcing component, wherein said cross-linking component catalyzes an in situ cross-linking of the reactive reinforcing component.

In other embodiments, the invention pertains, at least in part, to a film removing cleanser comprising a film wetting component, a penetration component, a film swelling component and a film release component.

The language "film removing cleanser" includes a cosmetic formulation that, when applied to a therapeutic film, breaks down the components of the film such that the film may be removed from the body. In some embodiments, the film cleanser removes the film by wetting the film, penetrating the film, swelling the film and releasing the film from the skin.

The language "film wetting component" includes those components of the cleanser that allow the film to absorb liquid. In some embodiments, the film wetting component comprises caprylyl methicone, ethyl trisiloxane or a combination thereof.

The language "penetration component" includes those components of the cleanser that allow the cleanser to permeate the film. Examples of penetration components include siloxane emulsifiers, caprylyl methicone, ethyl trisiloxane or a combination thereof.

The language "film swelling component" includes components of the cleanser which cause the film to expand. Examples of film swelling components include caprylyl methicone, ethyl trisiloxane, isododecane or a combination thereof.

The language "film releasing component" includes components of the cleanser that cause the film to not adhere to the skin or body of the subject to which the film is applied. Examples of film releasing components include glycols, water or a combination thereof.

In some embodiments, the cleanser disrupts the film's mechanical integrity. The language "disrupt the film's mechanical integrity" includes the disturbance of the mechanical features that provide the film its unique properties (e.g., the stiffness, elasticity, elongation, adhesion and the like).

In some embodiments, the cleanser comprises a siloxane phase, an emulsifier phase and an aqueous phase. The language "siloxane phase" includes a component of the cleanser that comprises one or more siloxanes, for example, caprylyl methicone and ethyl trisiloxane. In some embodiments, the siloxane phase also includes isododecane and Aerogel VM2270 (Dow Corning). The language "emulsifier phase" includes a component of the cleanser that comprises one or more emulsifiers, for example, siloxane emulsifiers such as lauryl PEG-9 polydiethylsiloxyethyl dimethicone, PEG-35 Castor oil, or isododecane and lauryl dimethicone/polyglycerin 3 cross polymer. The language "aqueous phase" includes a component of the cleanser that is soluble in water, for example, water, propylene glycol, butylenes diglycol, glycerol or combinations thereof. In some embodiments, the aqueous phase includes MPdiol glycol, preservatives (e.g., neolone PE), optical particles (e.g., silica and DMPA/isophthalic acid/SMDI copolymer & Green 5) and structural particles (e.g., nylon-12).

In some embodiments, the siloxane phase is about 50% of the cleanser, the emulsifier phase is about 8% of the cleanser and the aqueous phase is about 42% of the cleanser.

In some embodiments, the invention pertains, at least in part, to a method of cleaning a body surface having a therapeutic film, comprising applying an effective amount of a film dissolving cleanser to the film, such that said film dissolves. In some embodiments, the body surface is the skin.

In some embodiments, the invention pertains, at least in part, to a formulation for repairing a therapeutic skin applied to the skin in which the formulation comprises a) a first reactive reinforcing component and b) a second cross-linking component; wherein the cross-linking component catalyzes an in situ cross-linking of the reactive reinforcing component such that a film is formed on the skin.

The terms "repair" and "repairing" includes ameliorating imperfections in the therapeutic film after formation of the film on the skin. In some embodiments, the term "repair"

includes mending or patching tears, gaps or breaks in the film. In some embodiments, the term "repair" includes replacing a portion of the film that may have been removed from the skin. In some embodiments, the term "repair" includes re-adhering or re-attaching a portion of the film that may have come loose from the skin (e.g. de-laminated from the skin). In some embodiments, the term "repair" includes swelling the edges of the tear, gap or break in the film to make the film more malleable, such that the film may be able to be reshaped.

In some embodiment, the invention pertains, at least in part, to a method for repairing a therapeutic film applied to skin by a) identifying an area of the film in need of repair; b) optionally smoothing the edges of the film; and c) applying a formulation for repairing the film, wherein the formulation comprises a first reactive reinforcing component and a second cross-linking component; wherein the cross-linking component catalyzes an in situ cross-linking of the reactive reinforcing component such that a film is formed on the skin, thereby repairing the therapeutic film.

The language "smoothing the edges of the film" includes removing, swabbing, swelling, brushing or grinding the edges of the film in the area in need of repair to remove jagged or uneven portions of the film.

In some embodiments, the invention pertains to a kit comprising a first reactive reinforcing component, and a second cross-linking component, wherein the cross-linking component catalyzes an in situ cross-linking of the reactive reinforcing component such that a film is formed on the skin. In some embodiments, the invention pertains, at least in part, to a kit for repairing a therapeutic film in which the kit comprises a formulation comprising a) a first reactive reinforcing component and b) a second cross-linking component wherein the cross-linking component catalyzes an in situ cross-linking of the reactive reinforcing component such that a film is formed on the skin.

In some embodiments, the kit is a multi-compartment kit comprising at least two compartments. In some embodiments, the reactive reinforcing component is in one compartment and the cross-linking component is in a second compartment. In some embodiments, the kit further comprises one or more brushes, one or more swabs, a film removing cleanser, instructions for use or a mirror. In some embodiments, the kit further comprises a pigment dispersion formulation.

EXAMPLES

Example I. Cyclic and Extension Pull Test

Sample Preparation:

For the purpose of bulk mechanical property determination, target materials were cast inside dumbbell shaped molds. The dimensions of the neck of the mold were 20 mm in length, 5 mm in width and 1.5 mm in depth. The "handles" of the mold were 20 mm by 15 mm and provided adequate area to insure secure slip-free grip during testing. The mold dimensions are consistent with the ASTM D638 guidelines.

Once the poured specimens were fully cured and dried, the formed samples were extracted from their individual molds by means of a spatula and the geometry of the finished pieces was measured with digital calipers to determine precise dimensions.

Mechanical Testing:

Mechanical characterization of specimens was carried out on the Instron 3342 (Instron, Norwood Mass.) equipped with 100N load-cell (Instron #2519-103). Dumbbell shaped samples were mounted onto the instrument via modified Instron 2710-101 grips which insured sample didn't slip or fail inside the grips during testing. Two types of tests were performed sequentially on each sample, first the Cyclic Test followed by the Extension Pull Test. It is noted that the first test (e.g., the cyclic test) had negligible effects on the result of the second test (e.g., the extension pull test). Each test was preprogrammed into Bluehill Lite Software used to operate the instrument. The parameters and data analysis associated with each of the two tests is described below.

Cyclic Test:

In order to determine the elasticity of the materials, a cyclic test was designed. The cyclic test was used to determine the most elastic (e.g., spring-like) material and an Instant Residual Strain (I.R.S.) was obtained from this test, as described below. Generally, the more elastic the material, the faster it returns to its original shape after deformation. For perfectly elastic materials, the I.R.S. and cycle test area approach zero, and therefore, the lower the value the better.

Prior to starting the test, a sample was mounted onto the instrument such that the rectangular handle portions of the specimen and none of the specimen neck were fixed within the instrument grips. The instrument grip distance was adjusted such that the sample was at neutral extension as indicated by the instrument force being close to zero (±0.01N). Subsequently, cyclic extension was performed at 1 mm/s to a maximum extension of 15% of initial sample length. A total of 15 cycles are executed and recorded. The stress strain data recorded by instrument was exported into Excel where the reported mechanical properties were calculated.

An Excel template was used to automatically extract a number of parameters. The cyclic Young's Modulus as calculated as the straight line slope of the stress-strain curve of first cycle between 1% and 4%. The R squared value of the linear fit was above 0.99 or the Young's Modulus was discarded. The Instant Residual Strain (I.R.S.) was calculated for each cycle as the strain difference between the loading and unloading curves at half the maximum stress achieved during the 1st cycle. The I.R.S. for the first cycle as well as the average I.R.S. for the 4th through 14th cycles were recorded. The area bound by the loading and unloading curves of each cycle was also calculated. Good agreement was observed between the I.R.S. and the calculated cycle area.

The majority of the materials evaluated were sufficiently flexible and elastic such that the Cyclic Test could be repeated on the same sample without a significant change in calculated properties. This suggests this test does not result in long lasting changes to the tested material.

Extension Pull Test:

The Extension Pull test was used to determine the stiffness and stretchiness of a material by measuring the Young's Modulus and Ultimate Strain. The Young's Modulus was utilized as a measure of material stiffness, while the Ultimate Strain was used as a measure of material flexibility. In order to develop a film with the appearance of skin, the Young's Modulus should fall within a target range (e.g., 0.1-1.0 MPa), while the fracture strain (as measured by the Ultimate Strain) should be sufficiently high (e.g., greater than about 150%) so that the film will not break when being deformed by skin movement.

The sample was mounted onto the instrument such that the rectangular handle portions of the specimen and none of the specimen neck were fixed within the instrument grips. The instrument grip distance was adjusted such that the sample was at neutral extension as indicated by the instrument force being close to zero (±0.01N). Subsequently, extension until sample failure was performed at 10 mm/s. The stress strain data recorded by instrument during the extension was exported to Excel where the reported mechanical properties were calculated.

An Excel template was used to automatically extract a number of parameters from the instrument generated data. The extension Young's Modulus (YM) as calculated as the straight line slope of the stress-strain curve between 6% and 11%. The R squared value of the linear fit was above 0.99 or the Young's Modulus was calculated from a more linear 5% strain range on the stress strain curve. The Shear Modulus (G) was determined from the same strain range as the YM. G was calculated as the slope of the best line fit between recorded stress and $\alpha$-$\alpha$-2, where $\alpha$ is 1 plus the instantaneous strain. The Yield strain was determined as the strain at which the measured stress differed by more than 10% from the Neo-Hookean stress; the multiple of G and ($\alpha$-$\alpha$-2). Ultimate Stress was calculated as the maximum stress recorded during the experiment. The mechanical property calculations presented here are consistent with ASTM D412.

Example 2: Leather T-Peel Adhesion Test

To Determine Adhesiveness of the Target materials, the materials were spread onto a piece of soft flexible leather 25.4 mm wide and 76.2 mm long. The leather used as test substrate was light weight upholstery leather (AD1100 from Leather Unlimited, Belgium Wis.). Immediately after spreading the material onto the first piece of leather, a second equivalent piece of leather was placed on top to sandwich a thin layer of material between the two pieces. The two pieces of leather were pressed together to leave a thin homogeneous layer of material at the interface of the two leather substrates. The edges were wiped to remove access materials and the material was allowed to cure and dry to form a test specimen.

The adhesion test sample was partially pealed at one end by hand to separate enough of the two leather substrates for effective grip by Instron 3342 mounts. Each leather substrate was secured in its own instrument grip and an extension test was performed at a rate of 10 mm/s to peel the two substrates from each other. The force vs. time data was recorded by instrument during the extension and exported to Excel where the reported adhesive force was calculated.

An Excel template was used to automatically extract adhesive parameters from the instrument generated data. The sample average adhesive force was calculated by averaging the instantaneous force measured by the instrument during the experiment normalized by the sample width (25.4 mm). This test method was developed in accordance with ASTM D1876. The minimum acceptable adhesion, which depends on the stiffness of the material and the area on which the film is placed, was approximately greater than 25 N/mm Example 3: Stress Testing Methods The mechanical durability of the materials was evaluated by creating an artificial brow lift by applying one of the following methods of pre-tensioning the skin during product application. These methods of pre-tensioning were used to stress the skin surface and pull the brow into a lifted position:

"brow orthogonal push," in which a stress was applied that originated at the eyebrow and is vectored anteriorly away from the eyebrow at an angle that was between 80° and 100° relative to the line of the eyebrow, "corner hairline diagonal pull," in which a stress was applied that originated at the most anterior and lateral point on the panelist's hairline and was vectored anteriorly away from and at an angle between 10° and 80° relative to the line of the eyebrow, "corner hairline orthogonal pull," in which a stress was applied that originated at the most anterior and lateral point on the panelist's hairline and was vectored anteriorly away from and at an angle between 80° and 100° relative to the line of the eyebrow, "lateral hairline orthogonal push" in which a stress was applied that originated at the most lateral point of the hairline that was at or above the level of the eyes and was vectored anteriorly away from at an angle between 80° and 100° relative to the line of the eyebrow.

While the brow was held lifted by one of these stresses, the product was applied to the area of skin over which the tension was being applied. Once the film cured, the stress was removed and the mechanical durability of the film's ability to hold the tensions in the skin was evaluated. This evaluation was achieved by measuring the degree of brow lift using the methods described before and after product application. Durability of the effect was measured by allowing time, normal and exaggerated facial expressions and environmental stresses such as water, sweat, heat, sebum production and surface contact to interact with the film. The amount of lift was tracked at regular intervals to determine how quickly the film's ability to hold the mechanical benefit lasted. A film was determined to be mechanically durable if it could withstand the stresses previously mentioned and maintain the brow lift at the level originally achieved immediately after application.

Example 4. Formulations

Examples of formulations illustrating the two-step application method are provided below. The reactive reinforcing component first step (e.g., the treatment) includes formulations 60-140-1, 60-140-1B, 60-140-HP2, SK 87/2, 60-140-LX2, SK 87/1, 48-196, 48-199, 60-211, 60-200-1N, 60-208, 66-166-F, 66-167-E, 66-166-C, 66-169-3, 66-170, 79-23, 79-24b, 79-45, 79-46, 79-41, 88-30-1, 83-16, 79-55a, 79-55b, 79-55c, 79-55d, 79-55e, 79-55f, 79-55g, 83-54, 79-55h, 81-18, 81-19, 81-20, 81-21, 79-74, 80-23, 79-88, 79-88-3A, 79-74-RD, 79-90-B, 88-70, 88-72, 88-75-2, 88-75-3, 88-80, 88-85-1, 88-85-2, 88-83-V2, 88-83-V3 and 83-54 are shown below.

Components of the formulations are commercially available. The following table provides the generic name for any trade name used throughout this application.

| Tradename | International Nomenclature Cosmetic Ingredient (INCI) name |
|---|---|
| Aerogel VM2270 | Silica Silylate |
| Aerosil 8200 ™ or Aerosil R8200 ™ | Fumed silica modified with hexamethyldisilazane |
| Andisil C1000 ™ | Silicon dioxide + Dimethylpolysiloxane |
| Andisil C1300 ™ | Silicon dioxide + Dimethylpolysiloxane |
| Andisil CE-4 ™ | Vinyl Dimethicone |
| Andisil MV 2,000 ™ or MV2000 | Vinyl Dimethicone |

| Tradename | International Nomenclature Cosmetic Ingredient (INCI) name |
|---|---|
| Andisil VS 1,000 ™ | Vinyl Dimethicone |
| Andisil VS 10,000 ™ | Vinyl Dimethicone |
| Andisil VS 165,000 ™ or Andisil VS165K | Vinyl Dimethicone |
| Andisil VS 20,000 ™ | Vinyl Dimethicone |
| Andisil VS 250 ™ | Vinyl Dimethicone |
| Andisil VS 500 ™ or VS500 | Vinyl Dimethicone |
| Andisil VS 65,000 ™ or VS65,000 | Vinyl Dimethicone |
| Andisil XL-11 ™ | Hydrogen Dimethicone, SiH Functional |
| Andisil XL-1B ™ or XL-1B | Hydrogen Dimethicone, SiH Functional |
| Aquadispersable Rutile Titanium Dioxide ™ | Titanium dioxide |
| Barium Sulfate HL | Barium Sulfate |
| Beaver UV/Fluorescent Pigment | AROMATIC HETEROCYCLE |
| Cabosperse 1030K | CAB-O-SPERSE ® 1030K is an aqueous dispersion of CAB-O-SIL ® L-90, a very low surface area, fumed silica. It is electrostatically stabilized with Potassium Hydroxide and has an alkaline pH. |
| Carbopol Ultrez 21 | Acrylates/C10-30 Alkyl Acrylate Crosspolymer |
| Cetiol OE | Dicapryl Ether |
| Chronosphere Optical Brite or Chronosphere Opticals/Opticals Brite | Silica and polyurethane-40/silica and polyurethane-40 and green 5 |
| cremaphor EL | PEG-35 Castor Oil |
| Crodamol STS | PPG 3 Benzyl Ether Myristate |
| DC 200 Fluid (1 cSt) | Dimethicone |
| DC 2-1184 fluid (DOW CORNING ® 2-1184 FLUID) | Trisiloxane (and) Dimethicone |
| DC 556 | Phenyl Trimethicone |
| DMF5 CS | dimethicone |
| DMS-V41 | Poly(Dimethylsiloxane), Vinyl Terminated |
| Dow 245 Fluid (Dow CORNING 245 Fluid) | Cyclopentasiloxane |
| Dow 246 Fluid (Dow CORNING 246 Fluid) | Cyclohexasiloxane |
| Dow 9011 Elastomer Blend (Dow Corning 9011 Elastomer Blend) | Cyclopentasiloxane (and) PEG-12 Dimethicone Crosspolymer |
| Dow Corning 9011 Silicone Elastomer Blend ™ or Dow Elastomer Blend 9011 | Cyclopentasiloxane (and) PEG-12 Dimethicone Crosspolymer |
| Dow 9045 Elastomer Blend or Dow Corning 9045 Silicone Elastomer Blend ™ | Cyclopentasiloxane (and) Dimethicone Crosspolymer |
| Dow Corning 200 Fluid 0.65 cSt ™ | Hexamethyldisiloxane |
| Dow Corning 245 Fluid ™ | Decamethylcyclopentasiloxane |
| Dow Corning 5329 | PEG-12 Dimethicone |
| Dow Elastomer Blend 9041 or DOW CORNING ® 9041 SILICONE ELASTOMER BLEND | Dimethicone (and) Dimethicone Crosspolymer |
| dowanol DPM | Dipropylene Glycol Methyl Ether |
| Dri-Flow Elite BN or DRY-FLO Elite BN | Aluminum Starch Octenylsuccinate (and) Boron Nitride |
| Flo-Beads SE-3207B ™ | Ethylene-methyl methacrylate copolymer |
| Dow Corning FZ-3196 | Caprylyl Methicone |
| Ganzpearl GMP-0830 ™ | Acrylates Crosspolymer |
| Granhydrogel O ™ | Water (and) Glyceryl Polyacrylate (and) 1,3-Butylene Glycol (and) PVM/MA (and) Propylparaben (and) Methylparaben |
| Granpowder Nylon ™ | Nylon-12 |
| Gransil EP-LS ™ | Polysilicone-11 (and) Laureth-12 |
| Gransurf 90 | Cetyl PEG/PPG-10/1 Dimethicone |
| Iris | C12-17 Alkanes |
| Iron Oxide Tint or Iron Oxide Tint Mixture | Iron Oxides |
| Isododecane | mixture of highly branched C12 isoparaffins, mainly the 2,2,4,6,6-pentamethylheptane isomer (typically c.a. 85%). |
| Jeechem BUGL ™ or Jeen BUGL | Butylene Glycol |
| Jeecide cap 5 | Phenoxyethanol, Caprylyl Glycol, Potassium Sorbate, Aqua, Hexylene Glycol |
| Jeensilc CPS-312 ™ | Cyclomethicone |
| Kaolin USP BC2747 | Kaolin |
| KF6013 | PEG-9 Dimethicone |
| KTZ Xian Vistas ™ | Titanium Dioxide (And) Mica (And) Iron Oxide (C.I. 77491); chemical name: Mica (and) Titanium Dioxide (and) Ferrous Oxide |
| Labrafac CC ™ | Caprylic/Capric Triglyceride |
| LILAC ™ (Sonneborn) | C14-22 Alkane |
| MPDiol | Methyl Propanediol |
| Neolone PE ™ | Phenoxyethanol, Methylisothiazolinone |
| Nylon | Nylon 12 |
| Nylon 10-I2 ™ | Nylon 12 (And) Isopropyl Titanium Triisostearate |
| PC 075.3 | Hydrogen Dimethicone |
| Pink tint mix | Iron Oxides |
| Plantacare 818 UP ™ | Coco-Glucoside; Chemical Description is "C8-16 fatty alcohol glucoside" |
| Platinum divinyl complex (for example PT-50175F) | UPAC name "1,3-Diethenyl-1,1,3,3-tetramethyldisiloxane-platinum (1:1)"; Trade name: "Platinum-divinyltetramethyldisiloxane complex"; Synonyms: Platinum(0)-1,3-divinyl-1,1,3,3-tetramethyldisiloxane complex solution; pt(0)-1,3-divinyl-tetrame-disiloxane compl 0.100; 1,3-Divinyl-1,1,3,3-tetramethyl-disiloxane-platinum (0) |
| PMX-1184 or XIAMETER ® PMX-1184 Silicone Fluid | Dimethicone and trisiloxane |
| Polyglycol P425 | PPG-9 |
| prestige pearlescent beige | mixture of titanium and iron oxides of a beige color |
| PS123-KG | Hydrogen Dimethicone |
| RM 2051 or RM 2051 Thickening Agent | Sodium Polyacrylate (and) Dimethicone (and) Cyclopentasiloxane (and) Trideceth-6 (and) PEG/PPG 18/18 |
| Schercemol ™ 318 Ester | Isopropyl Isostearate |
| Sepiplus 400 ™ | Polyacrylate 13 (and) Polyisobutene (and) Polysorbate 20 |
| Shin Etsu KF 6038 | Lauryl PEG-9 Polymethylsiloxyethyl Dimethicone |
| Shin Etsu KSG 820 | Lauryl Dimethicone/Polyglycerin-3 Crosspolymer |
| Silsoft 034 | caprylyl methicone |
| silsoft ETS | ethyl trisiloxane |
| Simulgel EG ™ | Sodium acrylate/acryloyldimethyl taurate copolymer & Isohexadecane & Polysorbate 80 |
| SIMULGEL NS | Hydroxyethylacrylate/sodium acryloyldimethyl taurate copolymer & squalane & polysorbate 60 |
| Soft Bead B or Soft Beads B | Ethylene/Methacrylate Copolymer |
| Solagum AX | Acacia senegal gum and xanthan gum |
| SR 1000 Resin | Trimethylsiloxysilicate |
| Tint | Iron Oxides |
| TMF 1.5 | Methyl Trimethicone |
| Tween 20 | Polysorbate 20 |
| UCT-PS448.5 | Polydimethylsiloxane, Vinyldimethyl Terminated |
| USG 102 | Dimethicone/Vinyl Dimethicone Crosspolymer |
| Veegum Pro | Tromethamine Magnesium Aluminum Silicate |
| Veegum Ultra Granules | Magnesium Aluminum Silicate |
| Velvesil 125 ™ | Cyclopentasiloxane (and) C30-45 Alkyl Cetearyl Dimethicone Crosspolymer |
| Velvet Veil 310 ™ | Mica (and) Silica |
| Vitamin-A complex | retinol |
| Vitamin-C complex | ascorbic acid |

Formulation 60-140-1

| Component No. | Component | Percent of Formulation (%) |
|---|---|---|
| 1 | DMS-V41 | 23.80 |
| 2 | Aerosil 8200 | 9.45 |
| 3 | PS123-KG | 12.00 |
| 4 | UCT-PS448.5 | 5.55 |
| 5 | Velvesil 125 | 3.60 |
| 6 | Gransil EP-LS | 3.60 |
| 7 | Soft Beads B | 1.20 |
| 8 | Sepiplus 400 | 1.20 |
| 9 | Water | 27.00 |
| 10 | Granhydrogel O | 6.70 |
| 11 | Granpowder Nylon | 5.90 |

-continued

| Tradename | International Nomenclature Cosmetic Ingredient (INCI) name |
|---|---|
| Vitamin-E complex | Tocopherol |
| Xirona caribbean blue | Mica, Titanium Dioxide, Silica, Tin Oxide |

Procedure:

Components 1-4 were hand mixed in a graduated 4-oz until mixture was free of white particulates. Subsequently, components 5-8 were added and the mixture was confirmed as homogenous (Mixture A). In a separate vessel, components 9 and 10 were hand mixed until homogenous (Mixture B). Mixture B was added to Mixture A under strong agitation, provided by a 4-blade, 40 mm propeller at 550 rpm, then component 11 was added and the mixing speed was to 1000 rpm and mix for 5 minutes. The mixture was confirmed as homogenous.

Formulation 60-140-1B

| Component No. | Component | Percent of Formulation (%) |
|---|---|---|
| 1 | DMS-V41 | 22.60 |
| 2 | Aerosil 8200 | 8.94 |
| 3 | PS123-KG | 11.30 |
| 4 | UCT-PS448.5 | 5.30 |
| 5 | Velvesil 125 | 3.42 |
| 6 | Gransil EP-LS | 3.42 |
| 7 | Soft Beads B | 1.20 |
| 8 | Sepiplus 400 | 1.20 |
| 9 | Water | 25.66 |
| 10 | Granhydrogel O | 6.36 |
| 11 | Granpowder Nylon | 5.60 |
| 12 | Cetiol OE | 5.00 |

Procedure:

Components 1-4 were hand mixed in a graduated 4-oz and the mixture was confirmed as free of white particulates. Subsequently, components 5-8 were added and the mixture was confirmed homogenous (Mixture A). In a separate vessel, components 9 and 10 were hand mixed until homogenous (Mixture B). Mixture B to was added Mixture A under strong agitation, provided by a 4-blade, 40 mm propeller at 550 rpm, then components 11 and 12 were added and the mixing speed was increased to 1000 rpm and mix for 5 minutes. The mixture was confirmed as homogenous.

Formulation 60-140-HP2

| Component No. | Component | Percent of Formulation (%) |
|---|---|---|
| 1 | UCT-PS448.5 | 32.97 |
| 2 | Aerosil 8200 | 12.82 |
| 3 | PS123-KG | 14.65 |
| 4 | Velvesil 125 | 4.40 |
| 5 | Gransil EP-LS | 4.40 |
| 6 | Soft Beads B | 1.47 |
| 7 | Sepiplus 400 | 1.47 |
| 8 | Granhydrogel O | 20.63 |
| 9 | Granpowder Nylon | 7.20 |

Procedure:

Components 1-3 were hand mixed in a graduated 4-oz and the mixture was confirmed as free of white particulates. Subsequently, components 4-7 were added the mixture was confirmed homogenous (Mixture A). In a separate vessel, component 8 was mixed until homogenous (Mixture B). Mixture B to was added Mixture A under strong agitation, provided by a 4-blade, 40 mm propeller at 550 rpm, then component 9 was added and the mixing speed was increased to 1000 rpm and mix for 5 minutes. The mixture was confirmed as homogeneous.

Formulation SK 87/2

| Component No. | Component | Percent of Formulation (%) |
|---|---|---|
| 1 | DMS V41 | 35.00 |
| 2 | Aerosil 8200 | 11.60 |
| 3 | PS123-KG | 5.20 |
| 4 | Velvesil 125 | 11.20 |
| 5 | Gransil EP-LS | 8.70 |
| 6 | Water | 6.70 |
| 7 | Polyvinyl alcohol | 2.00 |
| 8 | Granhydrogel O | 8.70 |
| 9 | Granpowder Nylon | 6.10 |
| 10 | Silsoft 034 | 4.80 |

Procedure:

Components 1-3 were hand mixed in a graduated 4-oz and the mixture was confirmed as free of white particulates. Subsequently, components 4 and 5 were added and the mixture was confirmed as homogenous (Mixture A). In a separate vessel, components 6 and 7 were hand mixed until homogenous (Mixture B). Mixture B was added to Mixture A under strong agitation, provided by a 4-blade, 40 mm propeller at 550 rpm, then components 8-10 were added and the mixing speed was increased to 1000 rpm and mix for 5 minutes. The mixture was confirmed as homogeneous.

Formulation 60-140-LX2

| Component No. | Component | Percent of Formulation (%) |
|---|---|---|
| 1 | DMS V41 | 27.51 |
| 2 | Aerosil 8200 | 10.87 |
| 3 | PS123-KG | 3.47 |
| 4 | UCT-PS448.5 | 13.41 |
| 5 | Velvesil 125 | 4.16 |
| 6 | Gransil EP-LS | 4.16 |
| 7 | Soft Bead B | 1.39 |
| 8 | Sepiplus 400 | 1.39 |
| 9 | Water | 21.45 |

| Component No. | Component | Percent of Formulation (%) |
| --- | --- | --- |
| 10 | Granhydrogel O | 5.38 |
| 11 | Granpowder Nylon | 6.82 |

Procedure:

Components were hand mixed 1-4 in a graduated 4-oz and the mixture was confirmed as free of white particulates. Subsequently, components 5-8 were added and mixture was confirmed as homogenous (Mixture A). In a separate vessel, components 9 and 10 were hand mixed until homogenous (Mixture B). Mixture B was added to Mixture A under strong agitation, provided by a 4-blade, 40 mm propeller at 550 rpm, then component 11 was added and the mixing speed was increased to 1000 rpm and mixed for 5 minutes. The mixture was confirmed as homogeneous.

Formulation SK 87/1

| Component No. | Component | Percent of Formulation (%) |
| --- | --- | --- |
| 1 | DMS V41 | 36.90 |
| 2 | Aerosil 8200 | 12.30 |
| 3 | PS123-KG | 5.50 |
| 4 | Velvesil 125 | 11.60 |
| 5 | Gransil EP-LS | 9.10 |
| 6 | Water | 7.10 |
| 7 | Polyvinyl alcohol | 2.00 |
| 8 | Granhydrogel O | 9.10 |
| 9 | Granpowder Nylon | 6.40 |

Procedure:

Components 1-3 were hand mixed in a graduated 4-oz and the mixture was confirmed as free of white particulates. Subsequently, components 4 and 5 were added and the mixture was confirmed as homogenous (Mixture A). In a separate vessel, components 6 and 7 were hand mixed until homogenous (Mixture B). Mixture B was added to Mixture A under strong agitation, provided by a 4-blade, 40 mm propeller at 550 rpm, then components 8 and 9 were added and the mixing speed was increased to 1000 rpm and mixed for 5 minutes. The mixture was confirmed as homogeneous.

Formulation 48-196

| Component No. | Component | Percent of Formulation (%) |
| --- | --- | --- |
| 1 | Andisil VS10,000 | 24.46 |
| 2 | Andisil VS165K | 3.66 |
| 3 | Aerosil 8200 | 9.72 |
| 4 | Andisil XL-11 | 12.33 |
| 5 | Velvesil 125 | 3.70 |
| 6 | Gransil EP-LS | 3.70 |
| 7 | Soft Beads B | 1.23 |
| 8 | Sepiplus 400 | 1.23 |
| 9 | Water | 27.75 |
| 10 | Granhydrogel O | 6.87 |
| 11 | Neolone PE | 0.21 |
| 12 | Granpowder Nylon | 4.11 |
| 13 | Tint | 1.03 |

Procedure:

Components 1-3 were mixed in a graduated 4-oz with a 4-blade propeller at 1000 RPM until homogenous (Mixture A) and the mixture was confirmed as homogenous. In a separate container components 4-8 were mixed with a 4-blade propeller at 750 RPM until homogenous (Mixture B). In another container, components 9-11 were mixed with a 4-blade propeller at 750 RPM until homogenous (Mixture C). Mixture B was added to Mixture C under strong agitation, provided by a 4-blade, 40 mm propeller at 750 rpm, then Mixture A was added to combined Mixtures B and C drop by drop. Finally, components 12 and 13 were added and the mixing speed increased to 1000 RPM and mix for 10 minutes. The mixture was confirmed as homogeneous.

Formulation 48-199

| Component No. | Component | Percent of Formulation (%) |
| --- | --- | --- |
| 1 | Andisil VS10,000 | 22.11 |
| 2 | Andisil VS165K | 3.31 |
| 3 | Aerosil 8200 | 8.79 |
| 4 | Andisil XL-11 | 11.15 |
| 5 | Velvesil 125 | 3.35 |
| 6 | Gransil EP-LS | 3.35 |
| 7 | Soft Beads B | 1.12 |
| 8 | Sepiplus 400 | 1.12 |
| 9 | Water | 25.09 |
| 10 | Granhydrogel O | 6.21 |
| 11 | Neolone PE | 0.19 |
| 12 | Granpowder Nylon | 4.94 |
| 13 | Silsoft 034 | 9.29 |

Procedure:

Components 1-3 were mixed in a graduated 4-oz with a 4-blade propeller at 1000 RPM until homogenous (Mixture A). In a separate container, components 4-8 were mixed with a 4-blade propeller at 750 RPM until homogenous (Mixture B). In another container, components 9-11 were mixed with a 4-blade propeller at 750 RPM until homogenous (Mixture C). Mixture B to Mixture C was added under strong agitation, provided by a 4-blade, 40 mm propeller at 750 rpm, then Mixture A was added to combined Mixtures B and C drop by drop. Finally, components 12 and 13 were added and the mixing speed was added to 1000 RPM and mixed for 10 minutes. The mixture was confirmed as homogeneous.

Formulation 60-211

| Component No. | Component | Percent of Formulation (%) |
| --- | --- | --- |
| 1 | Andisil C1000 | 33.66 |
| 2 | Andisil C1300 | 6.73 |
| 3 | Andisil XL-11 | 9.62 |
| 4 | Velvesil 125 | 3.46 |
| 5 | Gransil EP-LS | 3.46 |
| 6 | Soft Beads B | 1.15 |
| 7 | Sepiplus 400 | 1.15 |
| 8 | Water | 25.97 |
| 9 | Granhydrogel O | 6.42 |
| 10 | Jeechem BUGL | 3.85 |
| 11 | Neolone PE | 0.19 |
| 12 | Granpowder Nylon | 3.85 |
| 13 | Tint | 0.49 |

Procedure:

Components 1-7 were mixed in a graduated 4-oz with a 4-blade propeller at 2000 RPM until homogenous (Mixture A). In a separate container, components 8-11 were mixed with a 4-blade propeller at 750 RPM until homogenous (Mixture B). Mixture B was slowly added to Mixture A under strong agitation provided by a 4-blade propeller at 2000 RPM. Components 12 and 13 were added and the mixing speed was increased to 2000 RPM for 5 minutes. The mixture was confirmed as homogeneous.

Formulation 60-200-1N

| Component No. | Component | Percent of Formulation (%) |
|---|---|---|
| 1 | Andisil C1000 | 33.88 |
| 2 | Andisil C1300 | 7.65 |
| 3 | Andisil XL-11 | 18.03 |
| 4 | SR 1000 Resin | 10.93 |
| 5 | Iris | 2.19 |
| 6 | Dri-Flow Elite BN | 10.93 |
| 7 | Barium Sulfate HL | 4.37 |
| 8 | Gransil EP-LS | 8.74 |
| 9 | Sepiplus 400 | 2.19 |
| 10 | Neolone PE | 0.55 |
| 11 | Tint | 0.54 |

Procedure:

Components 1-5 were mixed in a graduated 4-oz with a 4-blade propeller at 2000 RPM until homogenous (Mixture A). Components 6-9 were then added and mixed with a 4-blade propeller at 2000 RPM until homogenous. Components 10 and 11 were added and the mixing speed was mixed at 2000 RPM until homogeneous.

Formulation 60-208

| Component No. | Component | Percent of Formulation (%) |
|---|---|---|
| 1 | Andisil C1000 | 30.05 |
| 2 | Andisil C1300 | 6.56 |
| 3 | Andisil XL-11 | 22.95 |
| 4 | SR 1000 Resin | 10.93 |
| 5 | Iris | 2.19 |
| 6 | Dri-Flow Elite BN | 10.93 |
| 7 | Barium Sulfate HL | 4.37 |
| 8 | Gransil EP-LS | 8.74 |
| 9 | Sepiplus 400 | 2.19 |
| 10 | Neolone PE | 0.55 |
| 11 | Tint | 0.54 |

Procedure:

Components 1-5 were mixed in a graduated 4-oz with a 4-blade propeller at 2000 RPM until homogenous (Mixture A). Components 6-9 were then added and mixed with a 4-blade propeller at 2000 RPM until homogenous. Components 10 and 11 were added and the mixing speed was mixed at 2000 RPM until homogeneous.

Formulation 66-166-F

| Component No. | Component | Percent of Formulation (%) |
|---|---|---|
| 1 | Aerosil 8200 ™ | 8.43% |
| 2 | Andisil VS 10,000 ™ | 21.22% |
| 3 | Andisil VS 165,000 ™ | 3.17% |
| 4 | Andisil XL11 ™ | 10.34% |
| 5 | Velvesil 125 ™ | 3.10% |
| 6 | Gransil EP-LS ™ | 3.10% |
| 7 | Flo-Beads SE-3207B ™ | 1.03% |
| 8 | Sepiplus 400 ™ | 1.03% |
| 9 | Water | 23.28% |
| 10 | Granhydrogel O ™ | 5.75% |
| 11 | Neolone PE ™ | 0.17% |
| 12 | Granpowder Nylon ™ | 4.23% |
| 13 | Ganzpearl GMP-0830 ™ | 0.31% |
| 14 | Velvet Veil 310 ™ | 0.21% |
| 15 | Aquadispersable Rutile Titanium Dioxide ™ | 0.21% |
| 16 | Yellow Iron Oxide | 0.09% |
| 17 | Red Iron Oxide | 0.04% |
| 18 | Black Iron Oxide | 0.01% |
| 19 | Dow Corning 200 Fluid 0.65 cSt ™ | 14.29% |

Procedure:

Components 1-3 were mixed together as siloxane phase A. Into siloxane phase B, components 4-8 were mixed. Components 9-11 were combined as the water phase. The water phase was slowly added to siloxane phase B and mixed until homogenous. Into this new phase, phase A was added very slowly drop by drop. Once all of siloxane phase A was added, components 12-19 were added to the formula and mix until homogenous.

Formulation 66-167-E

| Component No. | Component | Percent of Formulation (%) |
|---|---|---|
| 1 | Aerosil 8200 ™ | 8.36% |
| 2 | Andisil VS 10,000 ™ | 21.05% |
| 3 | Andisil VS 165,000 ™ | 3.15% |
| 4 | Andisil XL11 ™ | 10.25% |
| 5 | Velvesil 125 ™ | 3.08% |
| 6 | Gransil EP-LS ™ | 3.08% |
| 7 | Flo-Beads SE-3207B ™ | 1.02% |
| 8 | Sepiplus 400 ™ | 1.02% |
| 9 | Water | 23.09% |
| 10 | Granhydrogel O ™ | 5.70% |
| 11 | Neolone PE ™ | 0.17% |
| 12 | Granpowder Nylon ™ | 4.20% |
| 13 | Ganzpearl GMP-0830 ™ | 0.31% |
| 14 | Velvet Veil 310 ™ | 0.20% |
| 15 | Aquadispersable Rutile Titanium Dioxide ™ | 0.20% |
| 16 | Yellow Iron Oxide | 0.09% |
| 17 | Red Iron Oxide | 0.04% |
| 18 | Black Iron Oxide | 0.01% |
| 19 | LILAC ™ (Sonneborn) | 2% |
| 20 | Cetyl Dimethicone | 5% |
| 21 | Granhydrogel O ™ | 8% |

Procedure:

Components 1-3 were mixed together as siloxane phase A. Into siloxane phase B components 4-8 were added. Components 9-11 were combined as the water phase. The water phase was slowly added to siloxane phase B and mixed until homogenous. Into this new phase, phase A was added very slowly drop by drop. Once all of siloxane phase A was added, components 12-21 were added to the formula and mixed until homogenous.

Formulation 66-166-C

| Component No. | Component | Percent of Formulation (%) |
|---|---|---|
| 1 | Aerosil 8200 ™ | 8.43% |
| 2 | Andisil VS 10,000 ™ | 21.22% |
| 3 | Andisil VS 165,000 ™ | 3.17% |
| 4 | Andisil XL11 ™ | 10.34% |
| 5 | Velvesil 125 ™ | 3.10% |
| 6 | Gransil EP-LS ™ | 3.10% |
| 7 | Flo-Beads SE-3207B ™ | 1.03% |
| 8 | Sepiplus 400 ™ | 1.03% |
| 9 | Water | 23.28% |

-continued

| Component No. | Component | Percent of Formulation (%) |
|---|---|---|
| 10 | Granhydrogel O ™ | 5.75% |
| 11 | Neolone PE ™ | 0.17% |
| 12 | Granpowder Nylon ™ | 4.23% |
| 13 | Ganzpearl GMP-0830 ™ | 0.31% |
| 14 | Velvet Veil 310 ™ | 0.21% |
| 15 | Aquadispersable Rutile Titanium Dioxide ™ | 0.21% |
| 16 | Yellow Iron Oxide | 0.09% |
| 17 | Red Iron Oxide | 0.04% |
| 18 | Black Iron Oxide | 0.01% |
| 19 | Granhydrogel O ™ | 14.29% |

Procedure:

Components 1-3 were mixed together as siloxane phase A. Into siloxane phase B components 4-8 were added. Components 9-11 were combined as the water phase. The water phase was slowly added to siloxane phase B and mixed until homogenous. Into this new phase, phase A was very slowly added drop by drop. Once all of siloxane phase A was added, components 12-19 was added to the formula and mixed until homogenous.

Formulation 66-169-3

| Component No. | Component | Percent of Formulation (%) |
|---|---|---|
| 1 | Ganzpearl GMP-0830 ™ | 0.16% |
| 2 | Velvet Veil 310 ™ | 0.10% |
| 3 | Aquadispersable Rutile Titanium Dioxide ™ | 0.10% |
| 4 | Yellow Iron Oxide | 0.04% |
| 5 | Red Iron Oxide | 0.02% |
| 6 | Black Iron Oxide | 0.01% |
| 7 | Gransil EP-LS ™ | 0.76% |
| 8 | Andisil XL-11 ™ | 8.61% |
| 9 | Gransil EP-LS ™ | 2.34% |
| 10 | Andisil C1000 ™ | 33.51% |
| 11 | Andisil C1300 ™ | 6.67% |
| 12 | Andisil XL-11 ™ | 1.59% |
| 13 | Velvesil 125 ™ | 3.48% |
| 14 | Flo-Beads SE-3207B ™ | 1.15% |
| 15 | Sepiplus 400 ™ | 1.27% |
| 16 | Water | 25.18% |
| 17 | Granhydrogel O ™ | 6.22% |
| 18 | Jeechem BUGL ™ | 3.75% |
| 19 | Neolone PE ™ | 0.21% |
| 20 | Granpowder Nylon ™ | 3.83% |
| 21 | KTZ Xian Vistas ™ | 1.00% |

Procedure:

Components 1-8 were mixed together and homogenized at 26,000 RPM for 10 minutes. After 10 minutes, component 9 was added and homogenized again for 10 minutes at 26,000 RPM. To this homogenized mixture, components 10-15 were added and mixed with an overhead stirrer at 2,000 RPM until homogenous in appearance (this is the siloxane phase). In a separate container, components 16-19 were mixed until homogenous to form the water phase. The water phase was added to the siloxane phase very slowly, with continuous stirring at 2,000 RPM. Once the water phase was completely mixed in, components 20 and 21 were added to the formula and mixed at 2,000 RPM until homogenous.

Formulation 66-170

| Component No. | Component | Percent of Formulation (%) |
|---|---|---|
| 1 | Andisil C1300 ™ | 8.92% |
| 2 | Andisil C1000 ™ | 44.21% |
| 3 | Andisil XL-11 ™ | 12.67% |
| 4 | Sepiplus 400 ™ | 1.30% |
| 5 | Ganzpearl GMP-0830 ™ | 0.18% |
| 6 | Velvet Veil 310 ™ | 0.12% |
| 7 | Aquadispersable Rutile Titanium Dioxide ™ | 0.12% |
| 8 | Yellow Iron Oxide | 0.05% |
| 9 | Red Iron Oxide | 0.02% |
| 10 | Black Iron Oxide | 0.01% |
| 11 | Dow Corning 9011 Silicone Elastomer Blend ™ | 3.25% |
| 12 | Dow Corning 9045 Silicone Elastomer Blend ™ | 3.25% |
| 13 | Dow Corning 245 Fluid ™ | 2.62% |
| 14 | Jeensilc CPS-312 ™ | 0.65% |
| 15 | Water | 9.49% |
| 16 | Plantacare 818 UP ™ | 0.16% |
| 17 | Propylene Glycol | 6.60% |
| 18 | Glycerin | 1.29% |
| 19 | Jeechem BUGL ™ | 3.22% |
| 20 | Sodium Chloride | 0.32% |
| 21 | Nylon 10-I2 ™ | 1.53% |

Procedure:

Components 1-10 were mixed together to create the siloxane phase A. Next, components 11-14 were mixed to create siloxane phase B. A water phase was created by mixing components 15-20. The water phase was slowly added into siloxane phase B while mixing at 2,000 RPM to create phase C. Finally, phase C was mixed into siloxane phase A until homogenous.

Formulation 79-23

| Component No. | Component | Percent of Formulation (%) |
|---|---|---|
| 1 | Andisil VS 500 ™ | 0.72 |
| 2 | Andisil MV 2000 ™ | 1.02 |
| 3 | Andisil VS 65,000 ™ | 17.20 |
| 4 | Andisil XL-1B ™ | 22.52 |
| 5 | Aerosil R8200 ™ | 11.77 |
| 6 | Ganzpearl GMP-0830 ™ | 0.19 |
| 7 | Velvet Veil 310 ™ | 0.13 |
| 8 | Aquadispersable Rutile Titanium Dioxide ™ | 0.13 |
| 9 | Yellow Iron Oxide | 0.05 |
| 10 | Red Iron Oxide | 0.03 |
| 11 | Black Iron Oxide | 0.01 |
| 12 | Gransil EP-LS ™ | 3.59 |
| 13 | Velvesil 125 ™ | 3.58 |
| 14 | Flo-Beads SE-3207B ™ | 1.02 |
| 15 | Sepiplus 400 ™ | 1.10 |
| 16 | Water | 23.72 |
| 17 | Granhydrogel O ™ | 6.99 |
| 18 | Jeechem BUGL ™ | 3.50 |
| 19 | Sodium Chloride | 0.35 |
| 20 | Neolone PE ™ | 0.35 |
| 21 | Granpowder Nylon ™ | 2.05 |

Procedure:

Components 1-5 were combined and mixed (Mixture A) in a dual asymmetric centrifugal mixer at 2500 RPM while confirming that the mixture was free of white particulates. Components 6-15 were mixed into Mixture A and mixed in a dual asymmetric centrifugal mixer. Mixture A was confirmed as homogenous. In a separate vessel, components 16 and 20 were mixed with a 4-blade, 40 mm propeller at 550 rpm until homogenous (Mixture B). Mixture B was added to Mixture A dropwise while mixing with a 4-blade 40 mm propeller at 2000 rpm and the mixture was confirmed as homogenous. Component 21 was added to the product of Mixture A and Mixture B and mixed with 4-blade 40 mm propeller at 1000 rpm until homogenous.

Formulation 79-24b

| Component No. | Component | Percent of Formulation (%) |
|---|---|---|
| 1 | Andisil VS 500 ™ | 0.72 |
| 2 | Andisil MV 2000 ™ | 1.07 |
| 3 | Andisil VS 65,000 ™ | 17.91 |
| 4 | Andisil XL-1B ™ | 23.15 |
| 5 | Aerosil R8200 ™ | 12.12 |
| 6 | Ganzpearl GMP-0830 ™ | 0.19 |
| 7 | Velvet Veil 310 ™ | 0.13 |
| 8 | Iron Oxide Tint | 0.22 |
| 9 | Gransil EP-LS ™ | 3.70 |
| 10 | Velvesil 125 ™ | 3.70 |
| 11 | Flo-Beads SE-3207B ™ | 1.06 |
| 12 | Sepiplus 400 ™ | 1.11 |
| 13 | Water | 22.31 |
| 14 | Granhydrogel O ™ | 6.56 |
| 15 | Jeechem BUGL ™ | 3.28 |
| 16 | Sodium Chloride | 0.33 |
| 17 | Neolone PE ™ | 0.33 |
| 18 | Granpowder Nylon ™ | 2.12 |

Procedure:

Components 4, 8 and 9 were combined and homogenized until smooth at 20000 RPM. Components 1-3, 6-7, 10-12 were added and mixed with a dual asymmetric centrifugal mixer at 2500 RPM for 6 minutes until particulates were no longer visible (Mixture A). In a separate vessel, components 13-17 were mixed with a 4-blade, 40 mm propeller at 550 rpm until homogenous (Mixture B). Mixture B was added to Mixture A dropwise while mixing with a 4-blade 40 mm propeller at 2000 rpm and the mixture was confirmed as homogenous. Component 18 was added to the product of Mixture A and Mixture B and mixed with 4-blade 40 mm propeller at 1000 rpm until homogenous.

Formulation 79-45

A 2:1 blend of Formulations 60-211 and 79-24b was mixed together with a 4-blade 40 mm propeller at 2000 rpm for 2 minutes.

Formulation 79-46

A 1:2 blend of Formulations 60-211 and 79-24b was mixed together with a 4-blade 40 mm propeller at 2000 rpm for 2 minutes.

Formulation 79-41

A 1:5 blend of Formulations 60-211 and 79-24b was mixed together with a 4-blade 40 mm propeller at 2000 rpm for 2 minutes.

Formulation 88-30-1

| Component No. | Component | Percent of Formulation (%) |
|---|---|---|
| 1 | VS500 | 0.68 |
| 2 | MV2000 | 1.02 |
| 3 | VS65,000 | 17.00 |
| 4 | XL-1B | 21.96 |
| 5 | Aerosil R 8200 | 11.51 |
| 6 | Dow 246 Fluid | 10.43 |
| 7 | Crodamol STS | 1.15 |
| 8 | 83-49 | 12.00 |
| 9 | 83-50 | 3.39 |
| 10 | Cabosperse 1030K | 20.87 |

Procedure:

Ingredients 1 through 7 were mixed using a propeller blade at 275 RPM to prepare phase A. In a separate vessel components 8 through 10 were mixed, using a propeller blade at 275 RPM, to prepare phase B. Phase B was mixed into phase A at 275 RPM until the emulsion is uniform. An amount of 0.01% iron oxides was added to the final formulation to impart color. Formulation 83-49 and 83-50 are emulsions of VS 165,000 vinyl siloxane and XL-11 hydride functionalized siloxane, respectively, containing 65% siloxanes, 8% oleth-10 surfactant, and the balance water.

Formulation 83-16

| Component No. | Component | Percent of Formulation (%) |
|---|---|---|
| 1 | Gransil EP-LS ™ | 3.5 |
| 2 | Andisil XL-11 ™ | 9.76 |
| 3 | Andisil VS 1,000 ™ | 25.53 |
| 4 | Andisil VS 165,000 ™ | 5.12 |
| 5 | Aerosil R8200 ™ | 10.23 |
| 6 | Velvesil 125 ™ | 3.51 |
| 7 | Flo-Beads SE-3207B ™ | 1.17 |
| 8 | Sepiplus 400 ™ | 1.22 |
| 9 | Granpowder Nylon ™ | 3.9 |
| 10 | Water | 25.47 |
| 11 | Granhydrogel O ™ | 6.32 |
| 12 | Jeechem BUGL ™ | 3.97 |
| 13 | Neolone PE ™ | 0.22 |
| 14 | Iron Oxide Tint Mixture | 0.08 |

Procedure:

Components 1 and 2 were combined and homogenized until smooth at 20000 RPM (Mixture A). Components 3 to 9 were added and mixed with a dual asymmetric centrifugal mixer at 2500 RPM for 6 minutes until particulates were no longer visible (Mixture B). Mixture A and Mixture B were combined and centrifuge mixed for 6 minutes at 2500 RPM (Mixture A+B). In a separate vessel, components 10 to 13 were mixed with a 4-blade, 40 mm propeller at 550 rpm until homogenous (Mixture C). Mixture C was added to Mixture A+B dropwise while mixing with a 4-blade 40 mm propeller at 400 rpm and the mixture was confirmed as homogenous. Component 14 was added to the product of Mixture A+B and Mixture C and mixed with 4-blade 40 mm propeller at 1000 rpm until homogenous.

Formulation 79-55a

| Component No. | Component | Percent of Formulation (%) |
|---|---|---|
| 1 | Gransil EP-LS ™ | 3.50 |
| 2 | Andisil XL-11 ™ | 8.17 |
| 3 | Andisil VS 1,000 ™ | 32.59 |
| 4 | Andisil VS 165,000 ™ | 6.52 |
| 5 | Andisil XL-11 ™ | 3.04 |
| 6 | Aerosil R8200 ™ | 13.04 |
| 7 | Sepiplus 400 ™ | 1.14 |
| 8 | Water | 21.76 |
| 9 | Granhydrogel O ™ | 6.40 |
| 10 | Jeechem BUGL ™ | 3.20 |
| 11 | Sodium Chloride | 0.32 |
| 12 | Neolone PE ™ | 0.32 |
| 13 | Iron Oxide Tint Mixture | 0.01 |

Procedure:

Components 1 and 2 were combined and homogenized until smooth at 20000 RPM (Mixture A). Components 3 to 7 were added and mixed with a dual asymmetric centrifugal mixer at 2500 RPM for 6 minutes until particulates are no longer visible (Mixture B). Mixture A and Mixture B were combined and centrifuge mixed for 6 minutes at 2500 RPM (Mixture A+B). In a separate vessel, components 8 to 12 were mixed with a 4-blade, 40 mm propeller at 550 rpm until homogenous (Mixture C). Mixture C was added to Mixture A+B dropwise while mixing with a 4-blade 40 mm propeller at 400 rpm and the mixture was confirmed as homogenous. Component 13 was added to the product of Mixture A+B and Mixture C and mixed with 4-blade 40 mm propeller at 1000 rpm until homogenous.

Formulation 79-55b

| Component No. | Component | Percent of Formulation (%) |
|---|---|---|
| 1 | Gransil EP-LS ™ | 3.50 |
| 2 | Andisil XL-11 ™ | 8.17 |
| 3 | Andisil VS 10,000 ™ | 30.33 |
| 4 | Andisil VS 165,000 ™ | 7.10 |
| 5 | Andisil XL-11 ™ | 5.49 |
| 6 | Aerosil R8200 ™ | 12.26 |
| 7 | Sepiplus 400 ™ | 1.14 |
| 8 | Water | 21.76 |
| 9 | Granhydrogel O ™ | 6.40 |
| 10 | Jeechem BUGL ™ | 3.20 |
| 11 | Sodium Chloride | 0.32 |
| 12 | Neolone PE ™ | 0.32 |
| 13 | Iron Oxide Tint Mixture | 0.01 |

Procedure:

Components 1 and 2 were combined and homogenized until smooth at 20000 RPM (Mixture A). Components 3 to 7 were added and mixed with a dual asymmetric centrifugal mixer at 2500 RPM for 6 minutes until particulates are no longer visible (Mixture B). Mixture A and Mixture B were combined and centrifuge mixed for 6 minutes at 2500 RPM (Mixture A+B). In a separate vessel, components 8 to 12 were mixed with a 4-blade, 40 mm propeller at 550 rpm until homogenous (Mixture C). Mixture C was added to Mixture A+B dropwise while mixing with a 4-blade 40 mm propeller at 400 rpm and the mixture was confirmed as homogenous. Component 13 was added to the product of Mixture A+B and Mixture C and mixed with 4-blade 40 mm propeller at 1000 rpm until homogenous.

Formulation 79-55c

| Component No. | Component | Percent of Formulation (%) |
|---|---|---|
| 1 | Gransil EP-LS ™ | 3.50 |
| 2 | Andisil XL-1B ™ | 8.17 |
| 3 | Andisil VS 500 ™ | 0.84 |
| 4 | Andisil MV 2,000 ™ | 1.29 |
| 5 | Andisil VS 65,000 ™ | 21.04 |
| 6 | Andisil XL-1B ™ | 17.82 |
| 7 | Aerosil R8200 ™ | 14.20 |
| 8 | Sepiplus 400 ™ | 1.14 |
| 9 | Water | 21.76 |
| 10 | Granhydrogel O ™ | 6.40 |
| 11 | Jeechem BUGL ™ | 3.20 |
| 12 | Sodium Chloride | 0.32 |
| 13 | Neolone PE ™ | 0.32 |
| 14 | Iron Oxide Tint Mixture | 0.01 |

Procedure:

Components 1 and 2 were combined and homogenized until smooth at 20000 RPM (Mixture A). Components 3 to 8 were added and mixed with a dual asymmetric centrifugal mixer at 2500 RPM for 6 minutes until particulates are no longer visible (Mixture B). Mixture A and Mixture B were combined and centrifuge mixed for 6 minutes at 2500 RPM (Mixture A+B). In a separate vessel, components 9 to 13 were mixed with a 4-blade, 40 mm propeller at 550 rpm until homogenous (Mixture C). Mixture C was added to Mixture A+B dropwise while mixing with a 4-blade 40 mm propeller at 400 rpm and the mixture was confirmed as homogenous. Component 14 was added to the product of Mixture A+B and Mixture C and mixed with 4-blade 40 mm propeller at 1000 rpm until homogenous.

Formulation 79-55d

| Component No. | Component | Percent of Formulation (%) |
|---|---|---|
| 1 | Gransil EP-LS ™ | 3.50 |
| 2 | Andisil XL-1B ™ | 8.17 |
| 3 | Andisil VS 250 ™ | 1.29 |
| 4 | Andisil MV 2,000 ™ | 1.94 |
| 5 | Andisil VS 20,000 ™ | 24.52 |
| 6 | Andisil CE-4 ™ | 1.94 |
| 7 | Andisil XL-1B ™ | 0.33 |
| 8 | Andisil XL-11 ™ | 10.97 |
| 9 | Aerosil R8200 ™ | 14.20 |
| 10 | Sepiplus 400 ™ | 1.14 |
| 11 | Water | 21.76 |
| 12 | Granhydrogel O ™ | 6.40 |
| 13 | Jeechem BUGL ™ | 3.20 |
| 14 | Sodium Chloride | 0.32 |
| 15 | Neolone PE ™ | 0.32 |
| 16 | Iron Oxide Tint Mixture | 0.01 |

Procedure:

Components 1 and 2 were combined and homogenized until smooth at 20000 RPM (Mixture A). Components 3 to 10 were added and mixed with a dual asymmetric centrifugal mixer at 2500 RPM for 6 minutes until particulates are no longer visible (Mixture B). Mixture A and Mixture B were combined and centrifuge mixed for 6 minutes at 2500 RPM (Mixture A+B). In a separate vessel, components 11 to 15 were mixed with a 4-blade, 40 mm propeller at 550 rpm until homogenous (Mixture C). Mixture C was added to Mixture A+B dropwise while mixing with a 4-blade 40 mm propeller at 400 rpm and the mixture was confirmed as homogenous. Component 16 was added to the product of Mixture A+B and Mixture C and mixed with 4-blade 40 mm propeller at 1000 rpm until homogenous.

Formulation 79-55e

| Component No. | Component | Percent of Formulation (%) |
|---|---|---|
| 1 | Gransil EP-LS ™ | 3.50 |
| 2 | Andisil XL-1B ™ | 8.17 |
| 3 | Andisil VS 250 ™ | 1.29 |
| 4 | Andisil MV 2,000 ™ | 1.94 |
| 5 | Andisil VS 65,000 ™ | 22.91 |
| 6 | Andisil XL-1B ™ | 6.78 |
| 7 | Andisil XL-11 ™ | 8.07 |
| 8 | Aerosil R8200 ™ | 14.20 |
| 9 | Sepiplus 400 ™ | 1.14 |
| 10 | Water | 21.76 |
| 11 | Granhydrogel O ™ | 6.40 |
| 12 | Jeechem BUGL ™ | 3.20 |
| 13 | Sodium Chloride | 0.32 |
| 14 | Neolone PE ™ | 0.32 |
| 15 | Iron Oxide Tint Mixture | 0.01 |

Procedure:

Components 1 and 2 were combined and homogenized until smooth at 20000 RPM (Mixture A). Components 3 to 9 were added and mixed with a dual asymmetric centrifugal mixer at 2500 RPM for 6 minutes until particulates are no longer visible (Mixture B). Mixture A and Mixture B were combined and centrifuge mixed for 6 minutes at 2500 RPM (Mixture A+B). In a separate vessel, components 10 to 14 were mixed with a 4-blade, 40 mm propeller at 550 rpm until homogenous (Mixture C). Mixture C was added to Mixture A+B dropwise while mixing with a 4-blade 40 mm propeller at 400 rpm and the mixture was confirmed as homogenous. Component 15 was added to the product of Mixture A+B and Mixture C and mixed with 4-blade 40 mm propeller at 1000 rpm until homogenous.

Formulation 79-55f

| Component No. | Component | Percent of Formulation (%) |
| --- | --- | --- |
| 1 | Gransil EP-LS ™ | 3.50 |
| 2 | Andisil XL-1B ™ | 8.17 |
| 3 | Andisil VS 250 ™ | 1.34 |
| 4 | Andisil VS 65,000 ™ | 23.74 |
| 5 | Andisil XL-1B ™ | 7.03 |
| 6 | Andisil XL-11 ™ | 8.36 |
| 7 | Aerosil R8200 ™ | 14.71 |
| 8 | Sepiplus 400 ™ | 1.14 |
| 9 | Water | 21.76 |
| 10 | Granhydrogel O ™ | 6.40 |
| 11 | Jeechem BUGL ™ | 3.20 |
| 12 | Sodium Chloride | 0.32 |
| 13 | Neolone PE ™ | 0.32 |
| 14 | Iron Oxide Tint Mixture | 0.01 |

Procedure:

Components 1 and 2 were combined and homogenized until smooth at 20000 RPM (Mixture A). Components 3 to 8 were added and mixed with a dual asymmetric centrifugal mixer at 2500 RPM for 6 minutes until particulates are no longer visible (Mixture B). Mixture A and Mixture B were combined and centrifuge mixed for 6 minutes at 2500 RPM (Mixture A+B). In a separate vessel, components 9 to 13 were mixed with a 4-blade, 40 mm propeller at 550 rpm until homogenous (Mixture C). Mixture C was added to Mixture A+B dropwise while mixing with a 4-blade 40 mm propeller at 400 rpm and the mixture was confirmed as homogenous. Component 14 was added to the product of Mixture A+B and Mixture C and mixed with 4-blade 40 mm propeller at 1000 rpm until homogenous.

Formulation 79-55g

| Component No. | Component | Percent of Formulation (%) |
| --- | --- | --- |
| 1 | Gransil EP-LS ™ | 3.50 |
| 2 | Andisil XL-1B ™ | 8.17 |
| 3 | Andisil VS 250 ™ | 1.29 |
| 4 | Andisil MV 2,000 ™ | 1.94 |
| 5 | Andisil VS 20,000 ™ | 22.91 |
| 6 | Andisil XL-1B ™ | 6.78 |
| 7 | Andisil XL-11 ™ | 8.07 |
| 8 | Aerosil R8200 ™ | 14.20 |
| 9 | Sepiplus 400 ™ | 1.14 |
| 10 | Water | 21.76 |
| 11 | Granhydrogel O ™ | 6.40 |
| 12 | Jeechem BUGL ™ | 3.20 |
| 13 | Sodium Chloride | 0.32 |
| 14 | Neolone PE ™ | 0.32 |
| 15 | Iron Oxide Tint Mixture | 0.01 |

Procedure:

Components 1 and 2 were combined and homogenized until smooth at 20000 RPM (Mixture A). Components 3 to 9 were added and mixed with a dual asymmetric centrifugal mixer at 2500 RPM for 6 minutes until particulates are no longer visible (Mixture B). Mixture A and Mixture B were combined and centrifuge mixed for 6 minutes at 2500 RPM (Mixture A+B). In a separate vessel, components 10 to 14 were mixed with a 4-blade, 40 mm propeller at 550 rpm until homogenous (Mixture C). Mixture C was added to Mixture A+B dropwise while mixing with a 4-blade 40 mm propeller at 400 rpm and the mixture was confirmed as homogenous. Component 15 was added to the product of Mixture A+B and Mixture C and mixed with 4-blade 40 mm propeller at 1000 rpm until homogenous.

Formulation 83-54

| Component No. | Component | Percent of Formulation (%) |
| --- | --- | --- |
| 1 | Andisil VS 10,000 ™ | 27.58 |
| 2 | Andisil VS 165,000 ™ | 6.46 |
| 5 | Andisil XL-11 ™ | 13.50 |
| 6 | Aerosil R8200 ™ | 17.50 |
| 7 | Labrafac CC ™ | 3.00 |
| 7 | Sepiplus 400 ™ | 1.44 |
| 8 | Water | 29.29 |
| 9 | Plantacare 818UP ™ | 0.50 |
| 11 | Sodium Chloride | 0.36 |
| 12 | Neolone PE ™ | 0.36 |
| 13 | Iron Oxide Tint Mixture | 0.01 |

Procedure:

Components 1 to 7 were added and mixed with a dual asymmetric centrifugal mixer at 2500 RPM for 6 minutes until particulates are no longer visible (Mixture A). In a separate vessel, components 8 to 12 were mixed with a 4-blade, 40 mm propeller at 550 rpm until homogenous (Mixture B). Mixture B was added to Mixture A dropwise while mixing with a 4-blade 40 mm propeller at 400 rpm and the mixture was confirmed as homogenous. Component 13 was added to the product of Mixture A and Mixture B and mixed with 4-blade 40 mm propeller at 1000 rpm until homogenous.

Formulation 79-55h

| Component No. | Component | Percent of Formulation (%) |
| --- | --- | --- |
| 1 | Gransil EP-LS ™ | 3.50 |
| 2 | Andisil XL-1B ™ | 8.15 |
| 3 | Andisil VS 250 ™ | 1.25 |
| 4 | Andisil MV 2,000 ™ | 1.85 |
| 5 | Andisil VS 20,000 ™ | 24.40 |
| 6 | Andisil CE-4 ™ | 1.85 |
| 7 | Andisil XL-1B ™ | 0.30 |
| 8 | Andisil XL-11 ™ | 10.80 |
| 9 | Aerosil R8200 ™ | 14.20 |
| 10 | Sepiplus 400 ™ | 1.14 |
| 11 | Water | 21.50 |
| 12 | Granhydrogel O ™ | 6.30 |
| 13 | Jeechem BUGL ™ | 3.15 |
| 14 | Sodium Chloride | 0.30 |
| 15 | Neolone PE ™ | 0.30 |
| 16 | Beaver UV/Fluorescent Pigment | 1.00 |

Procedure:

Components 1 and 2 were combined and homogenized until smooth at 20000 RPM (Mixture A). Components 3 to 10 were added and mixed with a dual asymmetric centrifugal mixer at 2500 RPM for 6 minutes until particulates are no longer visible (Mixture B). Mixture A and Mixture B were combined and centrifuge mixed for 6 minutes at 2500 RPM (Mixture A+B). In a separate vessel, components 11 to 15 were mixed with a 4-blade, 40 mm propeller at 550 rpm until homogenous (Mixture C). Mixture C was added to Mixture A+B dropwise while mixing with a 4-blade 40 mm propeller at 400 rpm and the mixture was confirmed as homogenous. Component 15 was added to the product of Mixture A+B and Mixture C and mixed with 4-blade 40 mm propeller at 1000 rpm until homogenous.
Formulation 81-18

| Component No. | Component | Percent of Formulation (%) |
| --- | --- | --- |
| 1 | Dow 9011 Elastomer Blend | 10.45 |
| 2 | Dow 9045 Elastomer Blend | 10.45 |
| 3 | Dow 245 Fluid | 8.4 |
| 4 | Jeensilc CPS-312 | 2.09 |
| 5 | PT-50175F | 1.00 |
| 6 | Water | 30.33 |
| 7 | Plantacare 818 UP | 0.55 |
| 8 | Neolone PE | 0.21 |
| 9 | Propylene Glycol | 20.87 |
| 10 | Glycerin | 4.16 |
| 11 | Jeechem BUGL | 10.44 |
| 12 | Sodium Chloride | 1.05 |

Procedure:

Components 1-5 were mixed in a glass beaker at 2000 rpm with 4-blade 40 mm propeller for 2 minutes until mixture was homogeneous (Mixture A). Separately, components 6-12 were mixed until homogenous (Mixture B). Mixture B was added to Mixture A under strong agitation provided by a 4-blade, 40 mm propeller at 2000 rpm until homogeneous. The final formulation was further homogenized for 2 minutes.
Formulation 81-19

| Component No. | Component | Percent of Formulation (%) |
| --- | --- | --- |
| 1 | Dow 9011 Elastomer Blend | 10.45 |
| 2 | Dow 9045 Elastomer Blend | 10.45 |
| 3 | Dow 245 Fluid | 8.4 |
| 4 | Jeensilc CPS-312 | 2.09 |
| 5 | PT-50175F | 1.00 |
| 6 | Water | 29.83 |
| 7 | Plantacare 818 UP | 0.55 |
| 8 | Neolone PE | 0.21 |
| 9 | Propylene Glycol | 20.87 |
| 10 | Glycerin | 4.16 |
| 11 | Jeechem BUGL | 10.44 |
| 12 | Sodium Chloride | 1.05 |
| 13 | Nylon 10-12 | 0.5 |

Procedure:

Components 1-5 were mixed in a glass beaker at 2000 rpm with 4-blade 40 mm propeller for 2 minutes until mixture was homogeneous (Mixture A). Separately, components 6-12 were mixed until homogenous (Mixture B). Mixture B was added to Mixture A under strong agitation provided by a 4-blade, 40 mm propeller at 2000 rpm until homogeneous. Component 13 was then added and the resulting mixture was homogenized for 2 minutes.
Formulation 81-20

| Component No. | Component | Percent of Formulation (%) |
| --- | --- | --- |
| 1 | Dow 9011 Elastomer Blend | 10.45 |
| 2 | Dow 9045 Elastomer Blend | 10.45 |
| 3 | Dow 245 Fluid | 8.4 |
| 4 | Jeensilc CPS-312 | 2.09 |
| 5 | PT-50175F | 1.00 |
| 6 | Water | 29.33 |
| 7 | Plantacare 818 UP | 0.55 |
| 8 | Neolone PE | 0.21 |
| 9 | Propylene Glycol | 20.87 |
| 10 | Glycerin | 4.16 |
| 11 | Jeechem BUGL | 10.44 |
| 12 | Sodium Chloride | 1.05 |
| 13 | Nylon 10-12 | 1.0 |

Procedure:

Components 1-5 were mixed in a glass beaker at 2000 rpm with 4-blade 40 mm propeller for 2 minutes until mixture was homogeneous (Mixture A). Separately, components 6-12 were mixed until homogenous (Mixture B). Mixture B was added to Mixture A under strong agitation provided by a 4-blade, 40 mm propeller at 2000 rpm until homogeneous. Component 13 was then added and the resulting mixture was homogenized for 2 minutes.
Formulation 81-21

| Component No. | Component | Percent of Formulation (%) |
| --- | --- | --- |
| 1 | Dow 9011 Elastomer Blend | 10.45 |
| 2 | Dow 9045 Elastomer Blend | 10.45 |
| 3 | Dow 245 Fluid | 8.4 |
| 4 | Jeensilc CPS-312 | 2.09 |
| 5 | PT-50175F | 1.00 |
| 6 | Water | 27.33 |
| 7 | Plantacare 818 UP | 0.55 |
| 8 | Neolone PE | 0.21 |
| 9 | Propylene Glycol | 20.87 |
| 10 | Glycerin | 4.16 |
| 11 | Jeechem BUGL | 10.44 |
| 12 | Sodium Chloride | 1.05 |
| 13 | Nylon 10-12 | 3.0 |

Procedure:

Components 1-5 were mixed in a glass beaker at 2000 rpm with 4-blade 40 mm propeller for 2 minutes until mixture was homogeneous (Mixture A). Separately, components 6-12 were mixed until homogenous (Mixture B). Mixture B was added to Mixture A under strong agitation provided by a 4-blade, 40 mm propeller at 2000 rpm until homogeneous. Component 13 was then added and the resulting mixture was homogenized for 2 minutes.
Formulation 79-74

| Component No. | Component | Percent of Formulation (%) |
| --- | --- | --- |
| 1 | Andisil VS 10,000 ™ | 27.58 |
| 2 | Andisil VS 165,000 ™ | 6.46 |
| 5 | Andisil XL-11 ™ | 13.50 |
| 6 | Aerosil R8200 ™ | 17.50 |
| 7 | Schercemol ™ 318 Ester | 3.00 |
| 7 | Sepiplus 400 ™ | 1.44 |
| 8 | Water | 29.29 |
| 9 | Plantacare 818UP ™ | 0.50 |
| 11 | Sodium Chloride | 0.36 |
| 12 | Neolone PE ™ | 0.36 |
| 13 | Iron Oxide Tint Mixture | 0.01 |

Procedure:

Components 1 to 7 were added and mixed with a dual asymmetric centrifugal mixer at 2500 RPM for 6 minutes until particulates are no longer visible (Mixture A). In a separate vessel, components 8 to 12 were mixed with a 4-blade, 40 mm propeller at 550 rpm until homogenous (Mixture B). Mixture B was added to Mixture A dropwise while mixing with a 4-blade 40 mm propeller at 400 rpm and the mixture was confirmed as homogenous. Component 13 was added to the product of Mixture A and Mixture B and mixed with 4-blade 40 mm propeller at 1000 rpm until homogenous.

Pigment Dispersion Formulation 80-23

| Component No. | Component | Percent of Formulation (%) |
| --- | --- | --- |
| 1 | Dow 9011 Elastomer Blend | 10 |
| 2 | Dow 9045 Elastomer Blend | 10 |
| 3 | Dow 245 Fluid | 10 |
| 4 | Water | 27 |
| 5 | Plantacare 818 UP | 0.5 |
| 6 | Neolone PE | 0.5 |
| 7 | Propylene Glycol | 20 |
| 8 | Glycerin | 4 |
| 9 | Jeechem BUGL | 10 |
| 10 | Sodium Chloride | 1 |
| 11 | Nylon | 4.5 |
| 12 | Tint | 2.5 |

Procedure:

Components 1-3 were mixed in a glass beaker at 2000 rpm with 4-blade 40 mm propeller for 2 minutes until homogenous (Mixture A). Separately, components 5-10 were mixed until homogenous (Mixture B). Mixture was added B to Mixture A under strong agitation, provided by a 4-blade, 40 mm propeller at 2000 rpm until homogeneous. Components 11 and 12 were then added and mix at 200 rpm and until homogeneous. The final mixture was then homogenized for 2 minutes.

Formulation 79-88

| Component No. | Component | Percent of Formulation (%) |
| --- | --- | --- |
| 1 | Andisil VS 10,000 ™ | 27.59 |
| 2 | Andisil VS 165,000 ™ | 6.46 |
| 3 | Andisil XL-11 ™ | 13.50 |
| 4 | Aerosil R8200 ™ | 17.50 |
| 5 | Labrafac CC ™ | 3.00 |
| 6 | Sepiplus 400 ™ | 1.44 |
| 7 | Water | 29.29 |
| 8 | Plantacare 818UP ™ | 0.50 |
| 9 | Sodium Chloride | 0.36 |
| 10 | Neolone PE ™ | 0.36 |

Procedure:

Components 1 to 4 were combined and mixed with KitchenAid mixer for 5 hours. Subsequently the mixture was vacuumed overnight. Components 5 and 6 were then added and the mixture was homogenized in a dual asymmetric centrifugal mixer at 2500RPM. In a separate vessel, components 7 to 10 were mixed with a 4-blade, 40 mm propeller at 550 rpm until homogenous (Mixture B). Mixture B was added to Mixture A dropwise while mixing with a 4-blade 40 mm propeller at 500 rpm and the mixture was confirmed as homogenous.

Formulation 79-88-3A

| Component No. | Component | Percent of Formulation (%) |
| --- | --- | --- |
| 1 | Andisil VS 10,000 ™ | 27.59 |
| 2 | Andisil VS 165,000 ™ | 6.46 |
| 3 | Andisil XL-11 ™ | 13.50 |
| 4 | Aerosil R8200 ™ | 17.50 |
| 5 | Labrafac CC ™ | 3.00 |
| 6 | Simulgel EG ™ | 1.44 |
| 7 | Water | 29.29 |
| 8 | Plantacare 818UP ™ | 0.50 |
| 9 | Sodium Chloride | 0.36 |
| 10 | Neolone PE ™ | 0.36 |

Procedure:

Components 1 to 4 were combined and mixed with KitchenAid mixer for 5 hours. Subsequently the mixture was vacuumed overnight. Components 5 and 6 were then added and the mixture was homogenized in a dual asymmetric centrifugal mixer at 2500RPM. In a separate vessel, components 7 to 10 were mixed with a 4-blade, 40 mm propeller at 550 rpm until homogenous (Mixture B). Mixture B was added to Mixture A dropwise while mixing with a 4-blade 40 mm propeller at 500 rpm and the mixture was confirmed as homogenous.

Formulation 79-74-RD

| Component No. | Component | Percent of Formulation (%) |
| --- | --- | --- |
| 1 | Andisil VS 500 ™ | 0.52 |
| 2 | Andisil MV 2000 ™ | 0.80 |
| 3 | Andisil VS 65,000 ™ | 13.04 |
| 4 | Andisil XL-1B ™ | 16.84 |
| 5 | Aerosil R8200 ™ | 8.80 |
| 6 | Water | 50.00 |
| 7 | Veegum Pro | 4.00 |
| 8 | Solagum AX | 1.00 |
| 9 | Dow Corning 5329 | 5.00 |

Procedure:

Components 1 to 5 were combined and mixed under vacuum (Mixture A). In a separate vessel, components 6 to 7 were mixed with a 4-blade, 40 mm propeller at 550 rpm until the mixture was homogenous and the particulates were fully wetted (Mixture B). Component 8 was added to Mixture B and mixed in with a 4-blade 40 mm propeller at 500 rpm until the mixture thickened and became homogenous. Component 9 was added to Mixture B and mixed in with a 4-blade 40 mm propeller at 500 rpm for 10 minutes. Mixture A was added slowly to Mixture B under continuous mixing at 500 rpm. The product was homogenized for 5 minutes at 10,000 rpm.

Formulation 79-90-B

| Component No. | Component | Percent of Formulation (%) |
| --- | --- | --- |
| 1 | Andisil VS 500 ™ | 0.68 |
| 2 | Andisil MV 2000 ™ | 1.04 |
| 3 | Andisil VS 65,000 ™ | 16.95 |
| 4 | Andisil XL-1B ™ | 21.89 |
| 5 | Aerosil R8200 ™ | 11.44 |
| 6 | Water | 40.00 |
| 7 | Veegum Pro | 4.00 |
| 8 | Solagum AX | 1.00 |
| 9 | Dow Corning 5329 | 3.00 |

Procedure:

Components 1 to 5 were combined and mixed under vacuum (Mixture A). In a separate vessel, components 6 to 7 were mixed with a 4-blade, 40 mm propeller at 550 rpm until the mixture was homogenous and the particulates were fully wetted (Mixture B). Component 8 was added to Mixture B and mixed in with a 4-blade 40 mm propeller at 500 rpm until the mixture thickened and became homogenous. Component 9 was added to Mixture B and mixed in with a 4-blade 40 mm propeller at 500 rpm for 10 minutes. Mixture A was added slowly to Mixture B under continuous mixing at 500 rpm. The product was homogenized for 5 minutes at 10,000 rpm.

Formulation 88-70

| Component No. | Component | Percent of Formulation (%) |
| --- | --- | --- |
| 1 | Andisil VS10,000 | 28.7% |
| 2 | Andisil VS165,000 | 6.7% |
| 3 | Andisil XL-11 | 14.0% |
| 5 | Aerosil R8200 | 18.2% |
| 6 | KF6013 | 2.1% |
| 7 | TMF 1.5 | 2.3% |
| 8 | USG 102 | 2.3% |
| 9 | DI water | 22.3% |
| 10 | Glycerin | 1.1% |
| 11 | Jeen BUGL | 1.2% |
| 12 | Jeecide Cap-5 | 1.0% |

Procedure:

Components 1-8 (part A) and components 9-11 (part B). Part B was introduced to part A while mixing part A with a flat propeller blade at 500 RPM. The resulting solution was mixed until a uniform emulsion formed. Component 12 was subsequently added to the emulsion.

Formulation 88-72

| Component No. | Component | Percent of Formulation (%) |
| --- | --- | --- |
| 1 | Andisil VS10,000 | 28.60% |
| 2 | Andisil VS165,000 | 6.69% |
| 3 | Andisil XL-11 | 13.99% |
| 5 | Aerosil R8200 | 18.16% |
| 6 | KF6013 | 2.08% |
| 7 | TMF 1.5 | 2.25% |
| 8 | USG 102 | 2.35% |
| 9 | Pink tint mix | 0.02% |
| 10 | DI water | 22.25% |
| 11 | Glycerin | 1.16% |
| 12 | Jeen BUGL | 1.24% |
| 13 | Veegum Ultra Granules | 0.11% |
| 14 | Kaolin USP BC2747 | 0.10% |
| 15 | Jeecide Cap-5 | 1.00% |

Procedure:

Components 1-9 (Phase A) were mixed separately from components 10-14 (Phase B). Phase B was added to Phase A while mixing at 500 RPM using a 4 paddle mixing blade, followed by homogenization using a Silverson homogenizer for 1 hour at 3000 to 5000 RPM. Subsequently, component 15 was added using mixing blade at 200 rpm.

Formulation 88-75-2

| Component No. | Component | Percent of Formulation (%) |
| --- | --- | --- |
| 1 | Andisil VS10,000 | 21.39% |
| 2 | Andisil VS165,000 | 5.00% |
| 3 | Andisil XL-11 | 10.47% |
| 4 | Aerosil R8200 | 13.58% |
| 5 | RM2051 | 1.95% |
| 6 | DC 556 | 3.12% |
| 7 | FZ3196 | 3.11% |
| 8 | Squalane | 1.85% |
| 9 | USG 102 | 6.90% |
| 10 | Jeechem BUGL | 1.85% |
| 11 | DI water | 29.03% |
| 12 | Polyglycol P425 | 1.22% |
| 13 | Jeecide Cap-5 | 0.52% |

Procedure:

Components 1-4 (Phase A) were mixed. Separately, components 5-9 were also mixed (Phase B) until a uniform dispersion was formed. Components 10-12 (Phase C) were also mixed separately. Phase C was slowly introduced into Phase B, while mixing at 700 RPM with 4 blade propeller rod to create a uniform emulsion (Phase D). Phase D was slowly introduced into Phase A at 700 RPM until uniform, and the resulting formulation was mixed for 5 minutes. Component 13 was added and mixed for 2 minutes.

Formulation 88-75-3

| Component No. | Component | Percent of Formulation (%) |
| --- | --- | --- |
| 1 | Andisil VS10,000 | 18.64% |
| 2 | Andisil VS165,000 | 4.36% |
| 3 | Andisil XL-11 | 9.12% |
| 4 | Aerosil R8200 | 11.84% |
| 5 | RM2051 | 2.21% |
| 6 | DC 556 | 3.53% |
| 7 | FZ3196 | 3.52% |
| 8 | Squalane | 2.10% |
| 9 | USG 102 | 7.81% |
| 10 | Jeechem BUGL | 2.10% |
| 11 | DI water | 32.85% |
| 12 | Polyglycol P425 | 1.38% |
| 13 | Jeecide Cap-5 | 0.54% |

Procedure:

Components 1-4 (Phase A) were mixed. Components 5-9 (Phase B) were mixed separately from Phase A until a uniform dispersion was formed. Components 10-12 (Phase C) were also mixed separately from Phase A and Phase B. Phase C was slowly introduced into Phase B, while mixing at 700 RPM with 4 blade propeller rod to create a uniform emulsion (Phase D). Phase D was Slowly introduced to Phase A at 700 RPM until uniform, and mixed for 5 minutes. Component 13 was then introduced to the resulting formulation and mixed for 2 minutes, followed by homogenization at 5000 RPM for 15 minutes.

Formulation 88-80

| Component No. | Component | Percent of Formulation (%) |
|---|---|---|
| 1 | Andisil VS10,000 | 12.72% |
| 2 | Andisil VS165,000 | 2.98% |
| 3 | Andisil XL-11 | 6.23% |
| 4 | Aerosil R8200 | 8.08% |
| 5 | RM2051 | 2.79% |
| 6 | DC 556 | 4.45% |
| 7 | FZ3196 | 4.44% |
| 8 | Squalane | 2.64% |
| 9 | USG 102 | 9.85% |
| 10 | Jeechem BUGL | 2.64% |
| 11 | DI water | 41.44% |
| 12 | Polyglycol P425 | 1.74% |
| 13 | Jeecide Cap-5 | 0.005% |

Procedure:

Components 1-4 (Phase A) were mixed. Components 5-9 (Phase B) were mixed separately from Phase A until a uniform dispersion was formed. Components 10-12 (Phase C) were also mixed separately from Phase A and Phase B. Phase C was slowly introduced into Phase B, while mixing at 700 RPM with 4 blade propeller rod to create a uniform emulsion (Phase D). Component 13 was added to Phase D and mixed for 2 minutes. The resulting emulsion was lowly introduced into Phase A at 700 RPM until uniform, and mixed for 5 minutes, followed by homogenization at 9000 RPM for 7 minutes.

Formulation 88-85-1

| Component No. | Component | Percent of Formulation (%) |
|---|---|---|
| 1 | RM 2051 | 3.28% |
| 2 | FZ 3196 | 4.92% |
| 3 | USG 102 | 12.11% |
| 4 | water | 48.83% |
| 5 | Jeecide CAP-5 | 0.87% |
| 6 | Andisil VS10,000 | 12.72% |
| 7 | Andisil VS165,000 | 2.98% |
| 8 | Andisil XL-11 | 6.23% |
| 9 | Aerosil R8200 | 8.08% |

Procedure:

Components 1-3 (Phase A) were mixed. Component 4 was added while mixing Phase A, until a white emulsion formed. Components 6-9 (Phase B) were mixed and Phase B was subsequently added to the emulsion and mixed for 5 minutes at 1300 RPM. The resulting formulation was homogenized (Silverson) for 5 minutes and component 5 was added, followed by mixing for 2 minutes at 700 RPM with a propeller blade.

Formulation 88-85-2

| Component No. | Component | Percent of Formulation (%) |
|---|---|---|
| 1 | RM 2051 | 2.62% |
| 2 | FZ 3196 | 3.93% |
| 3 | USG 102 | 9.68% |
| 4 | water | 39.03% |
| 5 | Jeecide CAP-5 | 0.78% |
| 6 | Andisil VS10,000 | 18.6% |
| 7 | Andisil VS165,000 | 4.4% |
| 8 | Andisil XL-11 | 9.1% |
| 9 | Aerosil R8200 | 11.8% |

Procedure:

Components 1-3 (Phase A) were mixed. Component 4 was added while mixing phase A until a white emulsion formed. Components, 6-9 (Phase B) were mixed separately and subsequently added to the emulsion while mixing at 1300 RPM for 5 minutes. The mixture was homogenized (Silverson) for 5 minutes. Component 5 was added and the resulting formulation was mixed for 2 minutes at 700 RPM with a propeller blade.

Formulation 88-83-V2

| Component No. | Component | Percent of Formulation (%) |
|---|---|---|
| 1 | RM 2051 | 3.3% |
| 2 | FZ 3196 | 3.3% |
| 3 | DC 2-1184 fluid | 10.0% |
| 4 | USG 102 | 3.3% |
| 5 | water | 46.3% |
| 6 | Jeecide CAP-5 | 0.3% |
| 7 | Andisil VS10,000 | 14.1% |
| 8 | Andisil VS165,000 | 3.3% |
| 9 | Andisil XL-11 | 6.9% |
| 10 | Aerosil R8200 | 9.0% |

Procedure:

Components 1-4 were mixed (Phase A), followed by addition of component 5, until a white emulsion formed. Component 6 was added to the emulsion and mixed for 5 minutes (emulsion base). Components 7-10 (Phase B) were mixed separately and added to the emulsion base at 1300 RPM, followed by mixing for 5 minutes and homogenization (Silverson) for 10 minutes.

Formulation 88-83-V3

| Component No. | Component | Percent of Formulation (%) |
|---|---|---|
| 1 | RM 2051 | 3.3% |
| 2 | DC 2-1184 fluid | 13.3% |
| 3 | water | 49.7% |
| 4 | Jeecide CAP-5 | 0.3% |
| 5 | Andisil VS10,000 | 14.1% |
| 6 | Andisil VS165,000 | 3.3% |
| 7 | Andisil XL-11 | 6.9% |
| 8 | Aerosil R8200 | 9.0% |

Procedure:

Components 1 and 2 were mixed (Phase A), followed by addition of component 3, until a white emulsion formed. Component 4 was added to the emulsion and mixed for 5 minutes (emulsion base). Components 5-8 (Phase B) were mixed separately and added to the emulsion base at 1300 RPM, followed by mixing for 5 minutes and homogenization (Silverson) for 10 minutes.

Formulation 83-54
Reactive Constituent and Reinforcing Constituent Composition (Vinyl, Hydride, Fumed Silica)

| Tradename | Description | weight percent | ranges lower | ranges upper |
|---|---|---|---|---|
| Andisil VS10,000 | 0.05 mmol/g vinyl, 10,000 cSt | 42.40% | 30 | 50 |
| Andisil VS165,000 | 0.015 mmol/g vinyl, 165,000 cSt | 9.92% | 5 | 15 |
| Andisil XL-11 | 4.35 mmol/g, 45 cSt | 20.75% | 10 | 30 |
| Aerosil R8200 | Silica Silylate | 26.93% | 20 | 34 |
| | total | 100.00% | | |
| Reactive Reinforcing Component | | | | |
| RM 2051 Thickening Agent | Sodium Polyacrylate (and) Dimethicone (and) Cyclopentasiloxane (and) Trideceth-6 (and) PEG/PPG-18/18 Dimethicone | 3.63% | 3.00% | 5.00% |
| Gransurf 90 | Cetyl PEG/PPG-10/1 Dimethicone | 0.50% | 0.20% | 2.00% |
| PMX-1184 | dimethicone and trisiloxane | 13.63% | 10.00% | 40.00% |
| Water | N/A | 46.00% | 20.00% | 60.00% |
| Vitamin-C complex | Ascorbic Acid | 0.08% | 0.05% | 0.50% |
| Jeecide CAP-5 | Phenoxyethanol, Caprylyl Glycol, Potassium Sorbate, Aqua, Hexylene Glycol | 0.33% | | 1.00% |
| Tween 20 | Polysorbate 20 | 0.33% | | 5.00% |
| Vitamin-A complex | Vitamin A Palmitate 1.7 MIU/g | 0.40% | | 5.00% |
| Vitamin-E complex | Vitamin E Acetate | 0.10% | | 5.00% |
| Reactive constituent and Reinforcing constituent composition (Vinyl, hydride, fumed silica) from above | N/A | 35.00% | 30.00% | 60.00% |
| | total | 100.00% | | |

Procedure:

Formulation 83-54 was prepared by a procedure similar to 88-83-V3.

Andisil VS10,000, Andisil VS165,000, Andisil XL-11 were obtained from Anderson and Associates, Aerosil R8200 was obtained from Evonik, and the four components were mixed by Crisil. RM 2051 Thickening Agent and PMX-1184 were obtained from Dow. Gransurf 90 was obtained from Grant. Vitamin-C complex and Vitamin A comples were obtained from DSM. Jeecide CAP-5 was obtained from Jeen. Tween 20 was obtained from Croda. Vitamin-E complex was obtained from TRI-K.

The cross-linking component second step includes formulations 60-148-99, 60-144-San 86-114, and 86-141c shown below.

Formulation 60-148-99

| Component No. | Component | Percent of Formulation (%) |
|---|---|---|
| 1 | Water | 28.60 |
| 2 | Plantacare 818UP | 0.49 |
| 3 | Propylene Glycol | 19.72 |
| 4 | Glycerin | 3.94 |
| 5 | Jeechem BUGL | 9.86 |
| 6 | Sodium Chloride | 0.99 |
| 7 | Dow Elastomer Blend 9011 | 9.86 |

-continued

| Component No. | Component | Percent of Formulation (%) |
|---|---|---|
| 8 | Dow Elastomer Blend 9041 | 9.86 |
| 9 | Dow 245 Fluid | 7.89 |
| 10 | Jeensilc CPS-312 | 1.97 |
| 11 | Nylon 10-12 | 4.64 |
| 12 | Chronosphere Optical Brite | 0.18 |
| 13 | Platinum divinyl complex PC 075.3 | 1.00 |

Procedure:

Components 1-6 were combined and mixed at 750 RPM for two minutes with a 4-blade 40 mm propeller until homogenous to create an aqueous phase. In a separate container components 7-10 were mixed at 750 RPM for two minutes with a 4-blade 40 mm propeller until homogenous to create a Silicon Mixture A. To the aqueous phase, components 11 and 12 were added and mixed at 750 RPM with a 4-blade 40 mm propeller. The mixing speed was increased to 1000 RPM and the mixture was mixed until homogenous and thickened. Component 13 was added and stirred at 1000 RPM for 1 minute, then homogenized at 25,000 RPM for 5 minutes.

Formulation 60-144-San

| Component No. | Component | Percent of Formulation (%) |
|---|---|---|
| 1 | Water | 67.47 |
| 2 | Carbopol Ultrez 21 | 1.01 |
| 3 | Denatured Ethanol 190 Proof | 29.35 |
| 4 | Glycerin | 2.02 |
| 5 | 2% Sodium Hydroxide | 0.20 |
| 6 | Platinum divinyl complex 3% PC 075.3 | 1.99 |

Procedure:

Components 1 and 2 were gently blended with a 4-blade 40 mm propeller blade at 250 RPM until the Carbopol was completely wetted and the mixture was free of white particulates. Components 3 and 4 were added under moderate agitation provided by a 4-blade 40 mm propeller at 500 RPM. Component 5 was added dropwise under moderate agitation provided by a 4-blade 40 mm propeller at 550 RPM until the mixture was homogenous and thickened. Component 6 was added under moderate agitation provided by a 4-blade 40 mm propeller at 550 RPM, followed by mixing at 1000 RPM for 5 minutes until the mixture was homogeneous.

Formulation 86-114 and 86-141c

| Tradename | Description | weight percent | Supplier | lower | upper |
|---|---|---|---|---|---|
| Platinum Divinyl Complex 2% PT-50175F (CAS# 68478-92-2, 2627-95-4, 68083-19-2) | Karstedt's catalyst in stabilizing vinyl-dimethicone | 1.00% | Umicore | 0.50% | 2.50% |
| | | 1.00% total | | | |

| 86-114 | Crosslinking Component # 1 | | | lower | upper |
|---|---|---|---|---|---|
| Dow 9011 Elastomer Blend | Cyclopentasiloxane (and) PEG-12 Dimethicone Crosspolymer | 10.00% | Dow Corning | 5.00% | 20.00% |
| Dow 9045 Elastomer Blend | Cyclopentasiloxane and Dimethicone Crosspolymer | 10.00% | Dow Corning | 5.00% | 20.00% |
| PMX-0245 | Cyclopentasiloxane | 10.00% | Dow Corning | 5.00% | 25.00% |
| Water | | 28.50% | NA | — | 90.00% |
| Sodium Chloride | Sodium Chloride | 1.00% | Spectrum | — | 5.00% |
| Plantacare 818 UP | Coco-Glucoside | 0.50% | Cognis | — | 4.00% |
| Tween 20 | Polysorbate 20 | 0.00% | Cognis | — | 2.00% |
| Propylene Glycol | Propylene Glycol | 20.00% | Ruger Chemical Co | — | 40.00% |
| Lipo Polyglycol ® 200 | PEG-4 | 0.00% | Lipo Chemicals Inc | — | 40.00% |
| Glycerin | Glycerin | 4.00% | Ruger Chemical Co | — | 10.00% |
| Jeechem BUGL | 1,3-Butylene Glycol | 10.00% | Jeen | — | 50.00% |
| Nylon 10-12 | Nylon 12 and Isopropyl Titabium Triisostearate | 4.50% | KOBO | — | 15.00% |
| Jeecide CAP-5 | Phenoxyethanol, Caprylyl Glycol, Potassium Sorbate, Aqua, Hexylene Glycol | 0.50% | Jeen | — | 2.00% |
| PT-50175F | Platinum Divinyldisiloxane | 1.00% | Umicore | 0.50% | 2.50% |
| | total | 100.00% | total | | |

| 86-141c | Crosslinking Component #2 | | | lower | upper |
|---|---|---|---|---|---|
| KSG-240 | Dimethicone/PEG-10/15 Crosspolymer | 10.00% | Shin Etsu | 3.00% | 20.00% |

| Tradename | Description | weight percent | Supplier | lower | upper |
|---|---|---|---|---|---|
| DC 9045 | Cyclopentasiloxane and Dimethicone Crosspolymer | 7.50% | Dow Corning | | 25.00% |
| KF-995 | Cyclopentasiloxane | 11.50% | Shin Etsu | | 25.00% |
| KF-6028 | PEG-9 Polydimethylsiloxyethyl Dimethicone | 1.00% | Shin Etsu | | 4.00% |
| Water | | 28.25% | NA | | 90.00% |
| Sodium Chloride | Sodium Chloride | 1.00% | Spectrum | | 5.00% |
| Plantacare 818 UP | Coco-Glucoside | 0.50% | Cognis | | 4.00% |
| Tween 20 | Polysorbate 20 | 0.00% | Cognis | | 2.00% |
| Propylene Glycol | Propylene Glycol | 20.00% | Ruger Chemical Co | | 40.00% |
| Lipo Polyglycol ® 200 | PEG-4 | 0.00% | Lipo Chemicals Inc | — | 40.00% |
| Glycerin | Glycerin | 4.00% | Ruger Chemical Co | | 10.00% |
| Jeechem BUGL | 1,3-Butylene Glycol | 10.00% | Jeen | | 50.00% |
| Nylon 10-12 | Nylon 12 and Isopropyl Titabium Triisostearate | 4.50% | KOBO | | 15.00% |
| Jeecide CAP-5 | Phenoxyethanol, Caprylyl Glycol, Potassium Sorbate, Aqua, Hexylene Glycol | 0.50% | Jeen | | 2.00% |
| PT-50175F | Platinum Divinyldisiloxane | 1.25% | Umicore | | 2.50% |
| | | 100.00% | total | | |

Procedure for 86-114:

Components 1-3 were combined and mixed at 750 RPM for two minutes with until homogenous to create an silicone phase. In a separate container components 4-11 and 13 were mixed at 750 RPM for 15 minutes with a until homogenous to create a water phase. The water phase was added slowly to the silicone phase and mixed at 750 RPM. The mixing speed was increased to 2000 RPM and the mixture was mixed until homogenous and thickened. Component 12 was added and stirred at 1000 RPM for 5 minutes. Component 14 was added and stirred at 1000 RPM for 5 minutes.

Procedure for 86-141c:

Components 1-4 were combined and mixed at 750 RPM for two minutes with until homogenous to create an silicone phase. In a separate container components 5-12 and 14 were mixed at 750 RPM for 15 minutes with a until homogenous to create a water phase. The water phase was added slowly to the silicone phase and mixed at 750 RPM. The mixing speed was increased to 2000 RPM and the mixture was mixed until homogenous and thickened. Component 13 was added and stirred at 1000 RPM for 5 minutes. Component 15 was added and stirred at 1000 RPM for 5 minutes.

Example 5: Development of Cleanser to Remove Therapeutic Compositions

It was found that commercially available cleansers were not effective at removing the film formed upon application of the therapeutic compositions of the invention. To evaluate the performance of the cleansers, the film was applied to facial skin of volunteers. Following six to eight hours, the cleanser was rubbed onto the film and left on the film for 30 seconds. The subject was then instructed to remove the film with a towelette of a given surface roughness by gentle wiping the swollen film from the skin. The following commercially available products were tested:

Philosophy Purity Made Simple
Shiseido Benefiance Creamy Cleansing foam
Noxema
Estee Lauder Perfectly Clean Splash Away Foaming Cleanser
Makeup forever sens'eyes
Loreal go 360clean deep
Clinique naturally gentle eye makeup remover
Olay Total Effects 7 in 1 antiaging cleanser
Olay dual action cleanser and pore scrub
Gamier Skin Renew
Lancome Bi-Facil double action make-up remover
Neutrogena deep clean invigorating foaming scrub
Olay regenerist daily regenerating cleanser
CVS pharmacy deep cleansing makeup remover
Neutrogena Ageless essentials Continuous Hydration Cream Cleanser
CVS cleansing and makeup remover
Yes to cucumbers natural glow facial towelettes As none of the aforementioned products were effective at removing the film, a cleanser was prepared to disrupt the mechanical integrity of the film and to facilitate the delivery of the cleanser components into the film. Without being bound by theory, the removal mechanism can be described in four steps with key formula components for each step indicated in parentheses:

1. Film wetting (Silsoft 034, Silsoft ETS, 5CS dimethicone)
2. Penetration of formula components (siloxane emulsifiers, siloxane phase, glycols, Cremaphor EL)

3. Film swelling (Silsoft 034, Silsoft ETS, Isododecane, 5CS dimethicone)
4. Film release from skin (glycols, water)

Silsoft 034, Silsoft ETS, 5CS dimethicone readily wet the surface of the film. The siloxane emulsifiers or the Cremaphor EL incorporate the aqueous phase into the siloxane phase, and may facilitate delivery of the film swelling components into the film. Silsoft 034, isododecane, and Silsoft ETS contribute to swelling the film and mechanical disruption. This enables penetration of the aqueous phase, hydration of the skin and reduction of the film's adhesion to the skin.

Tables 15-17, below, provide compositions that were effective in removing the film:

TABLE 15

|  | w/w | gm |
|---|---|---|
| siloxane phase | | |
| Silsoft 034 (caprylyl methicone) | 9.7% | 5 |
| Isododecane | 19.4% | 10 |
| Silsoft ETS (ethyl trisiloxane) | 19.4% | 10 |
| Aerogel VM2270 | 1.5% | 0.763 |
| siloxane emulsifiers | | |
| Shin Etsu KSG 820 | 3.9% | 2 |
| Shin Etsu KF 6038 | 3.9% | 2 |
| aqueous phase | | |
| propylene glycol | 4.9% | 2.5 |
| butylene diglycol | 4.9% | 2.5 |
| glycerol | 1.9% | 1 |
| MPDiol | 7.8% | 4 |
| DI water | 19.4% | 10 |
| neolone PE | 0.5% | 0.27 |
| chronosphere optical brite | 0.6% | 0.3 |
| granpowder nylon | 2.1% | 1.1 |

TABLE 16

| Component No. | Component | Percent of Formulation (%) |
|---|---|---|
| 1 | Glycerin | 3.00% |
| 2 | water | 43.98% |
| 3 | dowanol DPM | 6.00% |
| 5 | cremaphor EL | 6.00% |
| 6 | silsoft ETS | 30.00% |
| 7 | DM5 CS | 10.00% |
| 8 | prestige pearlescent beige | 0.02% |
| 9 | Jeecide cap 5 | 1.00% |

TABLE 17

| Component No. | Component | Percent of Formulation (%) |
|---|---|---|
| 1 | Glycerin | 3.11% |
| 2 | water | 46.23% |
| 3 | dowanol DPM | 6.20% |
| 4 | cremaphor EL | 6.22% |
| 5 | silsoft ETS | 12.43% |
| 6 | DC 200 Fluid (1 cSt) | 15.49% |
| 7 | DM5 CS | 9.30% |
| 8 | Xirona caribbean blue | 0.02% |
| 9 | Jeecide cap 5 | 1.00% |

Procedure:

Components 1-4 and 9 were mixed until a clear dispersion formed (Phase A). Compounds 5-8 were mixed separately until a uniform solids dispersion was formed. Phase A was subsequently added to Phase B and mixed.

Example 6. Viscosity Measurements

The viscosity of a fluid can be measured by many methods known to one of skill in the art. Specifically, "The rheology handbook: for users of rotational and oscillatory rheometers By Thomas G. Mezger" or ASTM standards such as ASTM D3835-08, ASTM D2857-95, ASTM D2196-10, and ASTM D2983-09 instruct one of skill in the art on how to measure the viscosity of a fluid. Illustrative methods also include the following methods:

Method A

I. Overview

This protocol determines the viscosity (cP) on a Brookfield Viscometer. This protocol can be performed on a wide variety of formulations including but not limited to immediate effects treatment, and perfector.

II. Background

The viscosity of formulation is critical to its performance and its aesthetics. Furthermore a change in viscosity with time or exposure to a stress condition is an important indicator of formulation instability. As such, it is important to be able to reproducibly and accurately evaluate formulation viscosity. The following protocol can be used to determine the viscosity at single shear rate of a formulation whose viscosity is between 50 and 300 Pas.

III. Materials

A full 2 oz to 8 oz jar containing formulation of interest
Brookfield DV-II+ Pro EXTRA Viscometer and RV-6 spindle.
Test requires ~5 minutes per sample IV. Analytical Precautions Clean the viscometer geometry prior to use
Insert the geometry to the appropriate depth in the center of the sample container
Insure the container is stationary during the test V. Protocol 5.1 Preparing Equipment:

1. Turn on the Brookfield DV-II+ Pro EXTRA Viscometer by pressing a switch in the back of the instrument. Select "External Mode" by pressing the up arrow on the instrument control panel.
2. Start the Rheocalc software, a shortcut to which can be found on the desktop
3. Zero the viscometer by clicking the lightning symbol on the dashboard tab (Instrument geometry should NOT be installed)
4. Find RV-6 test geometry and clean with 50%/50% IPA/Mineral Spirits mixture, then wipe dry
5. Insert RV-6 geometry by pulling the instrument geometry holder sleeve up.
6. Pick the test method by clicking Test tab, and opening Hold0.5-RV6-081511.RCP method.

5.2 Preparing Sample:

1. No special sample preparation is required other than doing a visual inspection to ensure the sample appears uniform.

5.3 Perform Viscosity Measurement:
1. Insert the geometry into the 2 to 8 oz of sample under.
    i. Insure that the geometry is inserted to the correct measuring height as indicated by thin section in the rod of the geometry
    ii. Insure that the geometry is centered in the jar
2. Adjust the stand so as to keep the sample and the geometry in the appropriate relative position.
3. Click the small play button in the test tab to start the test
4. Name the data file appropriately and save the file to the appropriate location
5. Allow the test to run to completion, then save your data for later analysis
6. To test another sample:
    i. Slide the sample stand out and remove the sample from the instrument
    ii. Remove the geometry from the instrument and gently wipe down all surfaces with 50% IPA, 50% Mineral Spirit mixture. Dry with a lint free wipe.
    iii. Replace the geometry, return to test tab and start next test
7. After finishing with the last test sample, clean geometry with 50% IPA, 50% Mineral Spirit mixture, then wipe dry and place back in geometry box.

VI. Data Analysis
1. Open datafile (*.DB) and click the export button to obtain an excel file containing the data.
2. Locate the ViscometerPerfector Template_JL-081511-v1-beta1.xlsx Excel template for data analysis
3. Paste the data into the first sheet
4. Record the average viscosity and the standard deviation
5. Save the template as an electronic record with a new name that references the analyzed sample.
1. Repeat analysis for each data set.

Method B

I. Overview

This protocol determines the viscosity (Pas) at 0.5 l/s, Shear Thinning factor (Pa*s^2), and the strain rate of instability. This protocol can be performed on a wide variety of formulations including but not limited to immediate effects treatment, and perfector, along with any other "cream" or "lotion"

II. Background

The viscosity of formulas and its change has been correlated to stability of formulations. As such, it is important to be able to reproducibly and accurately evaluate their viscosity properties to be used as a predictive tool for stability of Immediate Effects active prototypes. The following protocol can be used to determine the viscosity, shear thinning factor, and strain rate of instability.

III. Materials
>1 g Formulation of Interest
Bohlin CVO100 Rheometer mounted with 20 mm Parallel plate geometry
Test requires ~12 minutes per sample IV. Analytical Precautions
Clean sides of the geometry are critical for accurate test results
Any deviations must be noted V. Protocol
5.1 Preparing Equipment:
8. Set up the Bohlin Rheometer
    a. Turn on the instrument
    b. Turn on the temperature controller
    c. Start the Bohlin software
    d. Load the viscosity stability test template
    e. Make sure both the geometry and plate are clean
9. Install the geometry
    a. Zero the instrument and you are now ready to being testing.
10. For testing of multiple samples simply raise and clean the geometry first with a dry wipe, then with a 50%/50% IPA/Mineral Spirits mixture, then again with a dry wipe.

5.2 Preparing Sample:
1. No special sample preparation is required other than doing a visual inspection to ensure the sample appears uniform.

VI. Perform the Viscosity Test
7. Place ~1 g of mixed material onto the bottom plate in a mound centered below the geometry
8. Lower the geometry to the correct gap (250 um)
9. Clean the excess material from the sides of the geometry using the flat end of a spatula
10. Allow the test to run to completion, then save your data for later analysis
11. To continue onto the next test, raise the geometry and remove the sample from the instrument. Gently wipe down all surfaces with 50% ipa/50% mineral spirits mixture. Dry with a lint free wipe.
12. You are now ready to commence the next cure test VII. Data Analysis:
2. Locate the following Excel Template for the data analysis iscosityStabilityTemplate061411-v2
3. Paste the raw instrument data from the appropriate Bohlin Viscometry Data File file into A:2 of sheet 1 (near the left corner) of the excel document
4. Paste the sample name into A:1 of sheet 1 of the excel document
5. Record the calculated "Viscosity (Pas) at 0.5 l/s" as viscosity
6. Record the calculated "Shear Thining factor (Pa*s^2)" as the shear thinning factor
7. Record the calculated "Strain Rate of instability" as the Strain Stability (Scale is out of 100)
8. Save the completed template as an electronic record with an appropriate file name
9. Repeat steps 2 to 7 for remaining raw data Example 7: Use of Compositions to Treat Headaches and Wounds A. Headache Use:

The reactive reinforcing component formulation of the invention can be used to treat tension headaches. A representative formulation is provided below.

Application.

To treat the headache, apply an even layer of the formulation, approximately 0.05 g per square inch on to the forehead, covering the space between the hair line and the brows. Immediately afterwards, apply the crosslinking component on top, covering and extending past the area covered by the reactive reinforcing component. The crosslinking component can be applied at a concentration of approximate 0.1 g per square inch. Allow approximately 15 minutes for the applied formulations to set and form a visually pleasing film.

Effect of Film on Treatment Area.

The resulting film provides mechanical support that relieves the load on face and neck muscles that are responsible for tension headaches effectively relieving the headache. Within minutes to hours the muscles relax in response to the reduced load and the headache is reduced. The film should be worn for as long as headache relief is desired. To remove, a removal solution can be used. The product can be reapplied daily or as often as desired by repeating the procedure above.

Additionally, the support offered by the set formulations produces a brow lift. The brow lift improves the appearance of the eye and diminishes the eye obstruction by the brow (eye lid drooping) in some cases improving comfort and vision. The set formulations are cosmetically pleasing, visual unobtrusive, and provide a non-invasive solution to a tension headache without systemic chemical side effects associated with oral or injection medication.

B. Wound Use:

The reactive reinforcing component formulation of the invention can be used to treat a skin wound. A representative formulation for this use is provided below.

Effect of Film on Treatment Area.

Within minutes to hours the skin relaxes in response to the reduced load and the wound healing time is reduced. The resulting film provides mechanical support that relieves the load on wound, reducing scar formation. Furthermore the film provides an occlusive protective covering for the wound that protects the wound from physical and chemical attack while it is healing. The film has hydration and biocompatibility properties that improve wound recovery. Furthermore the film aids the controlled sustained delivery of imbedded wound healing actives directly to the wound site. The film is comfortable and aesthetically unobtrusive aiding, thereby increasing subject compliance.

Formulation 79-110-1

Reactive Constituent and Reinforcing Constituent Composition (Vinyl, Hydride, Fumed Silica)

| Tradename | Description | weight percent | ranges lower | ranges upper |
|---|---|---|---|---|
| Andisil VS10,000 | 0.05 mmol/g vinyl, 10,000 cSt | 37.7% | 30 | 50 |
| Andisil VS165,000 | 0.015 mmol/g vinyl, 165,000 cSt | 8.8% | 5 | 15 |
| Andisil XL-11 | 4.35 mmol/g, 45 cSt | 18.5% | 10 | 30 |
| Aerosil R8200 | Silica Silylate | 35.0% | 20 | 50 |
| | total | 100.00% | | |
| Reactive Reinforcing Component | | | | |
| RM 2051 Thickening Agent | Sodium Polyacrylate (and) Dimethicone (and) Cyclopentasiloxane (and) Trideceth-6 (and) PEG/PPG-18/18 Dimethicone | 3.63% | 3.00% | 5.00% |
| Dow 9011 Elastomer Blend | Cyclopentasiloxane (and) PEG-12 Dimethicone Crosspolymer | | | 20.00% |
| PMX-1184 | dimethicone and trisiloxane | 13.63% | 10.00% | 40.00% |
| Water | N/A | 46.00% | 20.00% | 60.00% |
| Vitamin-C complex | Ascorbic Acid | 0.08% | 0.05% | 0.50% |
| Jeecide CAP-5 | Phenoxyethanol, Caprylyl Glycol, Potassium Sorbate, Aqua, Hexylene Glycol | 0.33% | | 1.00% |
| Tween 20 | Polysorbate 20 | 0.33% | | 5.00% |
| Vitamin-A complex | Vitamin A Palmitate 1.7 MIU/g | 0.40% | | 5.00% |
| Vitamin-E complex | Vitamin E Acetate | 0.10% | | 5.00% |
| Reactive constituent and Reinforcing constituent composition (Vinyl, hydride, fumed silica) from above | N/A | 35.00% | 30.00% | 60.00% |
| | total | 100.00% | | |

Application.

To treat the wound, apply an even layer of the formulation, approximately 0.05 g per square inch on top of and surrounding the wound that has been blotted dry. Immediately afterwards, apply the crosslinking component on top of the formulation, covering and extending past the area covered by the reactive reinforcing component. The crosslinking component can be applied at a concentration of approximate 0.1 g per square inch. Allow approximately 15 minutes for the applied formulations to set and form a visually pleasing film. The film should be worn for as long as the wound persists. To remove, a removal solution can be used. The product can be reapplied daily or as often as desired by repeating the procedure above.

EQUIVALENTS

Those skilled in the art will recognize, or be able to ascertain using no more than routine experimentation, numerous equivalents to the specific polypeptides, nucleic acids, methods, assays and reagents described herein. Such equivalents are considered to be within the scope of this invention and are covered by the following claims.

The invention claimed is:

1. A therapeutic formulation for the formation of a film over the skin of a subject, comprising a reactive reinforcing component comprising a reactive constituent comprising at least one vinyl terminated organopolysiloxane and at least one hydride functionalized polysiloxane, wherein the reactive reinforcing component has a vinyl to functional hydride molar ratio of between about 1:35 and about 1:100.

2. The therapeutic formulation of claim 1, wherein the reactive constituent is capable of being cross-linked by a metal catalyst thereby forming the film over the skin of the subject.

3. The therapeutic formulation of claim 1, wherein the reactive reinforcing component has a vinyl to functional hydride molar ratio of between about 1:40 and about 1:80.

4. The therapeutic formulation of claim 1, wherein the reactive reinforcing component has a vinyl to functional hydride molar ratio of between about 1:50 and about 1:70.

5. The therapeutic formulation of claim 1, wherein the reactive reinforcing component has a vinyl to functional hydride molar ratio of between about 1:55 and about 1:65.

6. The therapeutic formulation of claim 1, wherein the reactive reinforcing component has a viscosity of between about 50,000 and 700,000 cSt or cP at 25° C.

7. The therapeutic formulation of claim 1, wherein the vinyl terminated organopolysiloxane is selected from the group consisting of vinyl terminated polydimethylsiloxane; vinyl terminated diphenylsiloxane-dimethylsiloxane copolymers; vinyl terminated polyphenylmethylsiloxane, vinylphenylmethyl terminated vinylphenylsiloxane-phenylmethylsiloxane copolymer; vinyl terminated trifluoropropylmethylsiloxane-dimethylsiloxane copolymer; vinyl terminated diethyl siloxane-dimethylsiloxane copolymer; vinylmethylsiloxane-dimethylsiloxane copolymer, trimethylsiloxy terminated; vinylmethylsiloxane-dimethylsiloxane copolymers, silanol terminated; vinylmethylsiloxane-dimethylsiloxane copolymers, vinyl gums; vinylmethylsiloxane homopolymers; vinyl T-structure polymers; monovinyl terminated polydimethylsiloxanes; vinylmethylsiloxane terpolymers; vinylmethoxysilane homopolymers and combinations thereof.

8. The therapeutic formulation of claim 1, wherein the hydride functionalized polysiloxane is alkyl terminated.

9. The therapeutic formulation of claim 1, wherein the hydride functionalized polysiloxane is selected from the group consisting of hydride terminated polydimethylsiloxane; polyphenyl-(dimethylhydrosiloxy)siloxane, hydride terminated; methylhydrosiloxane-phenylmethylsiloxane copolymer, hydride terminated; methylhydrosiloxane-dimethylsiloxane copolymers, trimethylsiloxy terminated; polymethylhydrosiloxanes, trimethylsiloxy terminated; polyethylhydrosiloxane, triethylsiloxane, methylhydrosiloxane-phenyloctylmethylsiloxane copolymer; methylhydrosiloxane-phenyloctylmethyl siloxane terpolymer and combinations thereof.

10. The therapeutic formulation of claim 1, wherein the hydride functionalized polysiloxane comprises trimethylsiloxy terminated methylhydrosiloxane-dimethylsiloxane copolymers.

11. The therapeutic formulation of claim 1, wherein the hydride functionalized polysiloxane has a percent SiH content of between about 3 and about 45%; or a SiH content of between about 0.5 and about 10 mmol/g; or a combination of both.

12. The therapeutic formulation of claim 1, wherein the hydride functionalized polysiloxane has a viscosity of about 5 to about 11,000 cSt or cP at 25° C.

13. The therapeutic formulation of claim 1, wherein the hydride functionalized polysiloxane has at least 2 Si—H units on average.

14. The therapeutic formulation of claim 1, wherein the vinyl terminated organopolysiloxane is a polymer of formula IIa and the hydride functionalized polysiloxane is a polymer of formula III:

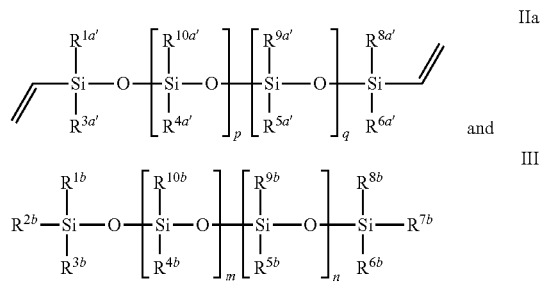

wherein:
$R^{1a'}$, $R^{3a'}$, $R^{4a'}$, $R^{5a'}$, $R^{6a'}$, $R^{8a'}$, $R^{9a'}$ and $R^{10a'}$ are each independently $C_{1-20}$ alkyl, $C_{2-20}$ alkenyl, $C_{5-10}$ aryl, hydroxyl or $C_{1-20}$ alkoxyl;
p and q are each independently an integer from between 10 and 6000;
$R^{1b}$, $R^{2b}$, $R^{3b}$, $R^{6b}$, $R^{7b}$ and $R^{8b}$ are $C_{1-20}$ alkyl;
$R^{4b}$, $R^{5b}$, $R^{9b}$, $R^{10b}$, $R^{7b}$ are each independently selected from the group consisting of hydrogen, $C_{1-20}$ alkyl, $C_{2-20}$ alkenyl, $C_{5-10}$ aryl, hydroxyl and $C_{1-20}$ alkoxyl, wherein at least two of $R^{4b}$, $R^{5b}$, $R^{9b}$, $R^{10b}$ are hydrogen; and
m and n are each independently an integer from between 10 and 6000.

15. The therapeutic formulation of claim 1, wherein the therapeutic formulation further comprises an agent selected from the group consisting of sunscreens, anti-aging agents, anti-acne agents, anti-wrinkle agents, spot reducers, antioxidants, and vitamins.

16. The therapeutic formulation of claim 1, wherein the therapeutic formulation further comprises one or more feel modifiers, tack modifiers, spreadability enhancers, diluents, adhesion modifiers, optics modifiers, particles, volatile siloxanes, emulsifiers, emollients, surfactants, thickeners, solvents, film formers, humectants, preservatives, or pigments.

17. The therapeutic formulation of claim 1, wherein the vinyl terminated organopolysiloxane has a viscosity between about 150,000 and about 185,000 cSt or cP at 25° C., and the hydride functionalized polysiloxane has a viscosity of between about 30 and about 100 cSt or cP at 25° C.

18. The therapeutic formulation of claim 17, wherein the vinyl terminated organopolysiloxane has a viscosity of about 165,000 cSt or cP at 25° C., and the hydride functionalized polysiloxane has a viscosity of about 45 cSt or cP at 25° C.

19. The therapeutic formulation of claim 17, wherein the vinyl terminated organopolysiloxane has a viscosity of about 165,000 cSt or cP at 25° C., and the hydride functionalized polysiloxane has a viscosity of about 50 cSt or cP at 25° C.

20. The therapeutic formulation of claim 17, wherein the vinyl terminated organopolysiloxane has a viscosity of about 10,000 cSt or cP at 25° C.

21. The therapeutic formulation of claim 1, wherein the reactive reinforcing component further comprises mica, zinc oxide, titanium dioxide, aluminum oxide, clay, silica, surface treated mica, surface treated zinc oxide, surface treated titanium dioxide, surface treated aluminum oxide, surface treated clay or surface treated silica.

22. The therapeutic formulation of claim 1, wherein the therapeutic formulation is suitable for use in a two-part therapeutic formulation further comprising a cross-linking component comprising a metal catalyst.

23. The therapeutic formulation of claim 22, wherein the metal catalyst is selected from platinum carbonyl cyclovinylmethylsiloxane complexes, platinum divinyltetramethyldisiloxane complexes, platinum cyclovinylmethylsiloxane complexes, platinum octanaldehyde/octanol complexes, Tris (dibutylsulfide) Rhodium trichloride, tin II octoate, Tin II neodecanoate, dibutyltin diisooctylmaleate, Di-n-butylbis(2, 4-pentanedionate)tin, di-n-butylbutoxychlorotin, dibutyltin dilaurate, dimethyl tin dineodecanoate, dimethylhydroxy (oleate)tin, tin II oleate, or a combination thereof.

24. The therapeutic formulation of claim 22, wherein the metal catalyst is a platinum catalyst.

25. The therapeutic formulation of claim 22, wherein the metal catalyst is a platinum divinyltetramethyldisiloxane complex.

26. The therapeutic formulation of claim 22, wherein the cross-linking component further comprises a vinyl terminated organopolysiloxane.

27. The therapeutic formulation of claim 22, wherein the reactive reinforcing component and the cross-linking component are prevented from coming into contact prior to use.

28. A method for treating wounds, comprising applying to a wound on a subject the formulation of claim 1.

29. A method of treating a stress headache in a subject comprising applying to an appropriate area of the subject's skin the formulation of claim 1 in an amount effective to lift the subject's brow.

30. A kit for the formation of a film over the skin of a subject, wherein the kit comprises a) a first container with a reactive reinforcing component comprising a reactive constituent comprising at least one vinyl terminated organopolysiloxane and at least one hydride functionalized polysiloxane, wherein the reactive reinforcing component has a vinyl to functional hydride molar ratio of between about 1:35 and about 1:100; and b) a second container with a cross-linking component comprising a metal catalyst.

31. The kit of claim 30, wherein the reactive constituent is capable of being cross-linked by a metal catalyst thereby forming the film over the skin of the subject.

32. The kit of claim 30, wherein the reactive reinforcing component has a vinyl to functional hydride molar ratio of between about 1:40 and about 1:80.

33. The kit of claim 30, wherein the reactive reinforcing component has a vinyl to functional hydride molar ratio of between about 1:50 and about 1:70.

34. The kit of claim 30, wherein the reactive reinforcing component has a vinyl to functional hydride molar ratio of between about 1:55 and about 1:65.

35. The kit of claim 30, wherein the reactive reinforcing component has a viscosity of between about 50,000 and 700,000 cSt or cP at 25° C.

36. The kit of claim 30, wherein the vinyl terminated organopolysiloxane is selected from the group consisting of vinyl terminated polydimethylsiloxane; vinyl terminated diphenylsiloxane-dimethylsiloxane copolymers; vinyl terminated polyphenylmethylsiloxane, vinylphenylmethyl terminated vinylphenylsiloxane-phenylmethylsiloxane copolymer; vinyl terminated trifluoropropylmethylsiloxane-dimethylsiloxane copolymer; vinyl terminated diethylsiloxane-dimethylsiloxane copolymer; vinylmethylsiloxane-dimethylsiloxane copolymer, trimethylsiloxy terminated; vinylmethylsiloxane-dimethylsiloxane copolymers, silanol terminated; vinylmethylsiloxane-dimethylsiloxane copolymers, vinyl gums; vinylmethylsiloxane homopolymers; vinyl T-structure polymers; monovinyl terminated polydimethylsiloxanes; vinylmethylsiloxane terpolymers; vinylmethoxysilane homopolymers and combinations thereof.

37. The kit of claim 30, wherein the hydride functionalized polysiloxane is alkyl terminated.

38. The kit of claim 30, wherein the hydride functionalized polysiloxane is selected from the group consisting of hydride terminated polydimethylsiloxane; polyphenyl-(dimethylhydrosiloxy)siloxane, hydride terminated; methylhydrosiloxane-phenylmethylsiloxane copolymer, hydride terminated; methylhydrosiloxane-dimethylsiloxane copolymers, trimethylsiloxy terminated; polymethylhydrosiloxanes, trimethylsiloxy terminated; polyethylhydrosiloxane, triethylsiloxane, methylhydrosiloxane-phenyloctylmethylsiloxane copolymer; methylhydrosiloxane-phenyloctylmethylsiloxane terpolymer and combinations thereof.

39. The kit of claim 30, wherein the hydride functionalized polysiloxane comprises trimethylsiloxy terminated methylhydrosiloxane-dimethylsiloxane copolymers.

40. The kit of claim 30, wherein the hydride functionalized polysiloxane has a percent SiH content of between about 3 and about 45%; or a SiH content of between about 0.5 and about 10 mmol/g; or a combination of both.

41. The kit of claim 30, wherein the hydride functionalized polysiloxane has a viscosity of about 5 to about 11,000 cSt or cP at 25° C.

42. The kit of claim 30, wherein the hydride functionalized polysiloxane has at least 2 Si—H units on average.

43. The kit of claim 30, wherein the vinyl terminated organopolysiloxane is a polymer of formula IIa and the hydride functionalized polysiloxane is a polymer of formula III:

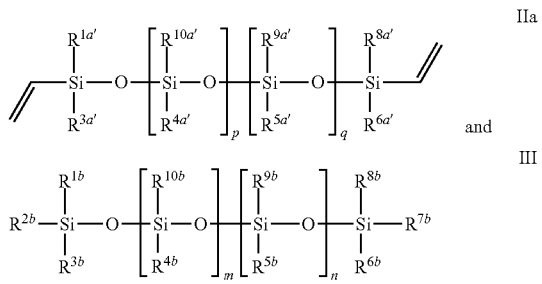

wherein:
$R^{1a'}$, $R^{3a'}$, $R^{5a'}$, $R^{6a'}$, $R^{8a'}$, $R^{9a'}$ and $R^{10a'}$ are each independently $C_{1-20}$ alkyl, $C_{2-20}$ alkenyl, $C_{5-10}$ aryl, hydroxyl or $C_{1-20}$ alkoxyl;

p and q are each independently an integer from between 10 and 6000;

$R^{1b}$, $R^{2b}$, $R^{3b}$, $R^{6b}$, $R^{7b}$ and $R^{8b}$ are $C_{1-20}$ alkyl;

$R^{4b}$, $R^{5b}$, $R^{9b}$, $R^{10b}$, $R^{7b}$ are each independently selected from the group consisting of hydrogen, $C_{1-20}$ alkyl, $C_{2-20}$ alkenyl, $C_{5-10}$ aryl, hydroxyl and $C_{1-20}$ alkoxyl, wherein at least two of $R^{4b}$, $R^{5b}$, $R^{9b}$, $R^{10b}$ are hydrogen; and m and n are each independently an integer from between 10 and 6000.

44. The kit of claim 30, wherein the therapeutic formulation further comprises an agent selected from the group consisting of sunscreens, anti-aging agents, anti-acne agents, anti-wrinkle agents, spot reducers, anti-oxidants, and vitamins.

45. The kit of claim 30, wherein the therapeutic formulation further comprises one or more feel modifiers, tack modifiers, spreadability enhancers, diluents, adhesion modifiers, optics modifiers, particles, volatile siloxanes, emulsifiers, emollients, surfactants, thickeners, solvents, film formers, humectants, preservatives, or pigments.

46. The kit of claim 30, wherein the vinyl terminated organopolysiloxane has a viscosity between about 150,000 and about 185,000 cSt or cP at 25° C., and the hydride functionalized polysiloxane has a viscosity of between about 30 and about 100 cSt or cP at 25° C.

47. The kit of claim 46, wherein the vinyl terminated organopolysiloxane has a viscosity of about 165,000 cSt or cP at 25° C., and the hydride functionalized polysiloxane has a viscosity of about 45 cSt or cP at 25° C.

48. The kit of claim 46, wherein the vinyl terminated organopolysiloxane has a viscosity of about 165,000 cSt or cP at 25° C., and the hydride functionalized polysiloxane has a viscosity of about 50 cSt or cP at 25° C.

49. The kit of claim 46, wherein the vinyl terminated organopolysiloxane has a viscosity of about 10,000 cSt or cP at 25° C.

50. The kit of claim 30, wherein the reactive reinforcing component further comprises mica, zinc oxide, titanium dioxide, aluminum oxide, clay, silica, surface treated mica, surface treated zinc oxide, surface treated titanium dioxide, surface treated aluminum oxide, surface treated clay or surface treated silica.

51. The kit of claim 30, wherein the metal catalyst is selected from platinum carbonyl cyclovinylmethylsiloxane complexes, platinum divinyltetramethyldisiloxane complexes, platinum cyclovinylmethylsiloxane complexes, platinum octanaldehyde/octanol complexes, Tris (dibutylsulfide) Rhodium trichloride, tin II octoate, Tin II neodecanoate, dibutyltin diisooctylmaleate, Di-n-butylbis(2,4-pentanedionate)tin, di-n-butylbutoxychlorotin, dibutyltin dilaurate, dimethyl tin dineodecanoate, dimethylhydroxy (oleate)tin, tin II oleate, or a combination thereof.

52. The kit of claim 30, wherein the metal catalyst is a platinum catalyst.

53. The kit of claim 30, wherein the metal catalyst is a platinum divinyltetramethyldisiloxane complex.

54. The kit of claim 30, wherein the cross-linking component further comprises a vinyl terminated organopolysiloxane.

* * * * *